United States Patent
Mallett et al.

(10) Patent No.: US 7,123,150 B2
(45) Date of Patent: Oct. 17, 2006

(54) WASTE CONTAINER IDENTIFICATION SYSTEM

(75) Inventors: Scott R. Mallett, Coto De Caza, CA (US); Randall C. Danta, Tustin, CA (US); Peter Regla, Placentia, CA (US); Alan D. Corey, Newport Beach, CA (US); Alan A. Davidner, Yorba Linda, CA (US)

(73) Assignee: Vesta Medical, LLC, Tustin, CA (US)

( * ) Notice: Subject to any disclaimer, the term of this patent is extended or adjusted under 35 U.S.C. 154(b) by 0 days.

(21) Appl. No.: 10/946,208

(22) Filed: Sep. 21, 2004

(65) Prior Publication Data

US 2005/0119933 A1    Jun. 2, 2005

Related U.S. Application Data

(63) Continuation of application No. 10/945,223, filed on Sep. 20, 2004.

(60) Provisional application No. 60/504,170, filed on Sep. 19, 2003, provisional application No. 60/589,118, filed on Jul. 19, 2004.

(51) Int. Cl.
*G08B 13/14* (2006.01)
*G06F 17/60* (2006.01)

(52) U.S. Cl. .............. 340/572.1; 340/572.8; 340/3.1; 235/385; 235/462.01; 235/435; 235/383; 235/375; 209/703; 209/583; 209/930; 220/346; 220/345; 355/75; 355/72; 355/40; 355/74; 355/41; 705/1; 705/2; 705/3; 705/4

(58) Field of Classification Search .............. None
See application file for complete search history.

(56) References Cited

U.S. PATENT DOCUMENTS

| | | | |
|---|---|---|---|
| 3,176,840 A | 4/1965 | Bickel | |
| 4,043,562 A | 8/1977 | Shillington | |
| 4,181,948 A | 1/1980 | Jackson et al. | |
| 4,230,031 A | 10/1980 | Pedroso et al. | |
| 4,248,389 A | 2/1981 | Thompson et al. | |
| 4,257,272 A | 3/1981 | Sloman | |
| 4,365,634 A | 12/1982 | Bare et al. | |
| 4,393,584 A | 7/1983 | Bare et al. | |
| 4,452,358 A | 6/1984 | Simpson | |
| 4,454,944 A | 6/1984 | Shillington et al. | |
| 4,502,606 A | 3/1985 | Shillington et al. | |
| 4,522,211 A | 6/1985 | Bare et al. | |
| 4,554,077 A | 11/1985 | Brown et al. | |
| 4,579,053 A | 4/1986 | Beesley et al. | |

(Continued)

OTHER PUBLICATIONS

Quinn, Paul. "How the Waste was Won." *Supply & Chain System* (Dec. 1997): 4 pp. Online. Internet. Oct. 26, 2004.

(Continued)

*Primary Examiner*—John G. Weiss
*Assistant Examiner*—Matthew L. Brooks
(74) *Attorney, Agent, or Firm*—Knobbe, Martens, Olson & Bear, LLP

(57) ABSTRACT

A system for disposing of medical waste is generally configured to sort waste items into a plurality of disposable containers according to applicable rules and regulations governing the handling and/or disposal of such items. In some embodiments, a system comprises sorting stations, each of which houses a number of disposable containers. Each station can identify an item of waste, determine the most appropriate container for the item, and facilitate disposal of the item in the appropriate container.

13 Claims, 36 Drawing Sheets

U.S. PATENT DOCUMENTS

| | | |
|---|---|---|
| 4,600,112 A | 7/1986 | Shillington et al. |
| 4,605,124 A | 8/1986 | Sandel et al. |
| 4,667,821 A | 5/1987 | Shillington |
| 4,670,634 A | 6/1987 | Bridges et al. |
| 4,674,676 A | 6/1987 | Sandel et al. |
| 4,677,909 A | 7/1987 | Beesley et al. |
| 4,700,363 A | 10/1987 | Tomlinson et al. |
| 4,702,385 A | 10/1987 | Shillington et al. |
| 4,736,860 A | 4/1988 | Bemis |
| 4,750,437 A | 6/1988 | Rouse |
| 4,779,728 A | 10/1988 | Hanifl et al. |
| 4,785,969 A | 11/1988 | McLaughlin |
| 4,802,423 A | 2/1989 | Pennington |
| 4,804,090 A | 2/1989 | Schuh et al. |
| 4,809,850 A | 3/1989 | Laible et al. |
| 4,821,120 A | 4/1989 | Tomlinson |
| 4,842,138 A | 6/1989 | Sandel et al. |
| 4,844,252 A | 7/1989 | Barron et al. |
| 4,852,794 A | 8/1989 | Bennett et al. |
| 4,853,208 A | 8/1989 | Reimers et al. |
| 4,860,317 A | 8/1989 | Tomlinson |
| 4,919,086 A | 4/1990 | Shillington |
| 4,925,048 A | 5/1990 | Noack |
| 4,950,105 A | 8/1990 | Meess et al. |
| 4,972,950 A | 11/1990 | Shillington |
| 4,984,686 A | 1/1991 | Shillington et al. |
| 5,005,532 A | 4/1991 | Shillington et al. |
| 5,005,793 A | 4/1991 | Shillington et al. |
| 5,014,875 A | 5/1991 | McLaughlin et al. |
| 5,022,548 A | 6/1991 | Stakis |
| 5,024,326 A | 6/1991 | Sandel et al. |
| 5,024,327 A | 6/1991 | Shillington |
| 5,035,858 A | 7/1991 | Held et al. |
| 5,036,866 A | 8/1991 | Eldrige, Jr. et al. |
| 5,046,614 A | 9/1991 | Torres et al. |
| 5,048,766 A | 9/1991 | Gaylor et al. |
| 5,058,764 A | 10/1991 | Gaba |
| 5,064,124 A | 11/1991 | Chang |
| 5,072,832 A | 12/1991 | Valentine et al. |
| 5,076,429 A | 12/1991 | Patrick et al. |
| 5,080,251 A | 1/1992 | Noack |
| 5,097,950 A | 3/1992 | Weiss et al. |
| 5,103,997 A | 4/1992 | Shillington et al. |
| 5,106,594 A | 4/1992 | Held et al. |
| 5,107,990 A | 4/1992 | Wicherski et al. |
| 5,124,125 A | 6/1992 | Brent |
| 5,125,995 A | 6/1992 | D'Haese et al. |
| 5,145,063 A | 9/1992 | Lee |
| 5,152,751 A | 10/1992 | Kozlowski |
| 5,154,345 A | 10/1992 | Shillington |
| 5,164,897 A | 11/1992 | Clark et al. |
| 5,167,193 A | 12/1992 | Withers et al. |
| 5,178,322 A | 1/1993 | Shillington |
| 5,184,720 A | 2/1993 | Packer et al. |
| 5,195,635 A | 3/1993 | Cornwell |
| 5,213,758 A | 5/1993 | Kawashima et al. |
| 5,226,065 A | 7/1993 | Held et al. |
| 5,230,496 A | 7/1993 | Shillington et al. |
| 5,231,938 A | 8/1993 | Gore |
| 5,240,108 A | 8/1993 | Tonna |
| 5,249,680 A | 10/1993 | Shillington |
| 5,256,861 A | 10/1993 | Anthony |
| 5,257,577 A | 11/1993 | Clark |
| 5,265,724 A | 11/1993 | Dondlinger |
| 5,271,892 A | 12/1993 | Hanson et al. |
| 5,276,253 A | 1/1994 | Circeo, Jr. et al. |
| 5,277,869 A | 1/1994 | Glazer et al. |
| 5,281,391 A | 1/1994 | Hanson et al. |
| 5,295,582 A | 3/1994 | Dan |
| 5,312,429 A | 5/1994 | Noack |
| 5,322,603 A | 6/1994 | Kameda et al. |
| 5,323,994 A | 6/1994 | Shillington et al. |
| 5,330,448 A | 7/1994 | Chu |
| 5,339,955 A | 8/1994 | Horan et al. |
| 5,350,562 A | 9/1994 | Anthony |
| 5,354,000 A | 10/1994 | Wright et al. |
| 5,363,958 A | 11/1994 | Horan |
| 5,372,725 A | 12/1994 | Halff et al. |
| 5,384,092 A | 1/1995 | Sawhill et al. |
| 5,385,105 A | 1/1995 | Withers, Jr. et al. |
| 5,389,084 A | 2/1995 | Horan et al. |
| 5,395,008 A | 3/1995 | Bemis et al. |
| 5,395,338 A | 3/1995 | Gaba |
| 5,397,068 A | 3/1995 | Solomons et al. |
| 5,397,535 A | 3/1995 | Kaneko |
| 5,401,444 A | 3/1995 | Spinello |
| 5,402,887 A | 4/1995 | Shillington |
| 5,413,243 A | 5/1995 | Bemis et al. |
| 5,415,180 A | 5/1995 | Horan |
| 5,415,315 A * | 5/1995 | Ramirez ................ 220/345.2 |
| 5,417,659 A | 5/1995 | Gaba |
| 5,419,435 A | 5/1995 | Perzan et al. |
| 5,421,672 A | 6/1995 | Ankeny et al. |
| 5,423,450 A | 6/1995 | Shillington et al. |
| 5,423,492 A | 6/1995 | Willis |
| 5,425,458 A | 6/1995 | Gilcreest et al. |
| 5,427,238 A | 6/1995 | Weiss |
| 5,427,737 A | 6/1995 | Glazer et al. |
| 5,433,412 A | 7/1995 | Watt et al. |
| 5,441,622 A | 8/1995 | Langford |
| 5,449,068 A | 9/1995 | Gharibian |
| 5,460,294 A | 10/1995 | Williams |
| 5,465,461 A | 11/1995 | Sandel |
| 5,465,841 A | 11/1995 | Wilson et al. |
| 5,469,600 A | 11/1995 | Sandel |
| 5,470,022 A | 11/1995 | Wright et al. |
| 5,471,705 A | 12/1995 | Dao |
| 5,472,167 A | 12/1995 | Shillington et al. |
| 5,474,181 A | 12/1995 | Shillington et al. |
| 5,476,634 A | 12/1995 | Bridges et al. |
| 5,493,757 A | 2/1996 | Horan et al. |
| 5,494,186 A | 2/1996 | Marsh |
| 5,495,941 A | 3/1996 | Leonard |
| 5,507,408 A | 4/1996 | Mosior et al. |
| 5,508,004 A | 4/1996 | Held et al. |
| 5,508,912 A | 4/1996 | Schneiderman |
| 5,511,908 A | 4/1996 | Van Valkenburgh et al. |
| 5,519,931 A | 5/1996 | Reich |
| 5,520,282 A | 5/1996 | Williams, Jr. |
| 5,520,450 A | 5/1996 | Colson, Jr. et al. |
| 5,527,329 A | 6/1996 | Gharibian |
| 5,533,974 A | 7/1996 | Gaba |
| 5,536,898 A | 7/1996 | Conner et al. |
| 5,536,945 A | 7/1996 | Reich |
| 5,538,132 A | 7/1996 | Propp et al. |
| 5,568,871 A | 10/1996 | Shantzis |
| 5,570,783 A | 11/1996 | Thorne et al. |
| 5,573,113 A | 11/1996 | Shillington et al. |
| 5,573,529 A | 11/1996 | Haak et al. |
| 5,582,793 A | 12/1996 | Glazer et al. |
| 5,584,302 A | 12/1996 | Sillaway et al. |
| 5,587,572 A | 12/1996 | Kirby |
| 5,605,245 A | 2/1997 | Bemis et al. |
| 5,616,136 A | 4/1997 | Shillington et al. |
| 5,626,240 A | 5/1997 | Friedrichs et al. |
| 5,630,506 A | 5/1997 | Thorne et al. |
| 5,637,101 A | 6/1997 | Shillington |
| 5,639,031 A | 6/1997 | Wright et al. |
| 5,641,423 A | 6/1997 | Bridges et al. |
| 5,647,502 A | 7/1997 | Marsh |
| 5,661,978 A | 9/1997 | Holmes et al. |
| 5,664,112 A | 9/1997 | Sturgeon et al. |
| 5,667,069 A | 9/1997 | Williams, Jr. |
| 5,669,102 A | 9/1997 | Sandel |

| Patent | Date | Name |
|---|---|---|
| 5,672,883 A | 9/1997 | Reich |
| 5,676,255 A | 10/1997 | Flowers |
| 5,678,568 A | 10/1997 | Uchikubo et al. |
| 5,688,399 A | 11/1997 | Halff et al. |
| 5,693,028 A | 12/1997 | Shillington |
| 5,709,842 A | 1/1998 | Held et al. |
| 5,712,990 A | 1/1998 | Henderson |
| 5,716,114 A | 2/1998 | Holmes et al. |
| 5,725,993 A | 3/1998 | Bringley et al. |
| 5,726,884 A | 3/1998 | Sturgeon et al. |
| 5,735,639 A | 4/1998 | Payne et al. |
| 5,752,234 A | 5/1998 | Withers |
| 5,755,698 A | 5/1998 | Kagan et al. |
| 5,772,059 A | 6/1998 | McCord |
| 5,785,591 A | 7/1998 | Payne |
| 5,794,789 A | 8/1998 | Payson et al. |
| 5,829,588 A | 11/1998 | Bloomfield |
| 5,830,419 A | 11/1998 | Held et al. |
| 5,833,683 A | 11/1998 | Fuller et al. |
| 5,833,922 A | 11/1998 | Held et al. |
| 5,836,989 A | 11/1998 | Shelton |
| 5,837,171 A | 11/1998 | Danzik et al. |
| 5,842,652 A | 12/1998 | Warsing et al. |
| 5,842,976 A | 12/1998 | Williamson |
| 5,845,255 A | 12/1998 | Mayaud |
| 5,848,593 A | 12/1998 | McGrady et al. |
| 5,848,692 A | 12/1998 | Thorne et al. |
| 5,857,993 A | 1/1999 | Atanasoska et al. |
| 5,862,530 A | 1/1999 | Shillington |
| 5,883,806 A | 3/1999 | Meador et al. |
| 5,912,818 A | 6/1999 | McGrady et al. |
| 5,916,202 A | 6/1999 | Haswell |
| 5,923,001 A | 7/1999 | Morris et al. |
| 5,933,809 A | 8/1999 | Hunt et al. |
| 5,940,306 A | 8/1999 | Gardner et al. |
| 5,941,385 A | 8/1999 | Barton |
| 5,947,285 A | 9/1999 | Gaba et al. |
| 5,947,950 A | 9/1999 | Shillington et al. |
| 5,958,241 A | 9/1999 | DeBenedetto et al. |
| 5,965,858 A | 10/1999 | Suzuki et al. |
| 5,991,728 A | 11/1999 | DeBusk |
| 5,993,046 A | 11/1999 | McGrady et al. |
| 6,003,006 A | 12/1999 | Colella et al. |
| 6,010,444 A | 1/2000 | Honeycutt et al. |
| 6,021,392 A | 2/2000 | Lester et al. |
| 6,021,920 A | 2/2000 | Aldape |
| 6,024,216 A | 2/2000 | Shillington et al. |
| 6,027,490 A | 2/2000 | Radford et al. |
| 6,062,001 A | 5/2000 | Kunik |
| 6,065,819 A | 5/2000 | Holmes et al. |
| 6,066,243 A | 5/2000 | Anderson et al. |
| 6,097,995 A | 8/2000 | Tipton |
| 6,109,774 A | 8/2000 | Holmes et al. |
| 6,110,848 A | 8/2000 | Bouchette |
| 6,112,502 A | 9/2000 | Frederick et al. |
| 6,116,461 A | 9/2000 | Broadfield et al. |
| 6,119,869 A | 9/2000 | Geiman |
| 6,204,056 B1 | 3/2001 | Barnes et al. |
| 6,226,214 B1 | 5/2001 | Choi |
| 6,226,617 B1 | 5/2001 | Suzuki et al. |
| 6,247,592 B1 | 6/2001 | Racicot et al. |
| 6,250,465 B1 | 6/2001 | Daniels et al. |
| 6,253,916 B1 | 7/2001 | Bickel |
| 6,315,113 B1 | 11/2001 | Britton et al. |
| 6,338,007 B1 | 1/2002 | Broadfield et al. |
| 6,339,732 B1 | 1/2002 | Phoon et al. |
| 6,341,287 B1 | 1/2002 | Sziklai et al. |
| 6,344,638 B1 | 2/2002 | Tomasello |
| 6,361,263 B1 | 3/2002 | Dewey et al. |
| 6,367,377 B1 | 4/2002 | Gawley et al. |
| 6,386,386 B1 | 5/2002 | George |
| 6,397,115 B1 | 5/2002 | Basden |
| 6,425,487 B1 | 7/2002 | Emmott et al. |
| 6,474,472 B1 | 11/2002 | Shaw |
| 6,488,675 B1 | 12/2002 | Radford et al. |
| 6,499,270 B1 | 12/2002 | Peroni et al. |
| 6,542,902 B1 | 4/2003 | Dulong et al. |
| 6,558,077 B1 | 5/2003 | Colson |
| 6,576,918 B1 | 6/2003 | Fu et al. |
| 6,581,204 B1 | 6/2003 | Busk |
| 6,601,772 B1 | 8/2003 | Rubin et al. |
| 6,633,795 B1 | 10/2003 | Suzuki et al. |
| 6,663,004 B1 * | 12/2003 | Wagner et al. ............... 235/385 |
| 6,701,345 B1 | 3/2004 | Carley et al. |
| 6,712,561 B1 | 3/2004 | Valerino, Sr. et al. |
| 6,727,294 B1 | 4/2004 | Kanayama et al. |
| 6,730,059 B1 | 5/2004 | Caizza et al. |
| 6,748,400 B1 | 6/2004 | Quick |
| 6,753,454 B1 | 6/2004 | Mello et al. |
| 6,759,959 B1 | 7/2004 | Wildman |
| 6,779,816 B1 | 8/2004 | Williams |
| 6,788,997 B1 | 9/2004 | Frederick |
| 6,799,725 B1 | 10/2004 | Hess |
| 6,830,197 B1 | 12/2004 | Rubin et al. |
| 2001/0026359 A1 * | 10/2001 | Raymond ................... 355/75 |
| 2003/0004965 A1 | 1/2003 | Farmer et al. |
| 2003/0034391 A1 | 2/2003 | Wagner et al. |
| 2003/0131011 A1 | 7/2003 | Haunschild et al. |
| 2003/0139640 A1 | 7/2003 | Whittacre et al. |
| 2004/0111179 A1 | 6/2004 | Broadfield et al. |
| 2004/0112960 A1 | 6/2004 | Wagner et al. |
| 2004/0195308 A1 | 10/2004 | Wagner et al. |
| 2004/0195309 A1 | 10/2004 | Wagner et al. |
| 2004/0199401 A1 | 10/2004 | Wagner et al. |
| 2004/0199545 A1 | 10/2004 | Wagner et al. |
| 2004/0204867 A1 | 10/2004 | Smith et al. |
| 2004/0205343 A1 | 10/2004 | Forth et al. |
| 2004/0243444 A1 | 12/2004 | Steusloff et al. |

OTHER PUBLICATIONS

Daughton, Christian G. "Cradle-to-Cradle Stewardship of Drugs for Minimizing Their Environmental Disposition While Promoting Human Health II. Drug Disposal, Waster Reduction, and Future Directions." *Environmental Health Perspectives.* vol. 111, No. 5, May 2003.

Townsend, Mark. "Stay calm everyone, there's Prozac in the drinking water." *The Observer.* Aug. 8, 2004.

Daughton, G. Christian. "I. PPCPs as Environmental Pollutants. II. Pharmaceuticals and Personal Care Products in the Environment: Overarching Issues and Overview." *U.S. Environmental Protection Agency, National Exposure Research Laboratory Environmental Sciences.*

Kuspis DA, Krenzelok EP. "What happens to expired medications? A survey of community medication disposal." *Vet Hum Toxicol.* Feb. 1996; 38(1):48-9.

*DEO Environmental Policy and Guidance.* Posted Sep. 2000.

Letter dated Aug. 27, 2004 from Andy D. Kublak, Regulatory Services Unit, Division of Hazardous Waste Management to Mr. Alan Davidner, President of Vesta Medical.

Shafer, Mariana. "Development of a Novel Disinfectant and Mechanical-Chemical Process for Disinfection of Biomedical Waste" Thesis of Master of Science, Graduate Department of Microbiology, University of Toronto, © 1996.

Walker, Richard E. "State of Art Study of Hospital Wastes" *Journal of Hazardous Materials,* V. 24, Nos. 2-3, Sep. 1990, pp. 301-302.

Cross Jr., Frank L., P.E. "Siling a Medical Waste Treatment Facility" *Pollution Engineering,* V. 22, No. 9, Sep. 1990. pp. 68-73.

"Stericycle, Inc.: Recycling Potentially Infectious Waste." *Healthcare Hazardous Material Management,* Jul. 1992, pp. 7-10.

Yasmeen, Farhana et al. "Recycling of Medical Plastic Wastes" *Popular Plastic and Packaging,* V. 47, No. 4, Apr. 2002, pp. 71-74.

Humber, H. "Recycling Plastics in Medical Wastes" *Biomedical Wastes Systems, Inc.*, Davos Recycle '93 International Forum and Exposition, Davos, Switzerland, Mar. 22-26, 1993.

Slavik, N.S. "Infectious Waste Management: Strategies for the Health Care Facility" *Compliance Resources, Inc.*, 1990 Polymers, Laminations & Coatings Conference Proceedings, Boston, MA., Sep. 4-7, 1990, pp. 37-39.

US 6,019,218, 02/2000, Racicot et al. (withdrawn)

* cited by examiner

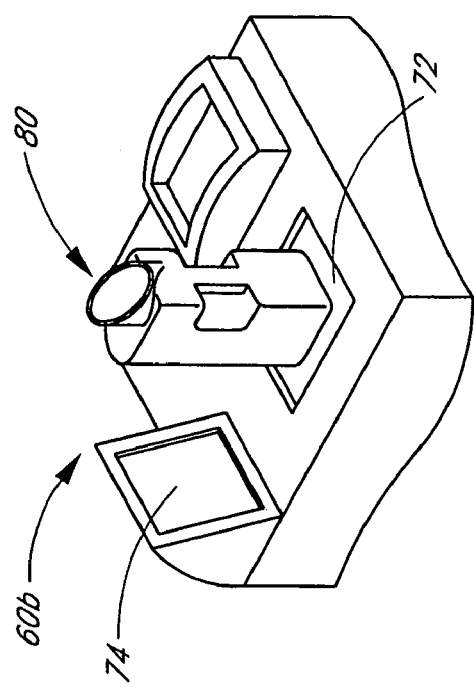
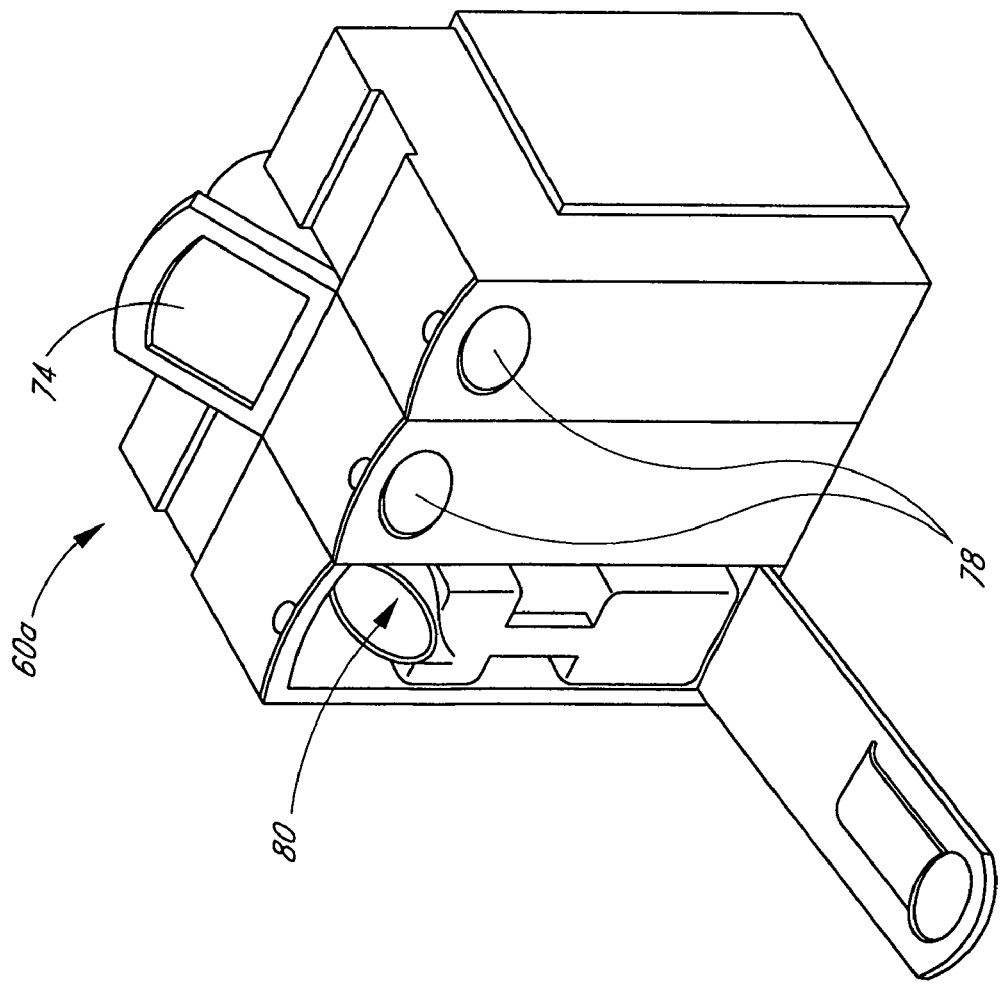
FIG. 4
FIG. 3

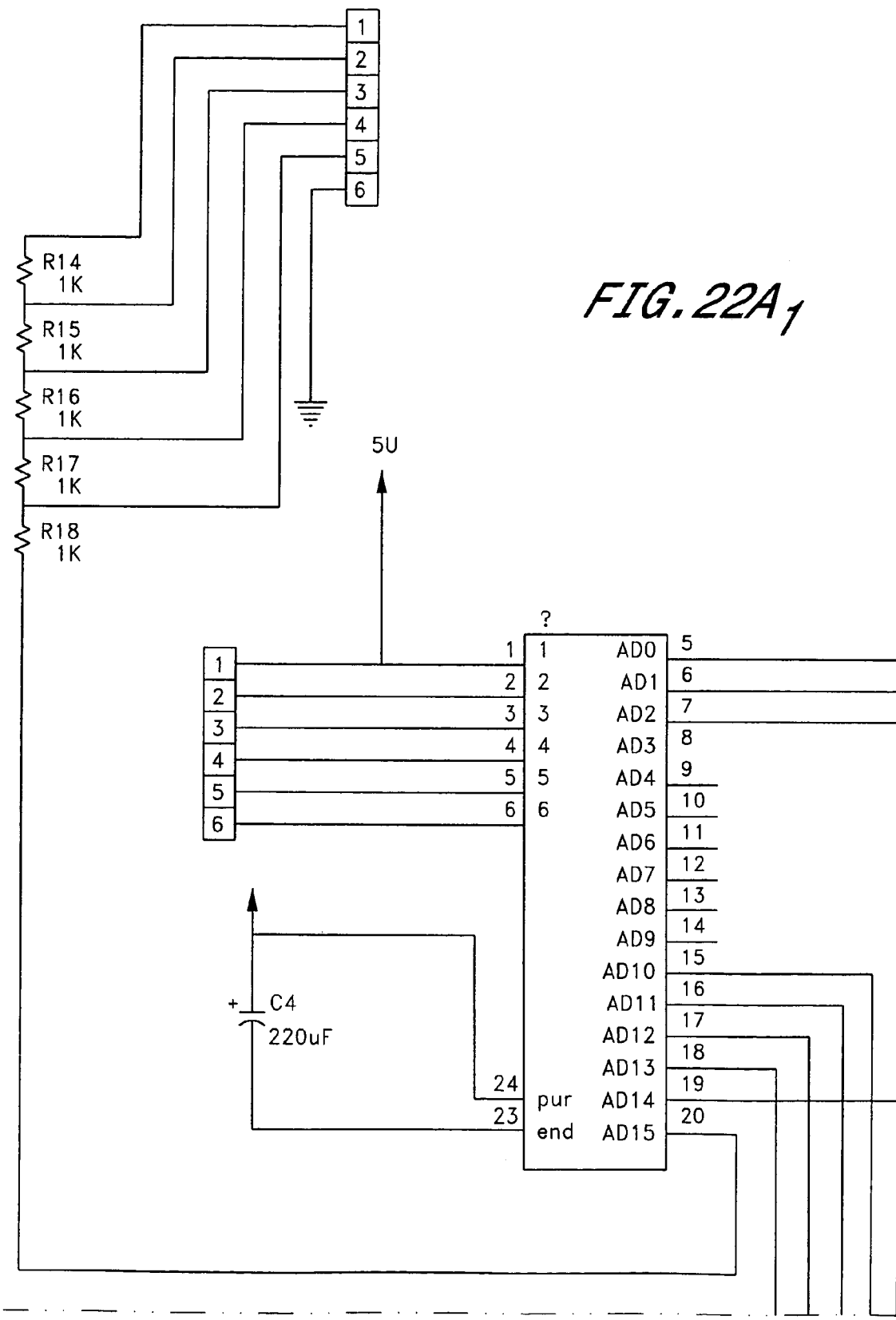
FIG. 22A₁

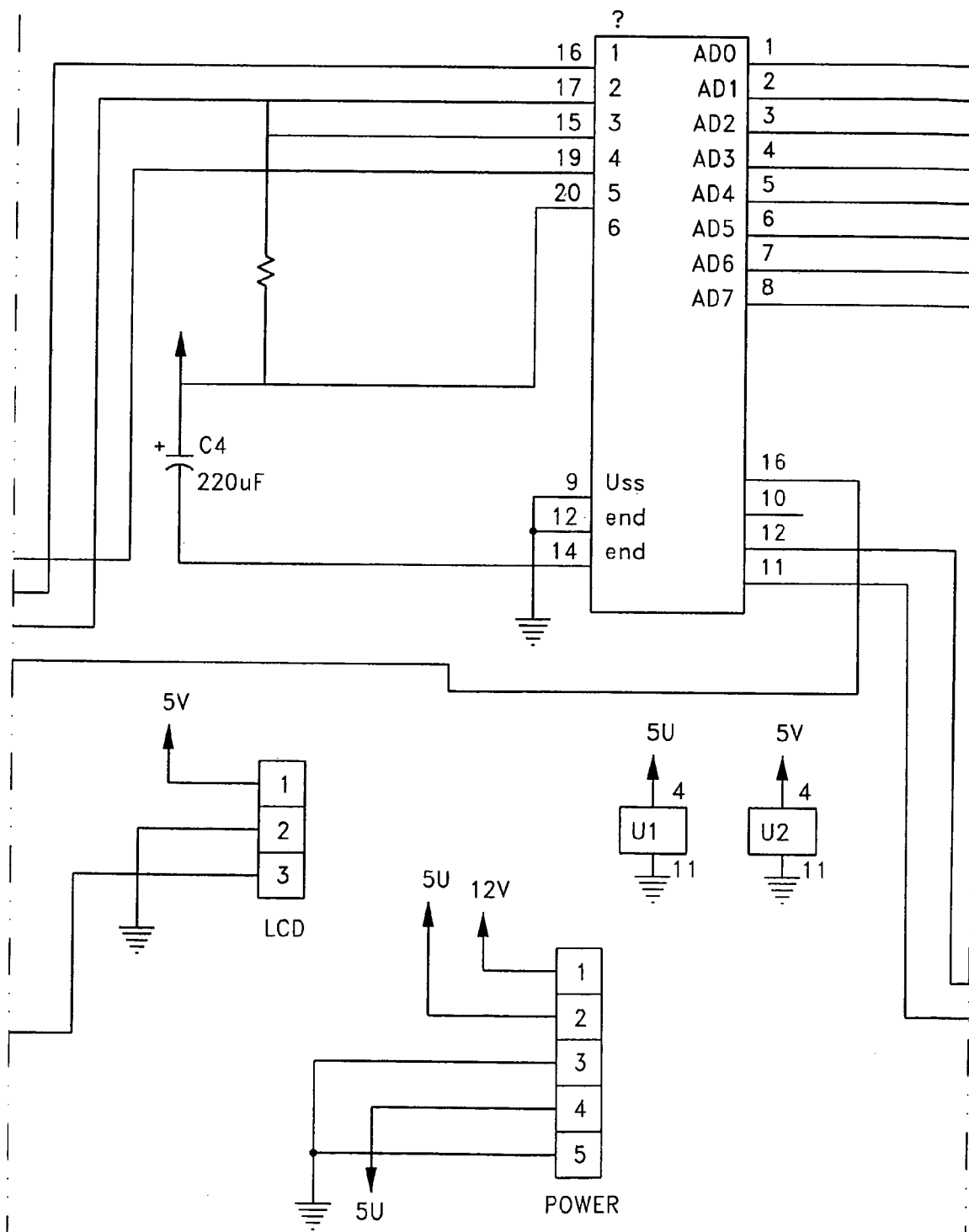
FIG.22A₂

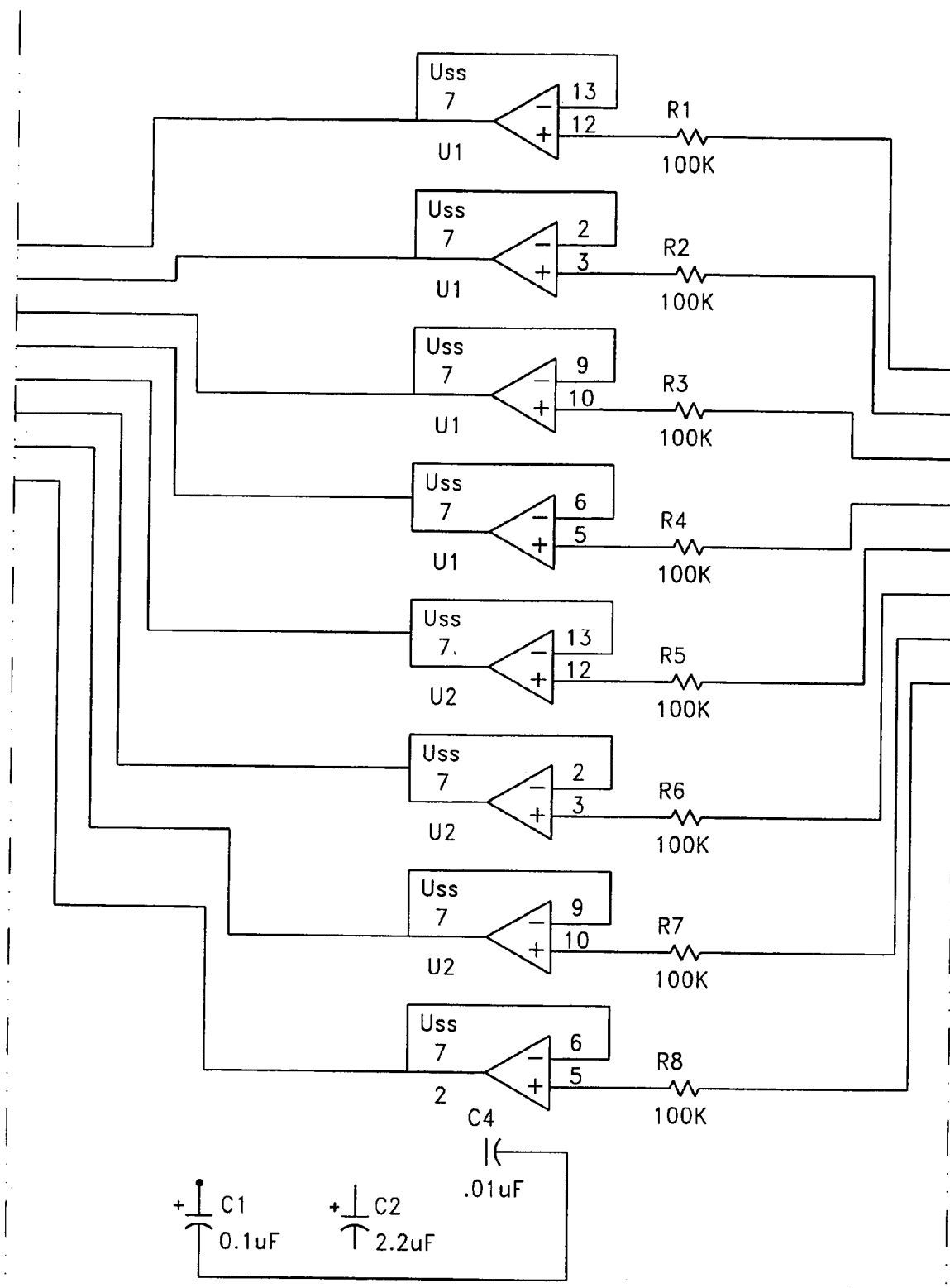
FIG.22A₃

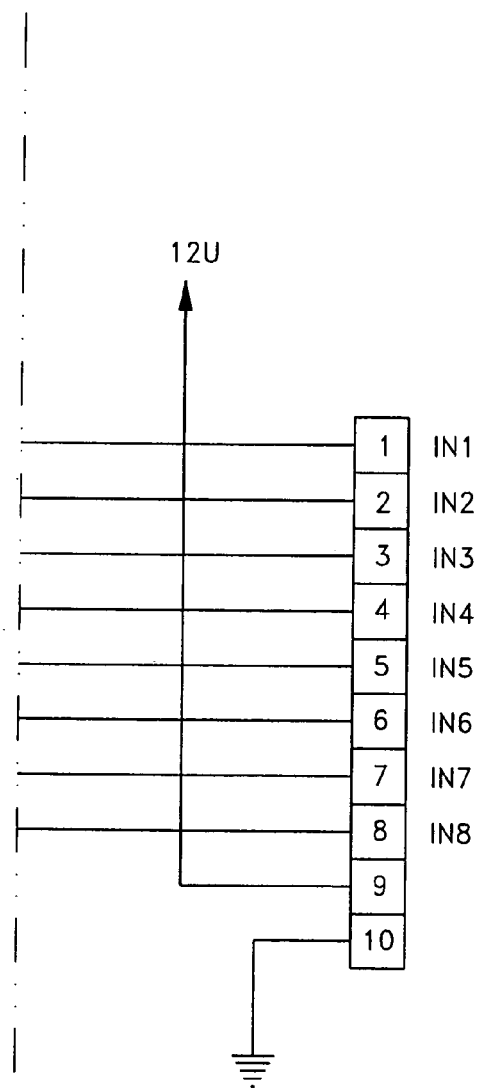
FIG. 22A₄

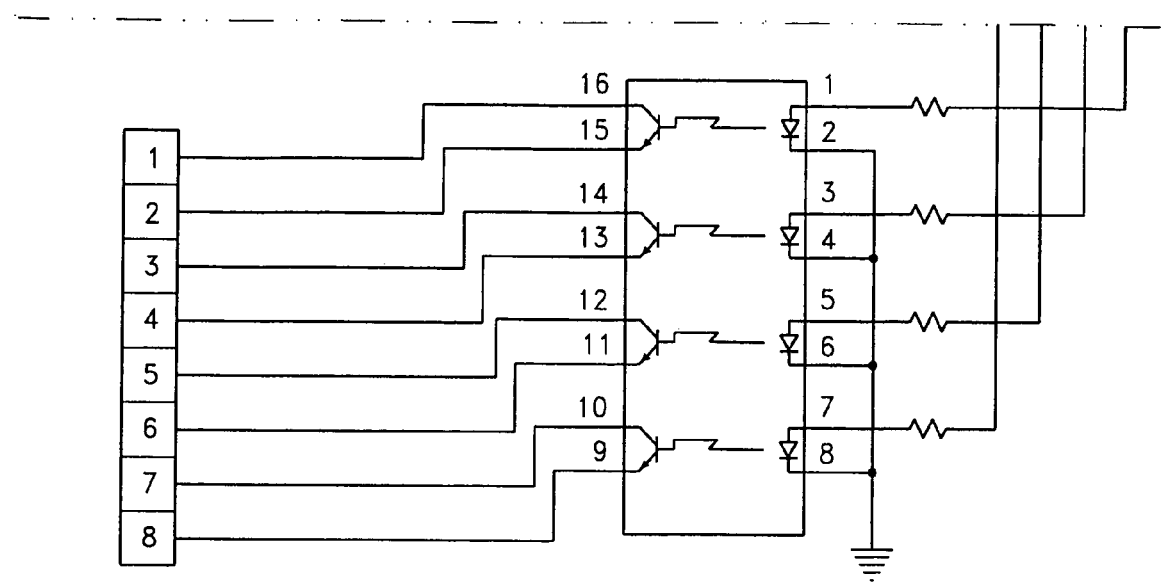
FIG.22A₅

FIG. 23A

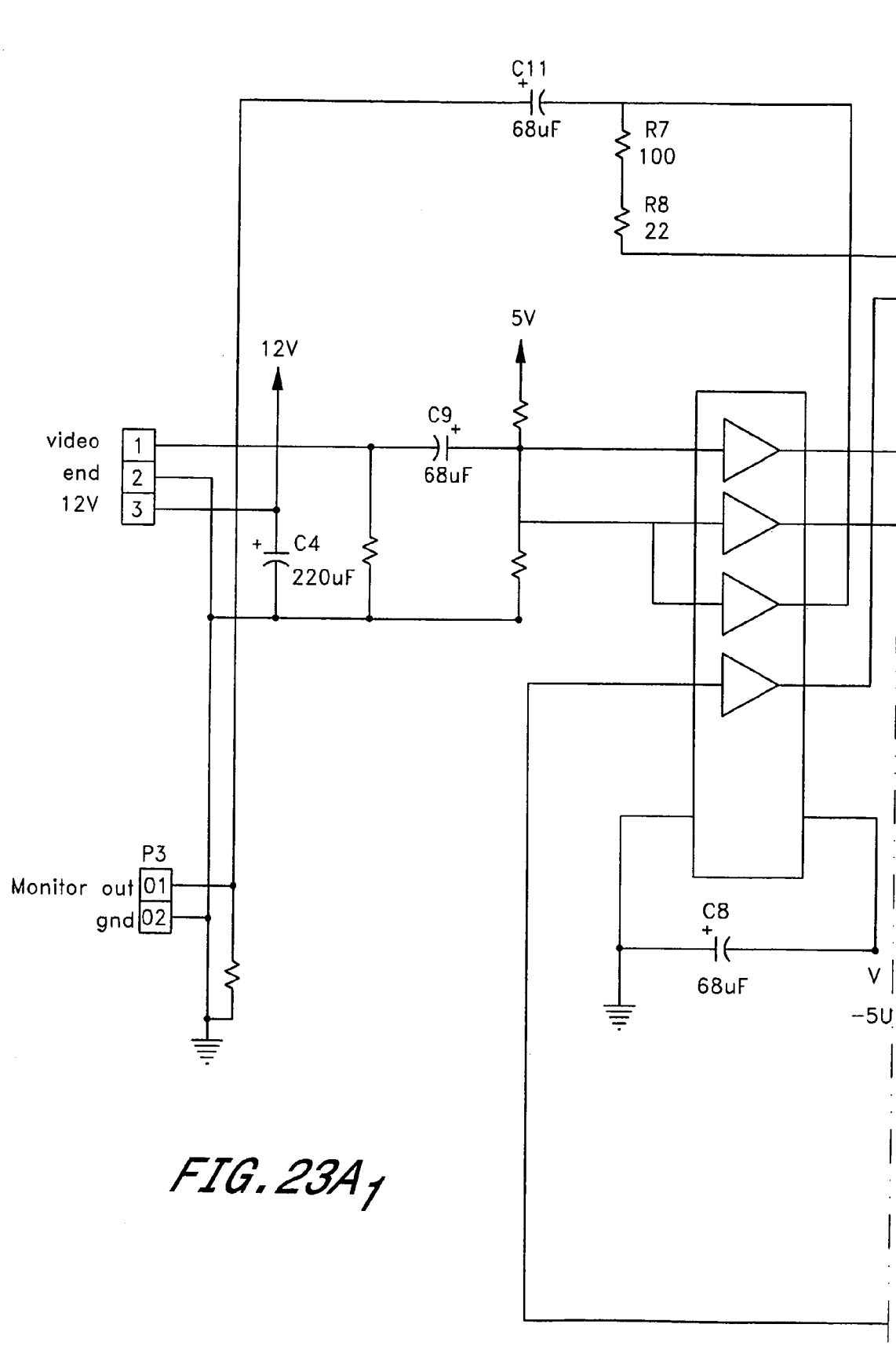
FIG. 23A₁

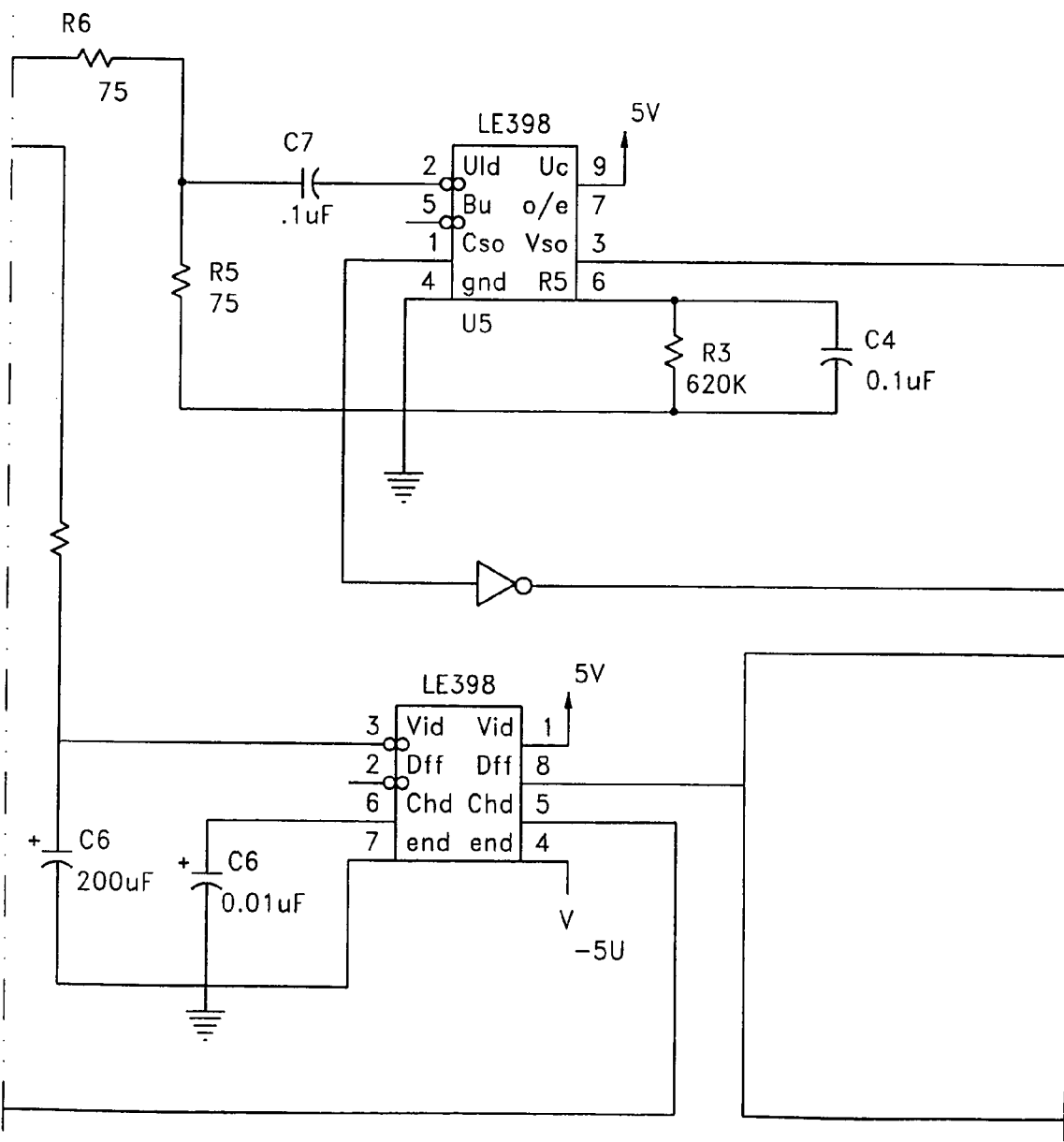
FIG. 23A₂

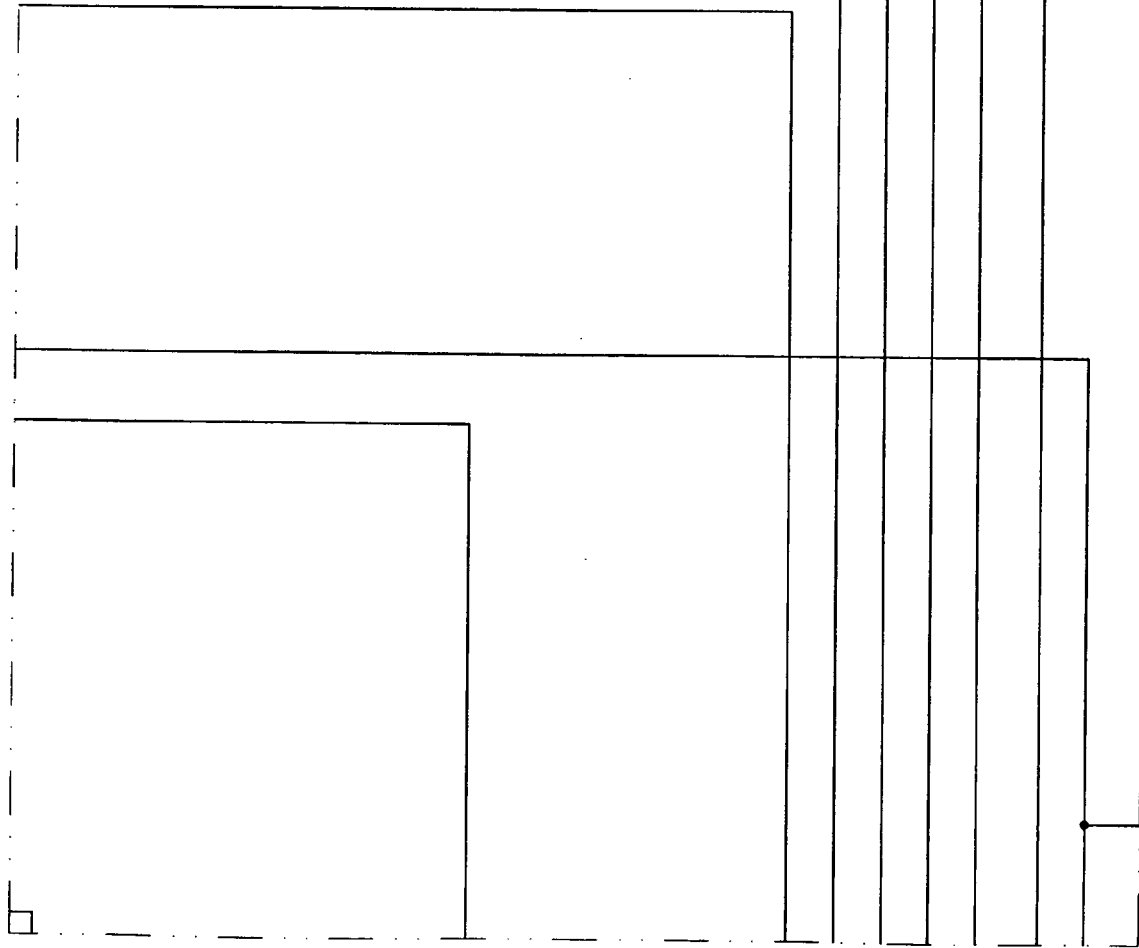
FIG.23A₃

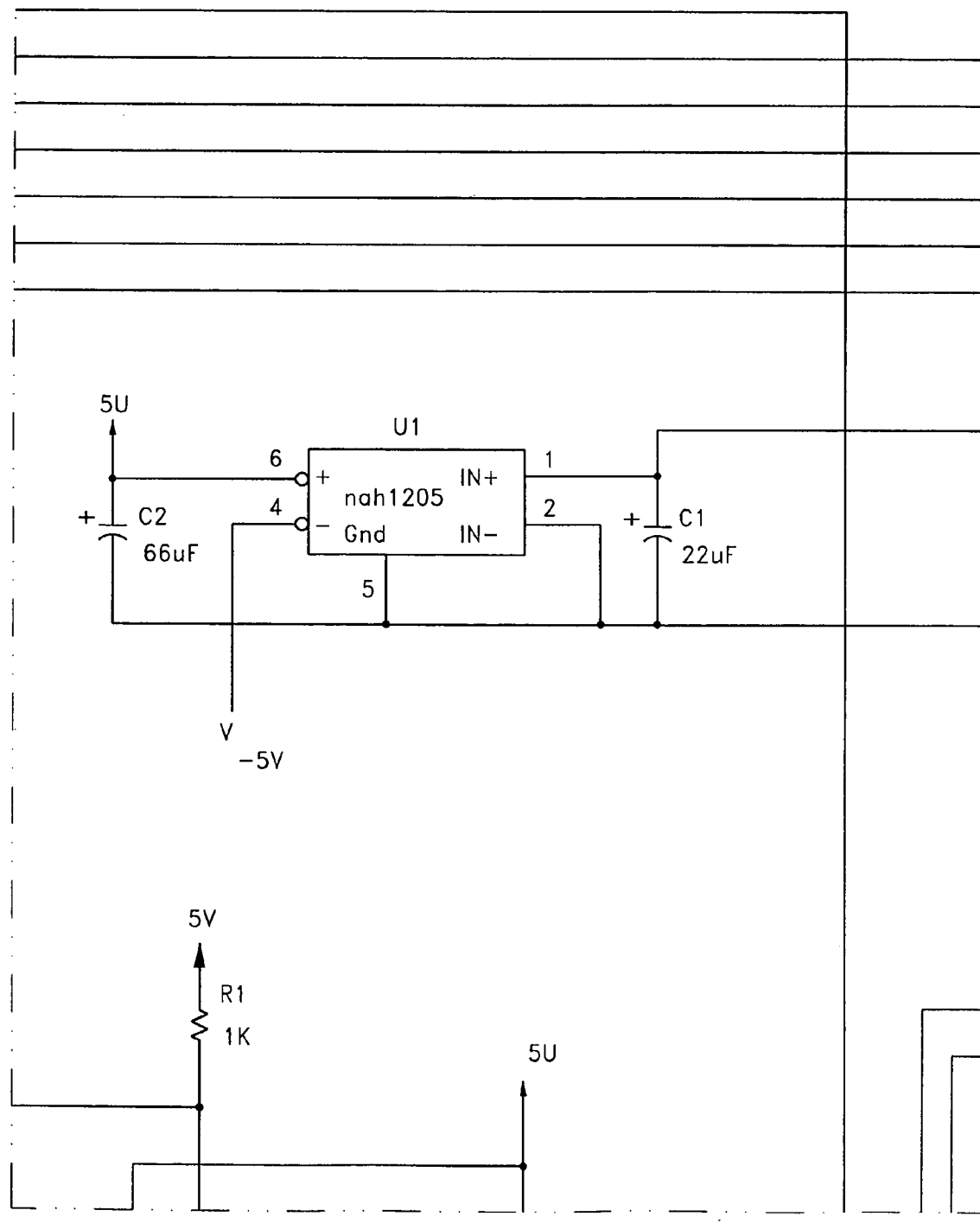
FIG.23A₄

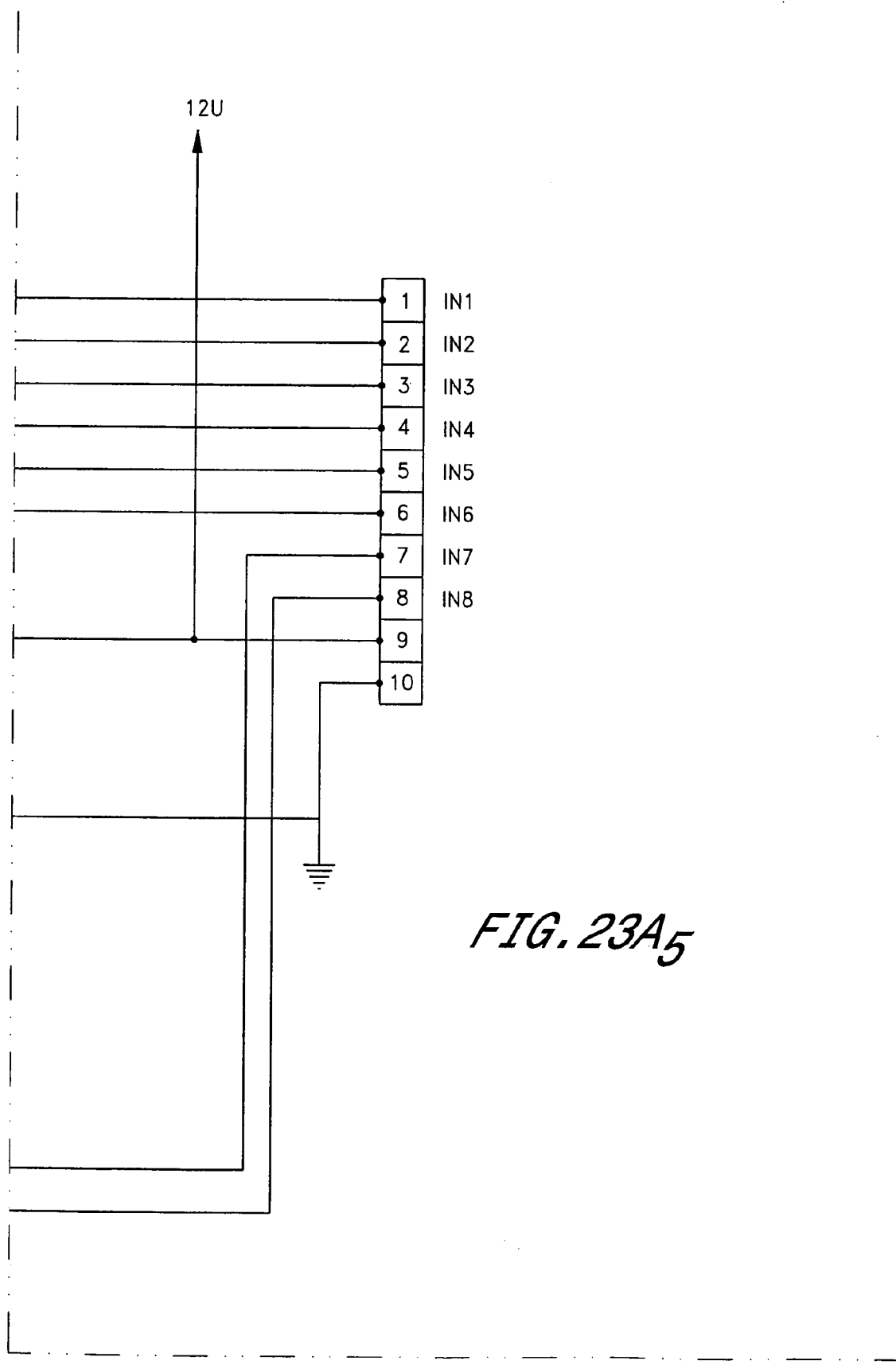
FIG. 23A₅

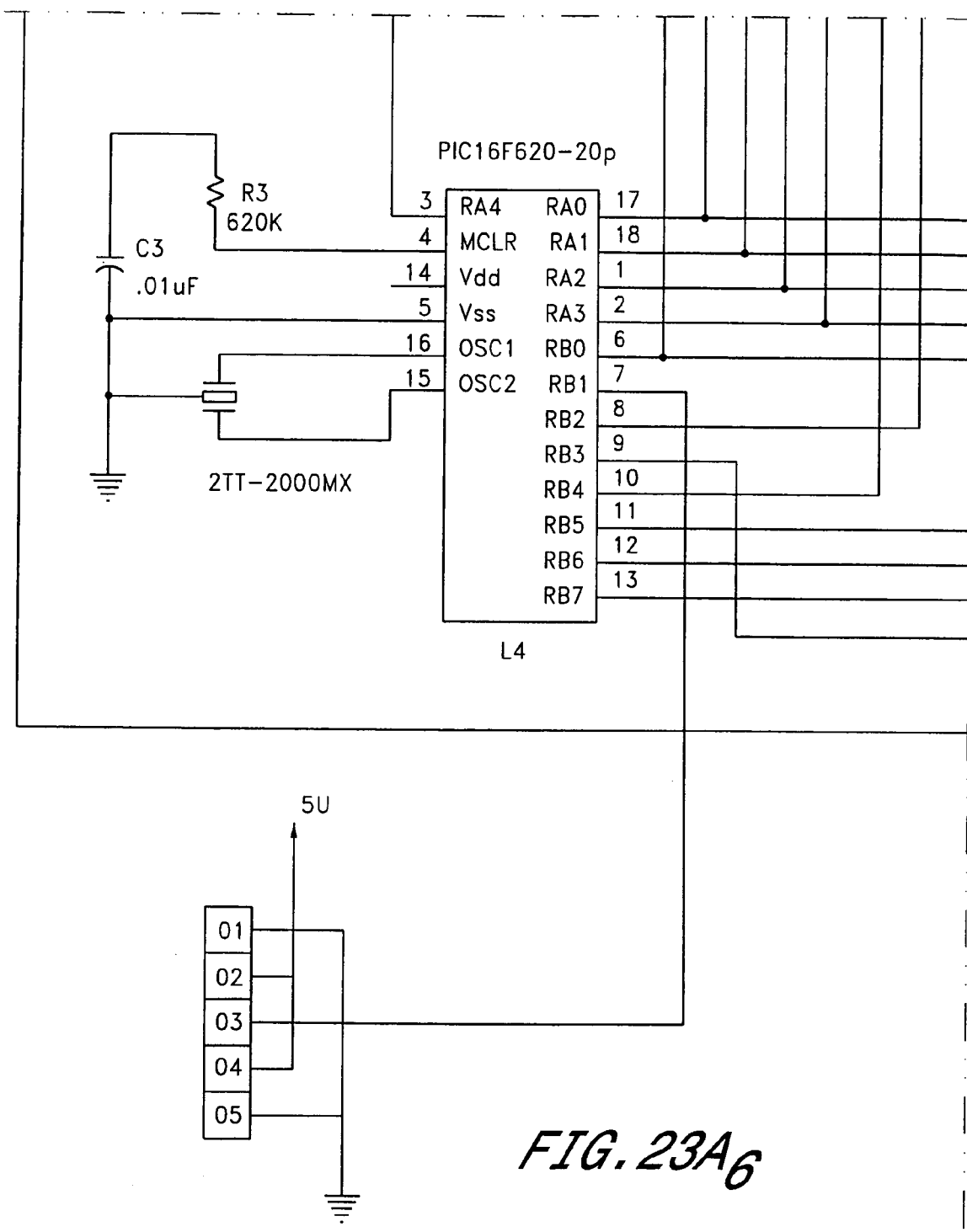
FIG. 23A₆

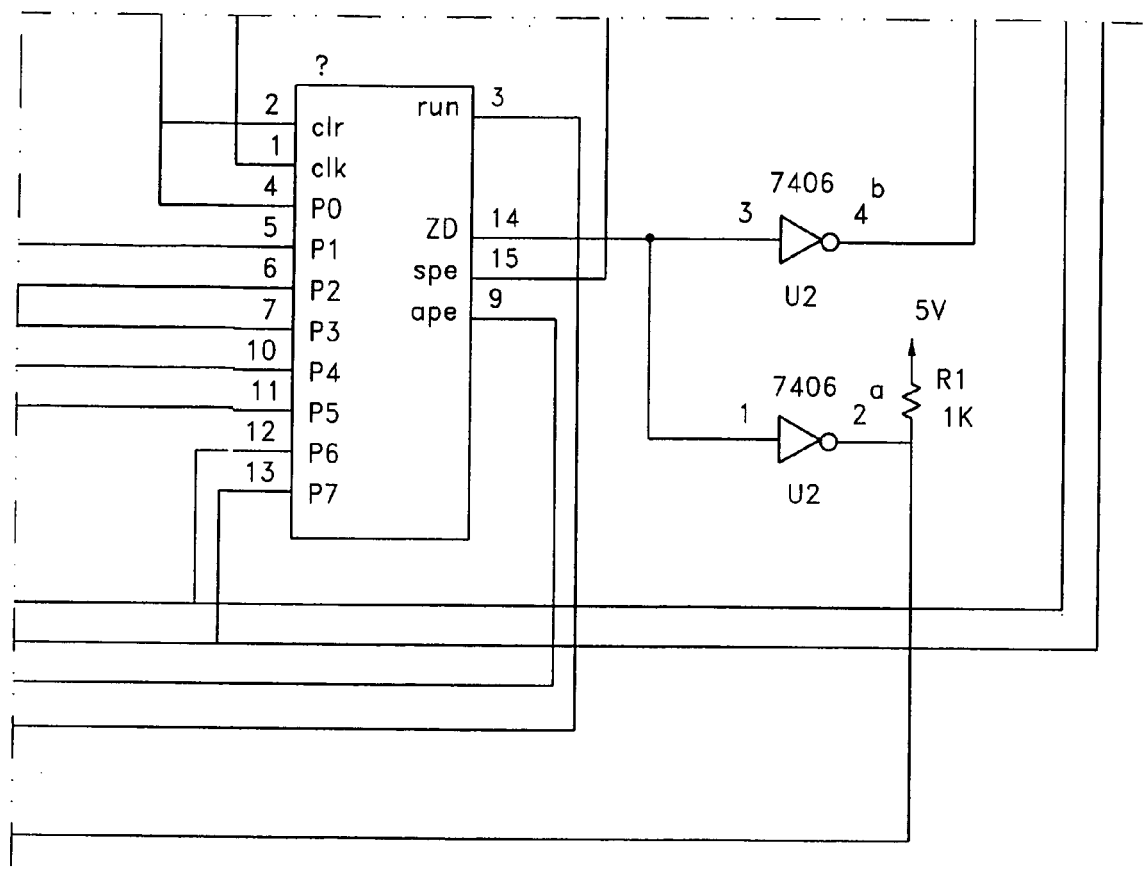
FIG.23A7

WASTE CONTAINER IDENTIFICATION SYSTEM

RELATED APPLICATIONS

This is a continuation of U.S. patent application Ser. No. 10/945,223, titled SYSTEM AND METHOD FOR SORTING MEDICAL WASTE FOR DISPOSAL, and filed on Sep. 20, 2004, which claims the benefit of U.S. Provisional Patent Applications Ser. No. 60/504,170 filed Sep. 19, 2003 and Ser. No. 60/589,118, filed Jul. 19, 2004, all of which are incorporated by reference herein in their entireties.

BACKGROUND

1. Field of the Invention

The invention relates in general to the field of waste disposal systems, and in particular to a system for sorting medical waste for disposal.

2. Description of the Related Art

The Environmental Protection Agency (EPA) enforces the Resource Conservation & Recovery Act (RCRA) which was enacted in 1976 in order to control the disposal of harmful or hazardous waste materials. There are currently over 100,000 drugs commercially available in the United States, of which about 14,000 are considered hazardous by RCRA requirements. A typical medium size hospital utilizes thousands of different drugs in a year of which hundreds are considered hazardous. The EPA is increasingly enforcing hospitals' compliance with the RCRA requirements because it has been shown in several studies that the 72 million pounds of pharmaceutical waste generated each year by hospitals is contributing to the pollution of groundwater and endocrine system damage in humans and other species. In addition, many organizations including Hospital for a Healthy Environment (H2E) and Joint Council for Accreditation of Healthcare Organizations (JCAHO) are pressing hospitals to be more environmentally friendly. In view of these changes, hospitals are increasing efforts to audit their own compliance with the laws. As a result, these hospitals are becoming more aware of the difficulty of sorting the numerous pharmaceutical waste streams that the EPA, Department of Transportation (DOT), Drug Enforcement Administration (DEA), and some states require.

More than 3.2 million tons of medical waste is generated by hospitals, medical clinics and pharmaceutical manufacturers each year. Half of this waste is considered infectious. Most of the infectious waste was treated in over 2400 incinerators throughout the country, until 1998 when the EPA began to enforce tough environmental emission laws that have reduced the number of incinerators to just over a hundred nationwide. Now much of the infectious waste is hauled to these remaining incinerators, often a substantial distance, or is treated by alternative technologies such as autoclaves and chemical processors. There is very little choice for hospitals because of the upfront cost and large footprint of the processing equipment. Although many companies have offered different kinds of equipment, the prices vary from a few hundred thousand dollars for smaller units to a few million for large units. Because of the long cycling times to decontaminate the waste, the equipment typically is very large in order to provide acceptable throughput. There are also several companies that provide a service to hospitals by utilizing chemical processors mounted on trucks. They go to a facility and decontaminate the infectious waste, allowing the treated waste to be hauled to a local landfill. There are concerns that this technology may not completely treat the waste in all circumstances and the chemical residue left after processing may remain an ecological issue.

Increasingly, hospitals are required to comply with the recent and projected enforcement of federal and state hazardous pharmaceutical waste regulations. Currently, clinicians must manually sort pharmaceutical waste streams into different colored containers for proper disposal of the separate waste streams. It is often not clear to a clinician which pharmaceuticals or waste materials are hazardous simply by looking at the container. Such confusion may lead to clinicians throwing hazardous drugs in non-hazardous containers such as sharps containers, infectious waste bags, non-hazardous pharmaceutical containers or simply down the drain.

SUMMARY OF THE INVENTION

There remains a need for a system for allowing clinicians to more easily sort medical waste items for appropriate disposal. There also remains a need for an automated system of waste disposal that encourages and facilitates hospital compliance with the relevant federal and state regulations.

Several embodiments of the present application describe systems and devices to sort and process infectious and pharmaceutical waste streams. Embodiments of a medical waste sorting system advantageously provide a labor savings for doctors, nurses and other clinicians by taking the bulk of the decision making associated with sorting medical waste away from the clinician. In one embodiment, a medical waste sorting system is provided, which will help clinicians conveniently comply with the recent and projected enforcement of federal and state hazardous waste laws. In some embodiments, the system can be configured to scan a bar code, RFID tag, or other system for identifying a spent drug. The spent drug can then be classified into an appropriate waste category, and a door can be automatically opened to provide access to a unique waste container for convenient disposal of the drug in compliance with applicable regulations.

According to another embodiment, a system is provided which will render infectious hospital or laboratory waste non-infectious. This embodiment will provide an economical service to a hospital by utilizing a self-contained truck-mounted version. Alternatively, a stand alone version can be made available for hospital purchase.

In another embodiment, a system for treating hazardous medical waste items in order to render them non-hazardous is provided.

In addition to the need for medical and pharmaceutical waste sorting, there exists a need to improve areas of water quality analysis and workplace safety. These areas include sampling water quality throughout the hospital to pinpoint inappropriate dumping of hazardous materials down the drain and improved programs that reduce hospital worker exposure to hazardous materials in the workplace.

In one embodiment, a system for sorting waste is provided. The system of this embodiment comprises a plurality of containers associated with a plurality of waste categories. A waste item identification device is configured to determine a qualitative parameter of an item of medical waste. A database is provided with medical waste item classification information. A control system is programmed to compare the qualitative parameter of the waste item to information contained in the database in order to assign the item to a medical waste category. The system also includes a sorting mechanism configured to place the item into one of the containers based on the medical waste category.

In another embodiment, a system for sorting waste comprises a waste item identification means for identifying a qualitative parameter of an item of medical waste, and a database means for classifying medical waste items into categories according to rules and regulations affecting the disposal of medical waste items. The system also includes control means for comparing the qualitative parameter of the waste item to information contained in the database, and for assigning the item to a unique medical waste category. A sorting means is also provided for placing the item into a container associated with the waste category.

In another embodiment, a system for determining the level of contents within a waste container is provided. The system of this embodiment comprises a plurality of containers, each one being associated with at least one of a plurality of a waste categories. Waste is placed in the containers based on a determination by a database that comprises medical waste classification information. At least one optical source is positioned on one side of at least one of the containers, and at least one optical detector is positioned on an opposite side of at least one of the containers. A processor is configured to determine a level of contents of a container by analysis of the data received from the optical detector.

Another embodiment of a system for determining the level of contents within a container comprises a means for containing waste items comprising a plurality of containers, and a means for producing an optical signal on one side of at least one of the plurality of containers. A means for receiving an optical signal is positioned on an opposite side of at least one of the containers, and means for processing signals from the respective means for producing and means for receiving is configured to determine a level of contents within at least one of the containers.

In another embodiment, a system comprises a container for storing sorted waste and a sensor configured to measure a presence of waste within the container without physically contacting the container. In another embodiment, a system comprises a means for storing sorted waste and a means for determining a quantity of waste within the container.

In another embodiment, a disposable container for use in a medical waste system comprises a plurality of walls defining an internal space and an opening configured to provide access to the internal space. An automatically operable door is configured to selectively occlude and reveal the opening, and the door is configured to be operated by a machine in which the container is placed. A machine-readable identification key is provided on at least a portion of the container. The machine-readable identification key bears a container type which defines a category of waste to be placed in the container.

In another embodiment, a disposable container for use in a medical waste system comprises a plurality of walls defining an internal space and an opening configured to provide access to the internal space. A flange extends from a portion of the container and comprises a pattern of holes configured to indicate a container type. The container type defines at least one category of waste to be placed in the container.

In another embodiment, a system comprises a plurality of disposable containers of different types. Each container type corresponds to a category of medical waste, and each container comprises a machine-readable key configured to indicate the container's type to a sorting machine. Each container also comprises an automatically-operable gate configured to selectively occlude and reveal an opening of the container. The gate is further configured to be automatically locked.

In another embodiment, a container for use in a medical waste system comprises a means for defining an internal space, and an aperture means for providing access to the internal space. An openable means for selectively occluding and revealing the aperture means is operable by an automated machine. A key means is also provided for indicating a container type to the machine.

In another embodiment, a disposable container for use in a medical waste system comprises a means for defining an internal space and a means for provide access to the internal space. A flange means extends from a portion of the container and indicates a category of waste to be placed in the container.

In another embodiment, a method of using a disposable container comprises receiving a disposable container in a sorting machine. The method is continued by reading an identification key on the container. The identification key defines a category of waste to be placed in the container. The method is continued by directing a user to place a plurality of waste items in the container and alerting a user when the container is full.

In another embodiment, a method of using a disposable container comprises receiving a plurality of disposable containers in a sorting machine, wherein each container corresponds to a waste category. The method further comprises reading an identification key on each container. The identification key defines a category of waste to be placed in the container. The method further comprises determining a waste category to which an item of waste belongs, providing access to a selected one of the containers, and directing a user to place the waste item in the selected container.

In another embodiment, a method of using a disposable container for sorting and disposing of medical waste comprises placing a plurality of containers in a sorting machine. Each container comprising an opening configured to provide access to an internal space. The method further comprises operating the machine to read an identification key from each container to determine a category of waste to be placed in each container and to automatically operate a door to selectively occlude and reveal the opening.

In another embodiment, a method of sorting medical waste comprises, in no particular order, receiving an identifier associated with waste to be disposed of, and retrieving (based on the identifier) information from a database. The information is derived from applicable rules regarding disposal of waste items. The method further comprises assigning the waste to a disposal category based on the information retrieved from the database, locating a container associated with the assigned disposal category, and facilitating disposal of the waste item into the container associated with the assigned disposal category.

In another embodiment, a method of sorting medical waste for disposal comprises identifying a plurality of containers in a sorting station and determining a waste category associated with each container, identifying an item of waste to be disposed of, and assigning the item to a waste category.

In another embodiment, a method of sorting medical waste comprises identifying a plurality of containers in a sorting station and determining at least one waste category associated with each container. The waste categories are ranked from least to most hazardous. The method further comprises identifying an item of waste to be disposed of, and assigning the item to a first waste category. The method further comprises determining whether a container associated with the first waste category is present in the sorting station, and if one is not present, re-assigning the waste item to a second waste category that is ranked more hazardous than the first waste category.

In another embodiment, a method of sorting medical waste items for disposal comprises identifying a plurality of containers in a sorting station and determining a waste category associated with each container. The waste categories are again ranked from least to most hazardous. The method further comprises identifying an item of waste to be disposed of, and assigning the item to a first waste category. The method further comprises determining whether a container associated with the first waste category is present in the sorting station, and if one is not present, directing a user to another sorting station which does have a container associated with the first waste category.

In another embodiment, a system for sorting medical waste items comprises a sorting station in electronic communication with a classification database which lists a plurality of waste item identifiers distributed into a plurality of waste categories. A plurality of containers are positioned in the sorting station. Each container is sized and configured to receive a plurality of medical waste items. A waste item identification device is configured to receive a waste item identifier from a waste item. A decision system is configured to classify the waste item into a waste category using the waste item identifier and information contained in the classification database. Each of the containers is associated with one of the waste categories, and the decision system is further configured to indicate into which of the containers a waste item should be deposited based on the waste category.

In another embodiment, a waste sorting and disposal system comprises a sorting and disposal station comprising a waste item identification device and a plurality of container compartments. The system also has a database which comprises medical waste item classification information derived from rules and regulations affecting the disposal of medical waste items, and a plurality of containers positioned in the container compartments. Each container comprises a machine-readable identification key and an automatically operable door formed integrally with the container. The station is configured to read each identification key upon placement of a container in a container compartment, and to selectively open and close the doors of each of the plurality of containers.

In another embodiment, a system for sorting medical waste items comprises a sorting station in electronic communication with a classification database which lists a plurality of waste item identifiers distributed into a plurality of waste categories. The waste categories are ranked from least to most hazardous. A plurality of containers are positioned in the sorting station, each container being sized and configured to receive a plurality of medical waste items. A waste item identification device is configured to receive a waste item identifier from a waste item, and a decision system is configured to assign the waste item to a waste category using the waste identifier and information contained in the classification database. Each of the containers is associated with at least one of the waste categories, and the decision system is further configured to indicate into which of the containers a waste item should be deposited based on the waste category. The decision system is further configured to open a container associated with a highest hazardousness level if the station does not include a container associated with the assigned category.

In another embodiment, a system for sorting medical waste items comprises a plurality of sorting stations in electronic communication with one another via a central processing unit in a centralized network. The sorting stations and the central processing unit are often physically separated from one another. A classification database, which lists a plurality of waste item identifiers distributed into a plurality of waste categories, resides in the central processing unit. Each sorting station comprises a plurality of containers, and each container is sized and configured to receive a plurality of medical waste items. A waste item identification device is configured to receive a waste item identifier from a waste item, and a decision system is configured to classify the waste item into a waste category using the waste identifier and information contained in the classification database. Each of the containers is associated with one of the waste categories, and the decision system is further configured to indicate into which of the containers a waste item should be deposited.

In another embodiment, a system for sorting medical waste items comprises a plurality of sorting stations in electronic communication with one another in a de-centralized network. The sorting stations are physically separated from one another, and a classification database resides on a data storage device in at least one of the stations. The database lists a plurality of waste item identifiers distributed into a plurality of waste categories. Each sorting station comprises a plurality of containers, and each container is sized and configured to receive a plurality of medical waste items. Each container is designated as a specific type which defines a group of items to be placed therein. A waste item identification device is configured to receive a waste item identifier from a waste item, and a decision system is configured to classify a waste item into a waste category using the waste identifier and information contained in the classification database. The decision system is further configured to indicate into which of the containers a waste item should be deposited.

In another embodiment, a method of sorting medical waste items comprises joining a plurality of physically separated sorting stations in electronic communication with one another in a network. The method further comprises joining each sorting station in electronic communication with a classification database which lists a plurality of waste item identifiers distributed into a plurality of waste categories. The method further comprises placing a plurality of containers in each station, each container being sized and configured to receive a plurality of medical waste items. The method further comprises providing each station with a waste item identification device configured to receive a waste item identifier from a waste item, and configuring a decision system in each station to classify waste items into waste categories using the waste identifier and information contained in the classification database.

In another embodiment, a waste system comprises a station comprising a waste identification device and a plurality of container compartments. A plurality of containers are positioned in the container compartments, and each container comprises a machine-readable identification key. The station is configured to read each identification key upon placement of a container in a container compartment.

In another embodiment, a waste system comprises a means for sorting waste comprising a means for identifying waste and means for supporting a container. Each one of a plurality of means for containing waste comprises a means for machine identification of the means for containing waste. The means for sorting further comprises a means for reading each means for machine identification upon placement of a means for containing in a means for supporting.

In another embodiment, a waste sorting and disposal system comprises a sorting and disposal station comprising a waste identification device and a plurality of container compartments A plurality of containers are positioned in the container compartments, each one comprising a machine-readable identification key which identifies a waste category defining characteristics of the waste to be placed in each container. The station is configured to read each identification key upon placement of a container in a container compartment, and the waste category of each container is independent of the container compartment in which each container is positioned.

In another embodiment, a sorting system for separating waste into a plurality of containers based on a classification of the waste item is provided. The system comprises a plurality of containers, each associated with at least one of a plurality of a waste categories. A waste detector is configured to identify waste presented to the detector. A sorting mechanism is configured to place waste into one of the containers based on information received from the waste detector. The system also comprises a sensor configured to determine whether at least one of the containers has waste therein.

In another embodiment, a sorting system for separating waste into a plurality of containers based on a classification of the waste is provided. The system of this embodiment comprises a plurality of containers, each associated with at least one of a plurality of a waste categories. A database comprises waste classification information derived from rules and regulations affecting the disposal of waste items. A waste detector is configured to identify waste presented thereto, and a sorting mechanism is configured to place waste into one of the containers based on information received from the waste detector. A sensor is configured to determine whether at least one of the containers has waste therein.

In another embodiment, a sorting system is provided for separating waste into a plurality of containers based on a classification of the waste. The system comprises a plurality of means for containing medical waste. Each of said means for containing medical waste is associated with at least one of a plurality of a waste categories. A means for identifying waste is provided, as is a means for sorting waste into one of the means for containing using information received from the means for identifying waste. The system also comprises a means for determining whether at least one of the containers has waste therein.

BRIEF DESCRIPTION OF DRAWINGS

FIG. 3 is a perspective illustration of an embodiment of a wall-mounted sorting and disposal station;

FIG. 4 is a perspective illustration of one embodiment of a floor-standing sorting and disposal station;

FIG. 22a is an electronic schematic of one embodiment of an array of light detectors

FIG. 23a is an electronic schematic of one embodiment of an alternative embodiment employing a video system;

DETAILED DESCRIPTION

Waste Sorting And Disposal System

Figure 1:
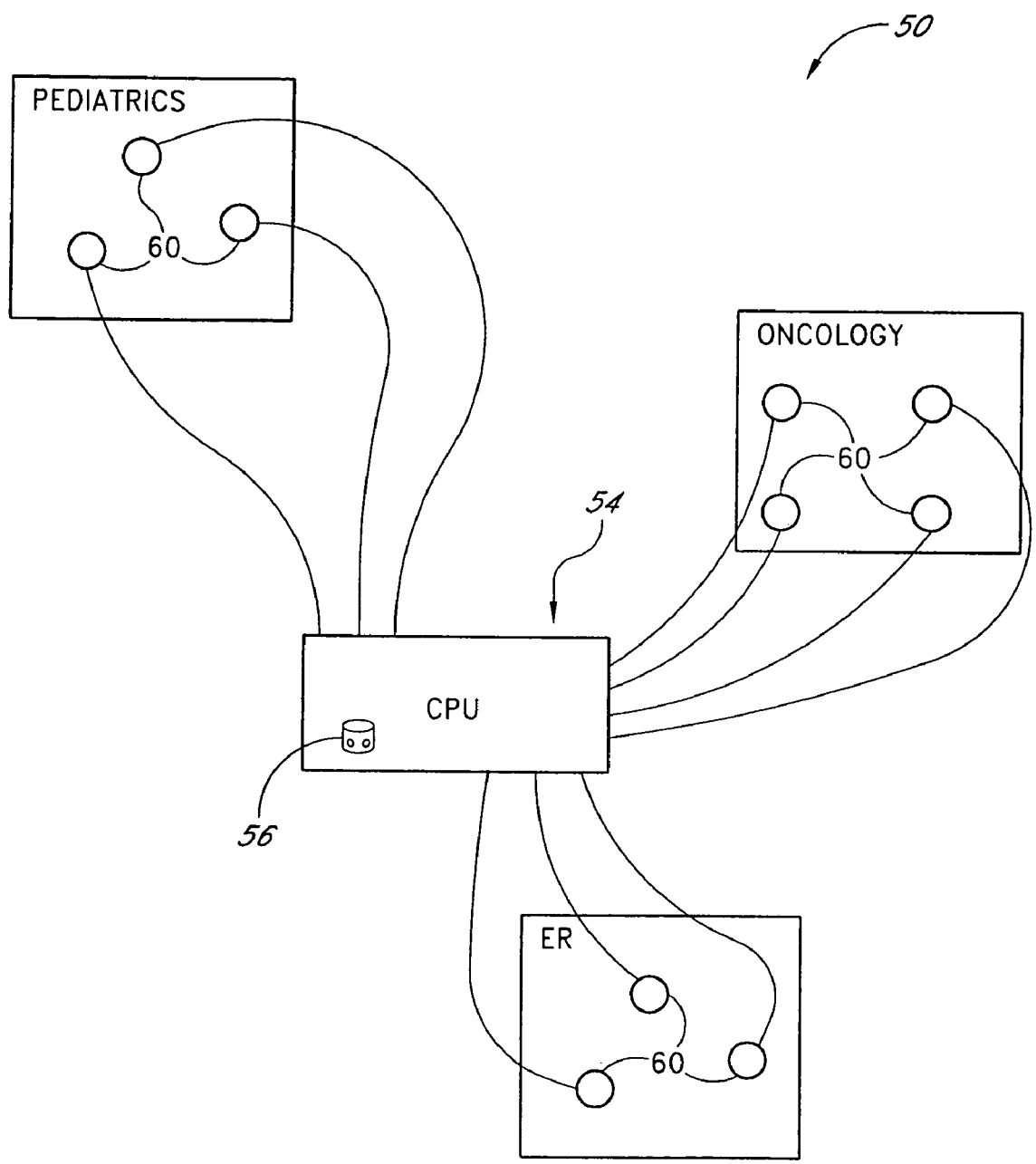
FIG. 1 is a schematic illustration of one embodiment of medical waste sorting and disposal system including a plurality of interconnected sorting and disposal stations in a centralized network.

Embodiments of devices and methods for sorting a plurality of medical wastes will now be described with reference to the attached figures. In several embodiments, the waste sorting and disposal system is automated. In some embodiments, a medical waste sorting system comprising a plurality of individual sorting and disposal stations connected to one another via a centralized or de-centralized network is provided. Alternatively, a medical waste sorting system can comprise one or more stand-alone sorting and disposal stations configured to operate independently of any other device. Although some of the following embodiments are described in the context of individual stand-alone stations, it should be recognized that such individual stations can be connected in a networked system to provide additional functionality or to improve efficiency. Conversely, some embodiments are described below in the context of networked systems, certain features and advantages of which can be readily applied to individual stand-alone systems as will be clear to the skilled artisan. The term "sorting" is a broad term and shall be given its ordinary meaning and generally refers to the distribution of one or more waste items into one or more appropriate waste receptacles. The term "disposing" is also a broad term and shall be given its ordinary meaning and shall, in some embodiments, generally refer to the discarding or "throwing out" of one or more items of waste into an appropriate receptacle.

In one embodiment, a waste sorting and disposal station comprises a sorting station or machine, which includes a series of container positions or compartments, each compartment being configured to receive a disposable container for collecting waste belonging to a particular category or classification. Some embodiments of a sorting station comprise a waste-identifying device, a processor configured to carry out a waste-sorting algorithm, and a waste-sorting mechanism.

In some embodiments, a sorting machine comprises one or more sensors for determining the presence of a container, a type of container, and/or a volume or weight of a container. In another embodiment, the sorting machine includes one or more sensors (e.g., an optical sensor) to determine which container the item was deposited into and/or a time at which an item is deposited. Additionally, a sorting machine/station can include any of a variety of computer peripherals, such as user input devices (e.g., touch screens, keyboards, pointer devices, etc.), display devices, sound-producing devices (e.g., speakers or buzzers), or any other peripheral device.

In many embodiments, several container types are provided, each type being associated with a particular category or classification of pharmaceutical waste. For example, in some embodiments, container types can include sharps containers, chemotherapy agent containers, infectious waste containers, ignitable waste containers, hazardous P-list waste containers, hazardous U-list waste containers, toxic pharmaceutical waste containers, non-toxic pharmaceutical waste containers, chemotherapy sharps containers, corrosive waste containers, or reactive waste containers. Additional container types can also be used as desired. In one embodiment, the container types are pre-designated by the container provider. In other embodiments, the container types are assigned by the hospital so that the hospital can individually customize its waste sorting system. For example, some hospitals may desire to define their own waste categories in order to comply with internal goals, thus user-defined container types can also be provided.

In a preferred embodiment, a waste identifying mechanism is provided. In several embodiments, the waste identifying mechanism is configured to identify a particular item of waste. Identification is preferably accomplished prior to deposit into the appropriate container. Identification of the waste item can be accomplished by scanning a barcode, reading a label (e.g., using an optical scanner and Optical Character Recognition software), reading a Radio Frequency identification (RFID) tag, chemical sensors, spectroscopic analyzers, or by measuring or evaluating any other qualitative parameter of the waste item presented for identification. Alternatively still, an item of waste can be identified by user input of information such as a trade name, a generic name, a chemical name, National Drug Code (NDC) or other data associated with a particular item of waste. For example, a user can simply read a waste identifier from an item of medical waste and enter the identifier into the system via a keyboard, touch screen or other user input device.

In one embodiment, once an item of waste is identified, the sorting algorithm determines to which of a plurality of waste categories the item belongs. The station then indicates to the user which container is associated with that category. For example, in some embodiments the station indicates a correct container by opening a door providing access to the container. Alternatively, such an indication can be provided by illuminating a light or displaying a name or number of a container on a display device. In some embodiments, a waste sorting mechanism can carry out or instruct a user in delivery of the waste item to the appropriate disposable container.

In some embodiments, the waste sorting mechanism comprises a plurality of openings providing access to the plurality of containers. For example, each of the containers can be configured to interface with an automatically operable door or other means to present the container opening to the user. Some embodiments of such an interface are described in further detail below. Alternatively, the sorting machine can be configured to provide access to an appropriate container in other ways, such as by moving a container relative to the machine in order to present a container opening to a user. In further alternative embodiments, the sorting mechanism can include a series of lights or other indicators configured to inform a user of the correct container for a particular item of waste. Alternatively still, the sorting mechanism can include an apparatus configured to receive an item of waste from a user and physically convey the item to the appropriate disposable container.

In some embodiments, a single waste item may call for disposal in multiple containers. For example, a syringe might contain a quantity of a hazardous or controlled substance, which requires disposal in a first container. However, the syringe itself may require disposal in a second, separate container. In such embodiments, it is desirable for the system to determine an appropriate sequence for the disposal of the separate parts of a single item. In the event that a waste item contains information (such as a barcode or label) sufficient to inform the system of the need for a sequence of disposal steps, the system can determine the optimum sequence, and can then inform the user of the appropriate sequence. The system may inform a user of the appropriate sequence by sequentially opening appropriate doors and/or by displaying instructions on a display screen. In one embodiment, a means can be provided to determine whether an item of waste is empty or contains residual or bulk hazardous or non-hazardous contents.

Alternatively, it may be desirable for a user to determine the best sequence for disposal, in which case, the user may enter information into the system requesting a particular sequence. Additionally, it may also be desirable for the system to include "shortcut keys" in order to provide quick access to frequently-used containers, such as sharps containers. Such shortcut keys can be configured to quickly open a selected container.

In some embodiments, when a single waste item comprises a composite of elements falling into different waste categories, such as a syringe containing a controlled substance, which might, if disposed separately, be sorted into two different containers, the waste sorting system can indicate disposal of the composite waste item into the highest hazard level container. In this manner, when it is inefficient, ineffective or even dangerous to separate the single composite waste item into its individual components, hospitals can still achieve compliance by disposing of such hybrid or composite items into the most conservative hazard container. In some embodiments, the containers within a sorting station can be ranked in order from "least" to "most" hazardous in order to facilitate a determination of which container is the "most conservative" hazard container in a given station. A determination of whether a particular container type (and corresponding waste category or categories) is higher or lower on a hazardousness spectrum can be determined by a variety of suitable methods. In some cases, a hazardousness spectrum can be determined empirically, while in other embodiments, the varying degrees of hazardousness may be determined by comparing properties such as relative reactiveness, bioactivity, etc. of elements of a particular category.

In some embodiments, when a waste item is unrecognized by the identification means, the sorting system will indicate disposal to the highest hazard waste container. The system will notify the disposer that the waste item was unrecognized. In another embodiment, the sorting system may also notify a database or database personnel that the waste item is unrecognized, thus facilitating a database upgrade to include that waste item for future disposals.

In some embodiments of the invention, it may be advantageous to determine the quantity of waste that has already been deposited into one or more containers. In some embodiments, one or more sensors are used to quantitatively assess one or more parameters of the container and/or waste. These quantitative sensors include, but are not limited to, sensors that detect the weight, volume, density, and/or fill level of the waste in the container.

In one embodiment, one or more fill sensors are provided. A fill level sensor can be used to monitor a fill level of each of the disposable containers to determine when a particular container is full. Once a container is determined to be full, the sorting system can signal a user to replace the full container with a new empty container. Additionally, once a particular container is full, some embodiments of the system can be configured to determine the weight or volume of waste material within the full container. The system can also be configured to print a label to be affixed to the container. The label can include a variety of information relating to the disposal of the waste items, the quantity, weight or volume of the items contained therein, a waste category name or code, etc.

In some embodiments, quantitative sensors are not used. Instead, in one embodiment, the quantity of waste is determined by direct visualization of the waste in a container. Transparent or translucent containers are provided to facilitate visualization in some embodiments. In several embodiments, the containers are opaque, but provide a section or "view-strip" of translucent or transparent material to permit visualization. In one embodiment, one or more sensors are provided in conjunction with means to directly visualize waste quantity. In one embodiment, means for detecting a quantity of waste are not needed because the containers are replaced at regularly scheduled intervals, as determined by a waste transport company, a disposal company or hospital staff and independent of how much waste is in any given container.

In some embodiments, when a new container is placed in a sorting and disposal station, the system can be configured to identify the new container according to the type of waste the container it is permitted to hold. In some embodiments, a waste sorting and disposal station can be configured to recognize containers in a static mode in which each container position within the station/machine is associated with a specific container type. Upon insertion of a new container into the station, the system can recognize the type of container and can determine whether the new container is the correct type for the position in which it was placed. Thus, a system of this type can insure that a consistent arrangement of container types is maintained.

Alternatively, and more preferably, a sorting and disposal station is configured to recognize container types in a dynamic mode in which the machine is able to recognize and adapt to changing container arrangements. Thus, according to this embodiment, each container position/compartment in a station will recognize and accept any new container regardless of the container type, and the software will adapt a sorting routine to account for the new configuration. In some cases, it may be desirable for a single station to have multiple containers of a single type. For example, an oncology department may desire several chemotherapy containers and no hazardous pharmaceutical containers, while an area of the hospital that does not use chemotherapeutic drugs may want several sharps containers and no chemotherapy containers. This allows for substantial flexibility and customizability in system set up. In further embodiments, a sorting and disposal station can exhibit aspects of both static and dynamic systems, such as by allowing any type of container in any container position, while requiring a minimum number of containers of a particular type.

Network-Implemented System

In some embodiments, a waste sorting and disposal system can be configured on a hospital-wide level by providing a plurality of cooperating sorting and disposal stations throughout the hospital. The system can include a plurality of individual sorting and disposal stations in a variety of types, arrangements, sizes, functionalities, etc.

FIG. 1 illustrates an exemplary embodiment of a centralized waste sorting and disposal network. As shown, a centralized network 50 can include a main central unit 54 provided in electronic communication with a plurality of smaller "satellite" units 60 throughout a facility. In such a centralized network, the main unit 54 can include a server containing the classification database 56 and any other information to be shared with the satellite units 60. As information is needed by a satellite unit 60, it can query the database via the network in order to obtain that information. Alternatively, or in addition, the main unit 54 can be configured to push updates to the satellite units at regular intervals, or as new information becomes available. In some embodiments, the main unit 54 can also act as a central hub for various communications, tracking, maintenance and other system functions.

Figure 2:
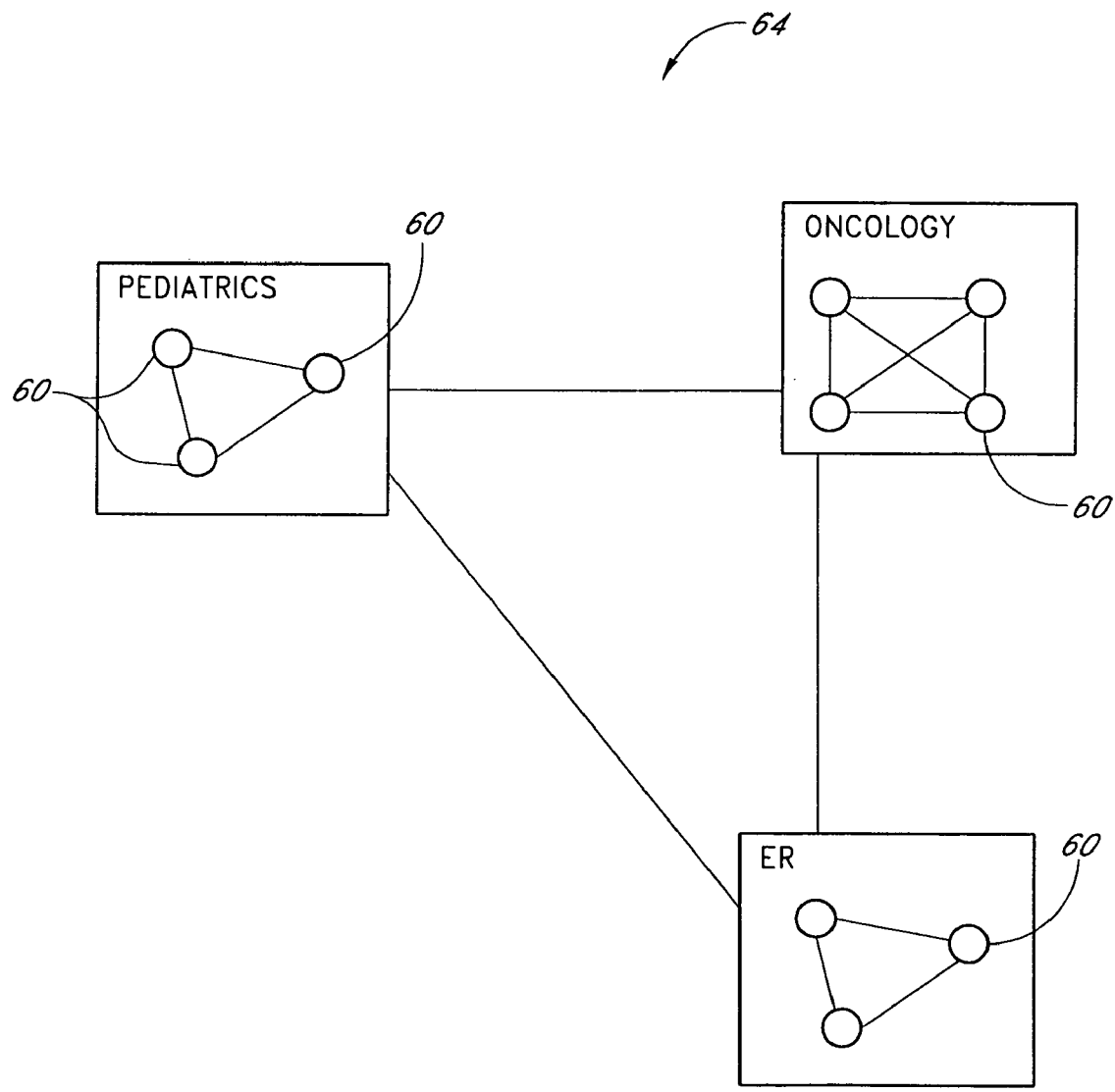
FIG. 2 is a schematic illustration of one embodiment of medical waste sorting and disposal system implemented in a decentralized network.

FIG. 2 illustrates an embodiment of a de-centralized medical waste sorting and disposal system. The network 64 of FIG. 2 is substantially decentralized and comprises a plurality of sorting and disposal stations 60 which can communicate with one another according to any suitable method. For example, in a decentralized network, each of the individual units may locally store a copy of the classification database. In order to keep the classification database updated, the individual units can share information with one another according to any of a variety of peer-to-peer network protocols. The individual stations can also share other information with one another as will be further described below.

In either case (centralized or decentralized network), the network elements can be configured to communicate with one another via any suitable wired and/or wireless network communication protocol. Many hospitals already have existing wired and/or wireless networks connecting computers and communications devices throughout the facility. Thus, in some embodiments, a networked medical waste sorting and disposal system can be configured as an add-on to an existing network. Alternatively, a networked medical waste sorting and disposal system can be configured as an independent network. Additionally, the main unit (if present) and/or the satellite unit(s) can further be connected to external networks (e.g., the internet) via wireless or wired connections as desired.

In some embodiments, it may be desirable for one sorting and disposal station to have access to information about one or all of the other stations in the network. For instance, it may be desirable for any one station to determine an arrangement of containers in one or more nearby stations. For example, if a clinician presents an item of waste to a station which does not presently have a container suitable for disposal of the presented item, that station can direct the clinician to the nearest station that does have an appropriate container installed. In further embodiments, a log of such re-directions can be kept in order to increase efficiency by arranging the sorting and disposal stations to include the most frequently used containers for a given location.

Some embodiments of a waste sorting and disposal system are configured to communicate information directly to a technician, maintenance person, clinician or other person. For example, the system can be configured to alert a maintenance person when a container is full by sending an alert signal to a pager, cell phone, PDA, computer terminal, or any other suitable device. The maintenance person can then remove the full container and replace it with an empty container (of the same or a different type).

Individual Sorting/Disposal Stations

A medical waste sorting and disposal station can take a variety of forms depending on the specific needs of a given clinic, hospital, department, clinician, etc. For example, some embodiments of sorting and disposal stations 60 are illustrated in FIGS. 3–12. For example, a station can be provided in a wall-mounted unit 60a (e.g., see FIG. 3), in a floor-standing unit 60b (FIG. 4), on a wheeled cart 60c (FIGS. 5 and 6), attached to a patient bed, attached to an IV pole, attached to an existing wheeled medications cart 60d (FIGS. 7–9), or any of a variety of other shapes, forms and mounting locations.

Figure 6:
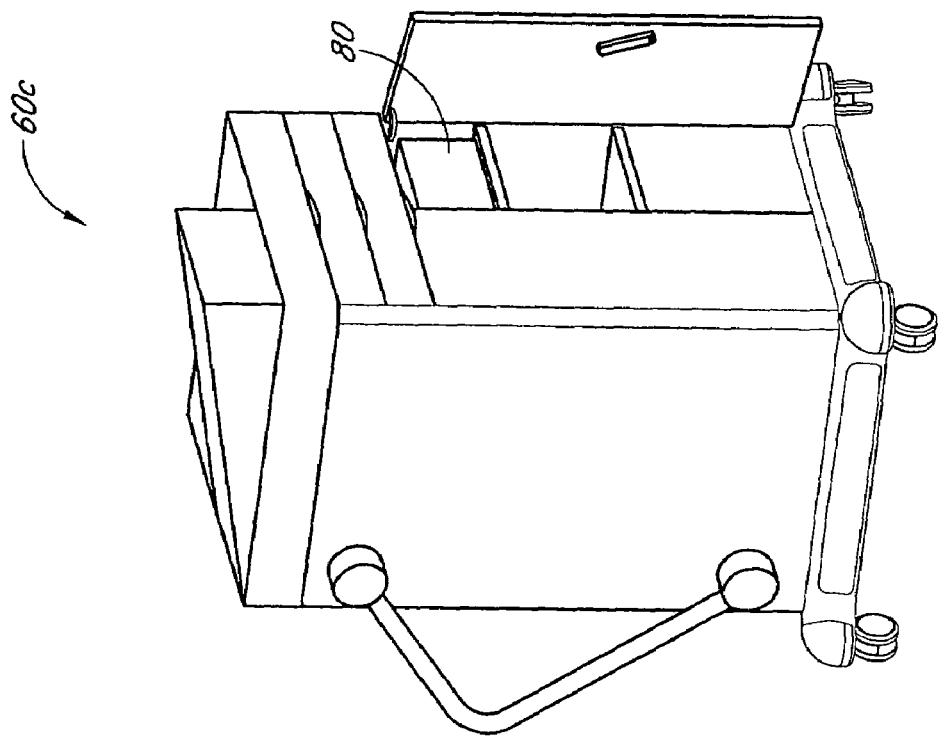
FIG. 6 is a rear perspective view of one embodiment of a rolling cart sorting and disposal station.
Figure 5:
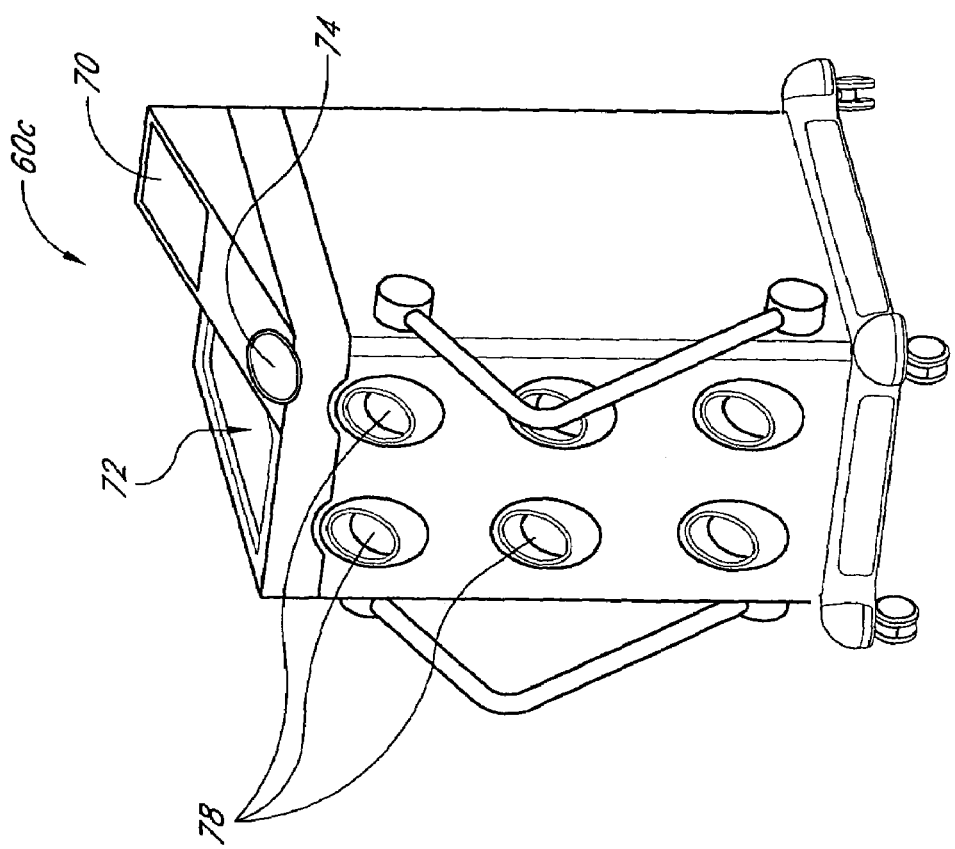
FIG. 5 is a front perspective view of one embodiment of a rolling cart sorting and disposal station.

The embodiment of FIGS. 5 and 6 also includes a display device 70, a weight scale 72, a scanner 74 for identifying waste items and a plurality of apertures 78 configured to reveal openings to respective containers 80.

Figure 7:
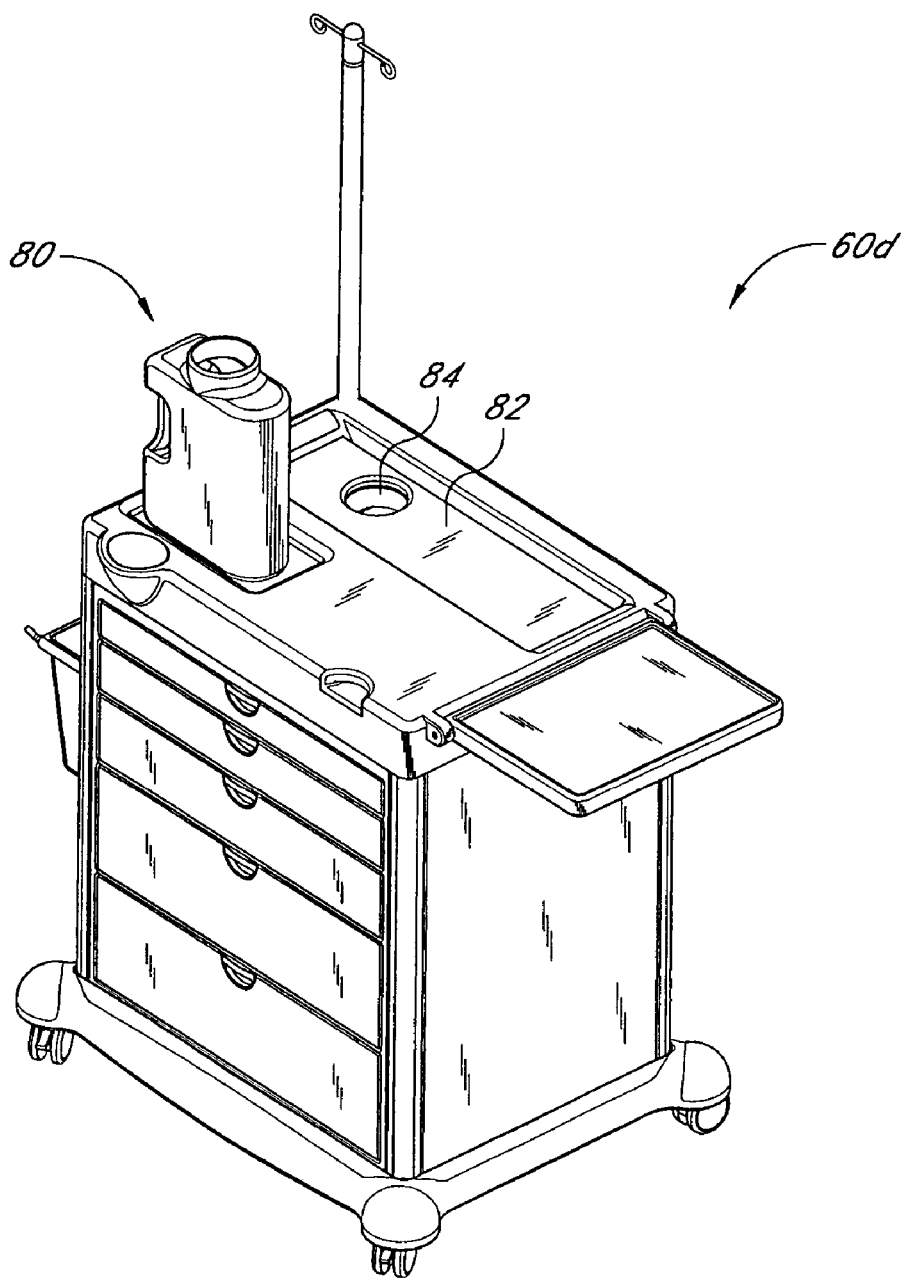
FIG. 7 is a perspective view of one embodiment of a sorting and disposal station incorporated into a rolling medications cart.
Figure 8:
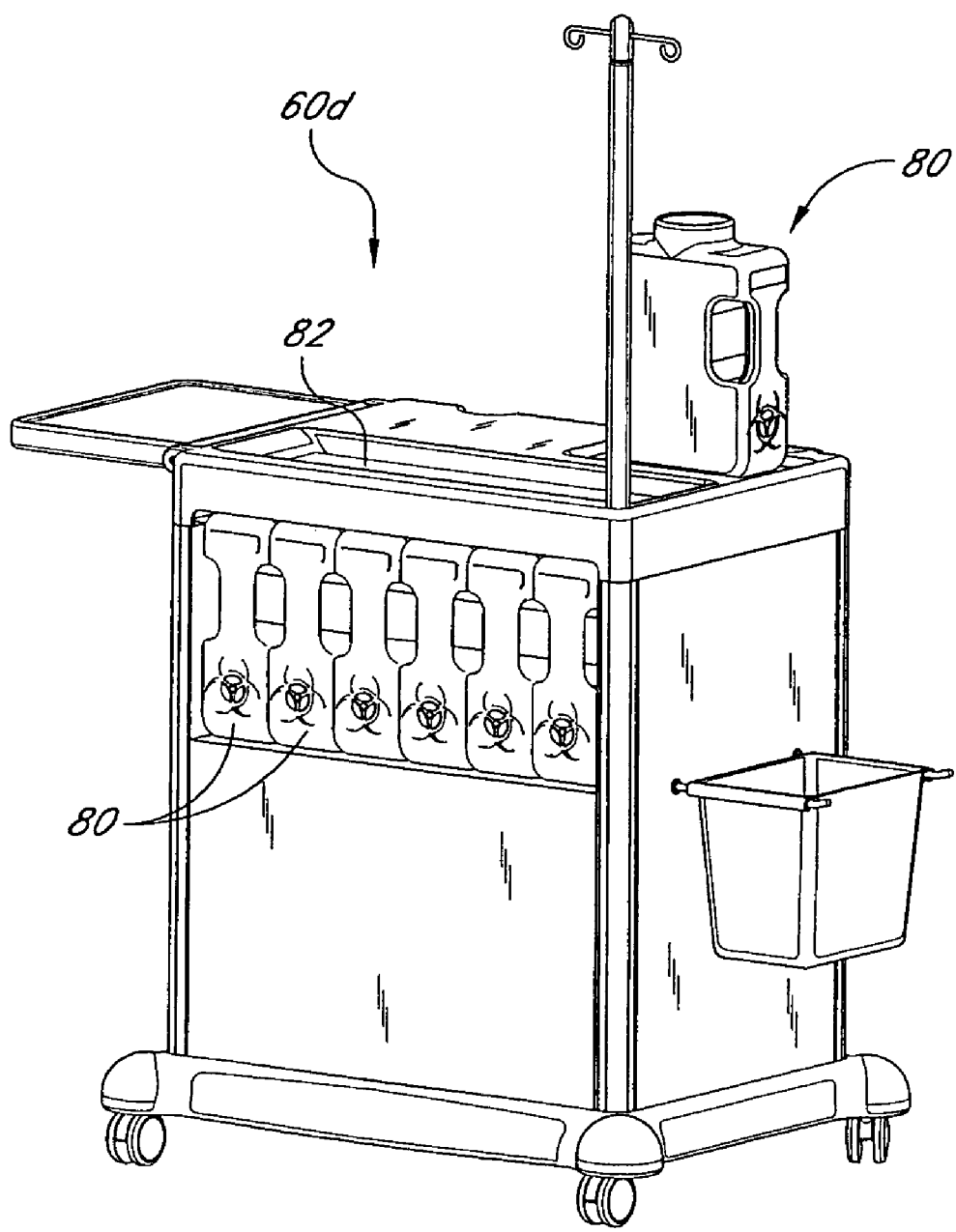
FIG. 8 is a rear perspective view of one embodiment of the cart of FIG. 7.
Figure 9:
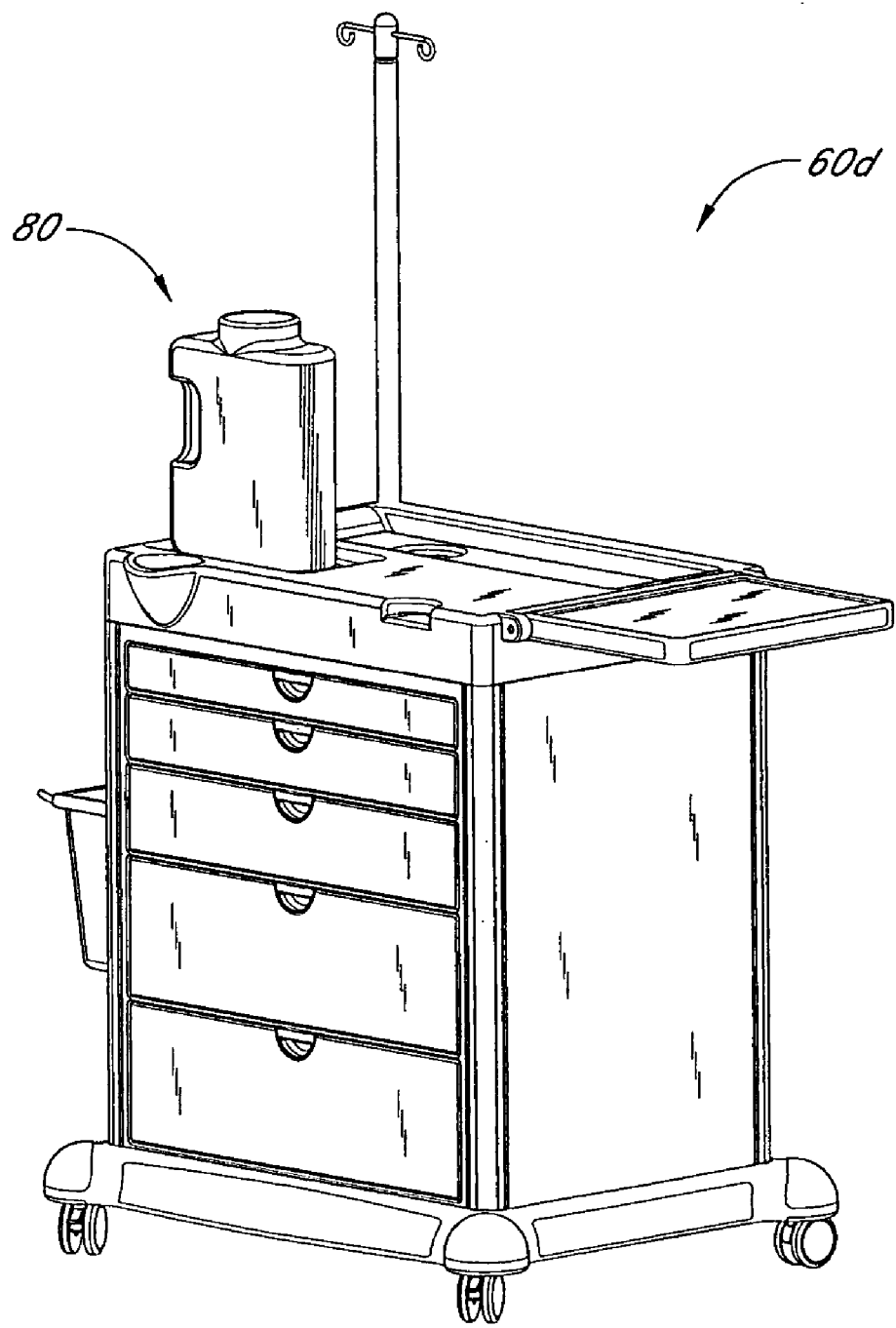
FIG. 9 is an alternative embodiment of the cart of FIG. 7.

With reference to FIGS. 7–9, some embodiments of a station can comprise a movable lid 82 with a single aperture 84. The lid 82 can be substantially flexible such that it can be driven to translate above the containers in order to selectively provide access to any one of the containers below the lid 82.

In some embodiments, the sorting machine can be configured to provide access to an appropriate container in other ways, such as by tilting, raising, lowering, pivoting, translating or otherwise moving a container relative to the machine in order to present the container opening to a user.

Figure 10:
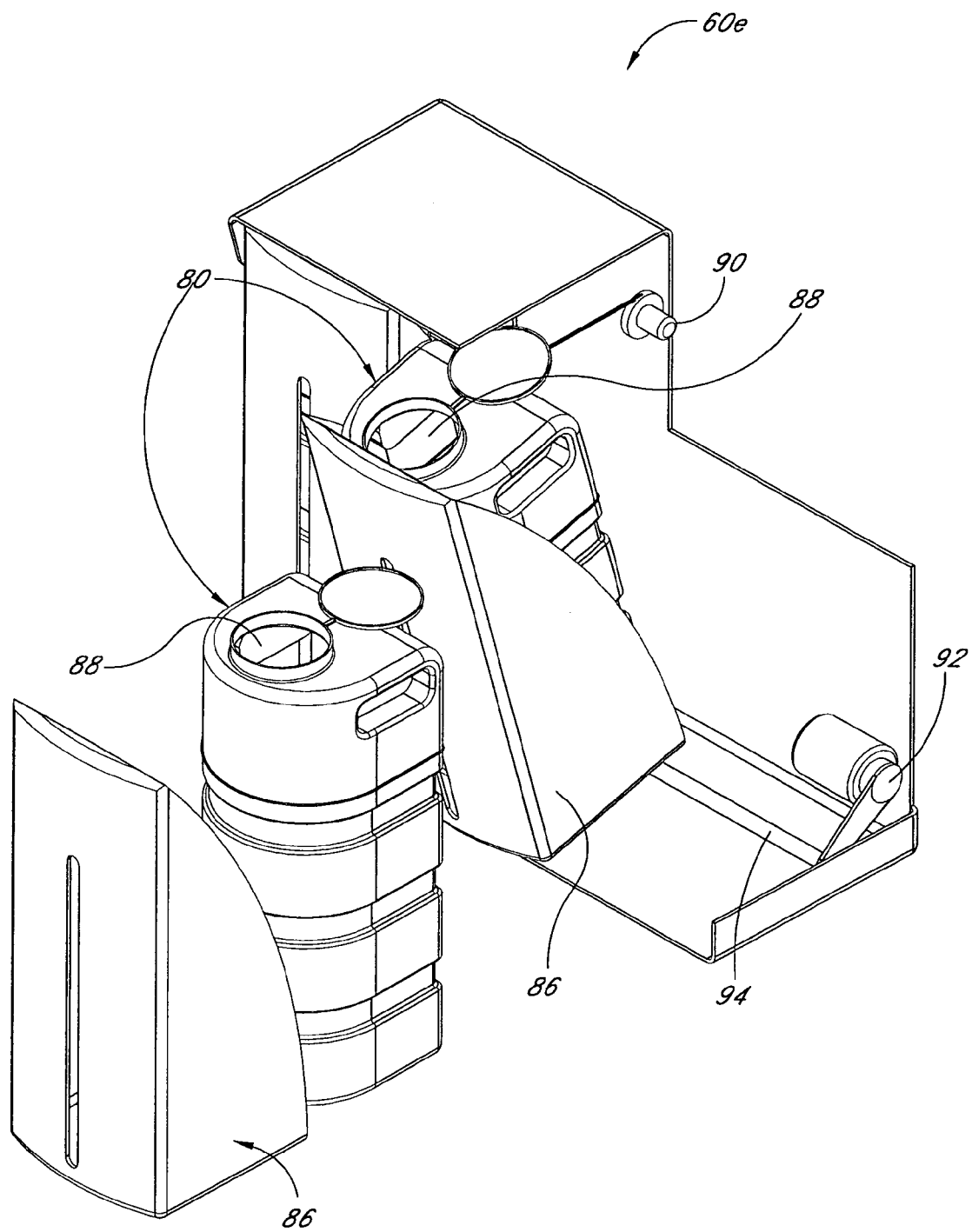
FIG. 10 is a partially exploded perspective view of one embodiment of a sorting and disposal station comprising pivotable containers and sleeves.

FIG. 10 illustrates an embodiment in which a sorting station comprises a series of hinged sleeves 86 configured to pivot relative to a fixed portion of the sorting station. Each sleeve 86 is generally configured to temporarily house a disposable container 80. The station 60e comprises a series of actuators configured to pivot each sleeve 86 and its associated container 80 outwards, thereby exposing the container opening 88. In one embodiment, an actuator 90 can be located adjacent an upper portion of a container 80 and can be configured to push the upper portion of the container outwards from the station. Alternatively the sleeve 86 can be biased outwards by a spring or simply by gravity, and an upper actuator can be configured to release the sleeve/container to allow it to pivot outwards to open. The upper actuator can then pull inwards to return the container/sleeve to a closed position.

Alternatively or in addition, a lower actuator 92 can be provided adjacent a bottom portion of the container/sleeve combination. In one embodiment, a lower actuator 92 can comprise a drive axle 94 rigidly mounted to the sleeve 86. The axle 94 can be driven by a motor or other mechanism in order to pivot the sleeve 86 inwards and outwards. A container 80 can be inserted into the sleeve 86 and pivoted back so that a fixed portion of the station 60e covers the container opening 88. During use, the actuator 90 or 92 causes the sleeve 86 to pivot outward from the station 60e, thereby exposing the container opening for use. The container 80 can be removed by sliding it out of the sleeve 86. In an alternative embodiment, the above system can be provided without a sleeve 86 by incorporating an actuator and a pivot point into the container itself. In further alternative embodiments, other actuators, drive mechanisms, etc can be used in order to selectively provide access to a container opening.

In another embodiment, the station can be configured to house each of the containers in a sliding drawer. The drawers can include actuators configured to move the drawer outwards until an opening is exposed. The containers can then be easily removed once they are full.

Figure 12:
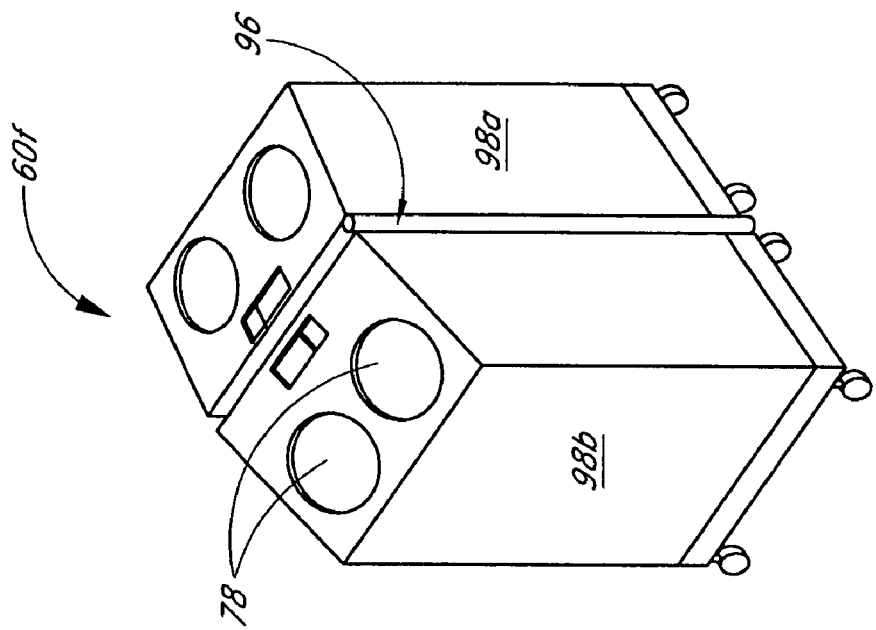
FIG. 12 is a perspective view of one embodiment of the convertible rolling cart in a second configuration.
Figure 11:
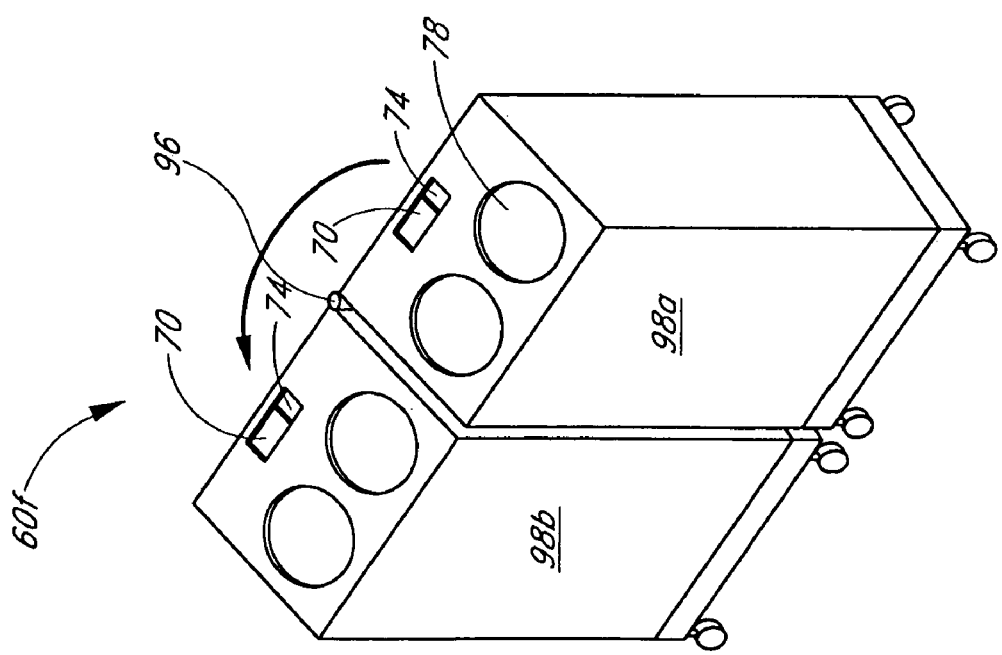
FIG. 11 is a perspective view of one embodiment of a sorting and disposal station in the form of a convertible rolling cart in a first configuration.

FIGS. 11 and 12 illustrate another embodiment of a waste sorting and disposal station 60f in the form of a convertible rolling cart. In a first orientation, illustrated in FIG. 11, the station 60f is a two-sided rolling cart. The station 60f of this embodiment can be provided with a hinge 96 configured to allow the two sides 98a, 98b of the cart 60f to unfold into a one-sided arrangement. In this second configuration (shown in FIG. 12), the station can be mounted or placed against a wall.

In some embodiments, a sorting and disposal station 60 can include a scale configured to determine a weight of a full container. Thus, a scale 72 can be provided on an upper or other accessible portion of the station. Alternatively, the station can include a scale (e.g., a load cell) to continuously or repeatedly weigh each container within the station. Such information can be useful in creating a manifest for the containers before transportation of the containers to an appropriate disposal facility. Additionally, or alternatively, a station can include a fill level sensor for continuously or intermittently determining a fill level of a container. Embodiments of a fill-level sensor are described in further detail below.

Disposable Containers

In some embodiments, the disposable containers are generally designed to be low cost, yet include features that provide a functional interface with mechanisms in a sorting station to perform several desired functions. For example, in some embodiments, each container includes a door or lid which can be opened and closed automatically in order to allow or prevent access to a particular container at a particular time. Additionally, the containers can be configured to interface with sensors for determining a quantity of contents within the container, and/or sensors for determining a type of container.

In some embodiments, the containers 80 are blow molded (or otherwise formed) from polypropylene, high molecular weight polyethylene, polyvinylchloride or any other suitable plastic or other material as desired. In some embodiments, the containers 80 have substantially frosted or translucent side walls. The containers will typically be sized to have an internal volume of anywhere from 1 to 20 gallons, however greater or smaller volumes can also be used as desired. For example, in some particular embodiments, containers can be provided in 1-gallon, 3-gallon and 8-gallon sizes.

The shape of the containers can vary widely. In some preferred embodiments, the containers include a lifting handle, a primary opening which can be automatically and/or manually closed or sealed, and a bottom surface configured to allow the container to stand upright. Additionally, the disposable containers can also include features such as an automatically-openable door or lid, a manually closable lid, features for accurately locating the container in a container compartment of a station, a viewing window for visually verifying a fill level, and/or identification information for informing a user of a container's contents (or intended contents).

The containers can be provided with an opening 88 having a variety of shapes and/or features. For example, in one embodiment, the opening 88 is substantially circular and has a minimum internal diameter of at least about three inches (~76 mm). In other embodiments, the opening 88 can be substantially elliptical, rectangular, polygonal or otherwise shaped, and can be any suitable size, including sizes smaller than three inches in diameter. The particular type or types of waste to be deposited in a particular container can be a significant factor that can be used in determining a suitable size and/or shape of a container opening. In general, the container opening should be sized to easily accept the largest waste item that is expected to be deposited in the container. For example, some containers might receive full or partially full liter-sized IV bags, gallon-sized biohazard bags or other large items. It is generally desirable that the container opening be configured to accept these large items easily and without tearing the bags or otherwise damaging or causing spillage of a waste item. The skilled artisan will recognize that other factors may also affect a choice of container opening size or shape.

In some embodiments, disposable containers are provided in a plurality of types, each type corresponding to a respective waste category or waste classification. In order to allow clinicians, maintenance people, and any other persons who may handle the containers to quickly and easily differentiate containers of various types, the containers can be color-coded to correspond with a particular type or category of waste. In some embodiments, a color-coding scheme can be selected to match industry standards for various types of medical waste. Red, for example, typically signifies infectious waste, while yellow typically signifies chemo therapy drugs. Color-coded containers can advantageously simplify the tasks associated with manual transportation and processing of the containers, and can aid in insuring that such tasks will be handled correctly for each waste stream.

Alternatively, such visual verification of a container's type can be provided by any other suitable method. For example, the various container types can be indicated by labels bearing numeric, alphanumeric, graphical or symbolic information. Such labels can include printed stick-on labels or various features molded or formed directly into portions of the containers themselves. If desired, such type-identification features can be provided in addition to color-coding of the containers in order to further simplify identification of a container's type. Providing simple visual verification of a given container's type advantageously simplifies and facilitates handling of medical waste materials throughout many aspects of collection and disposal.

In some embodiments, the containers can be configured in such a way that a sorting and disposal station can automatically identify a type of container. Such automation allows a station/machine to detect the mix and arrangement of container types in the station at any given time. In some embodiments, each container includes an identification key that can be read by corresponding structures in a sorting station. The key generally allows the sorting station to automatically identify the type of each container occupying a compartment or container position within the station. As discussed above, the station can be configured to identify container types in either a static or dynamic mode depending on a desired degree of flexibility for a given station.

Figure 13:
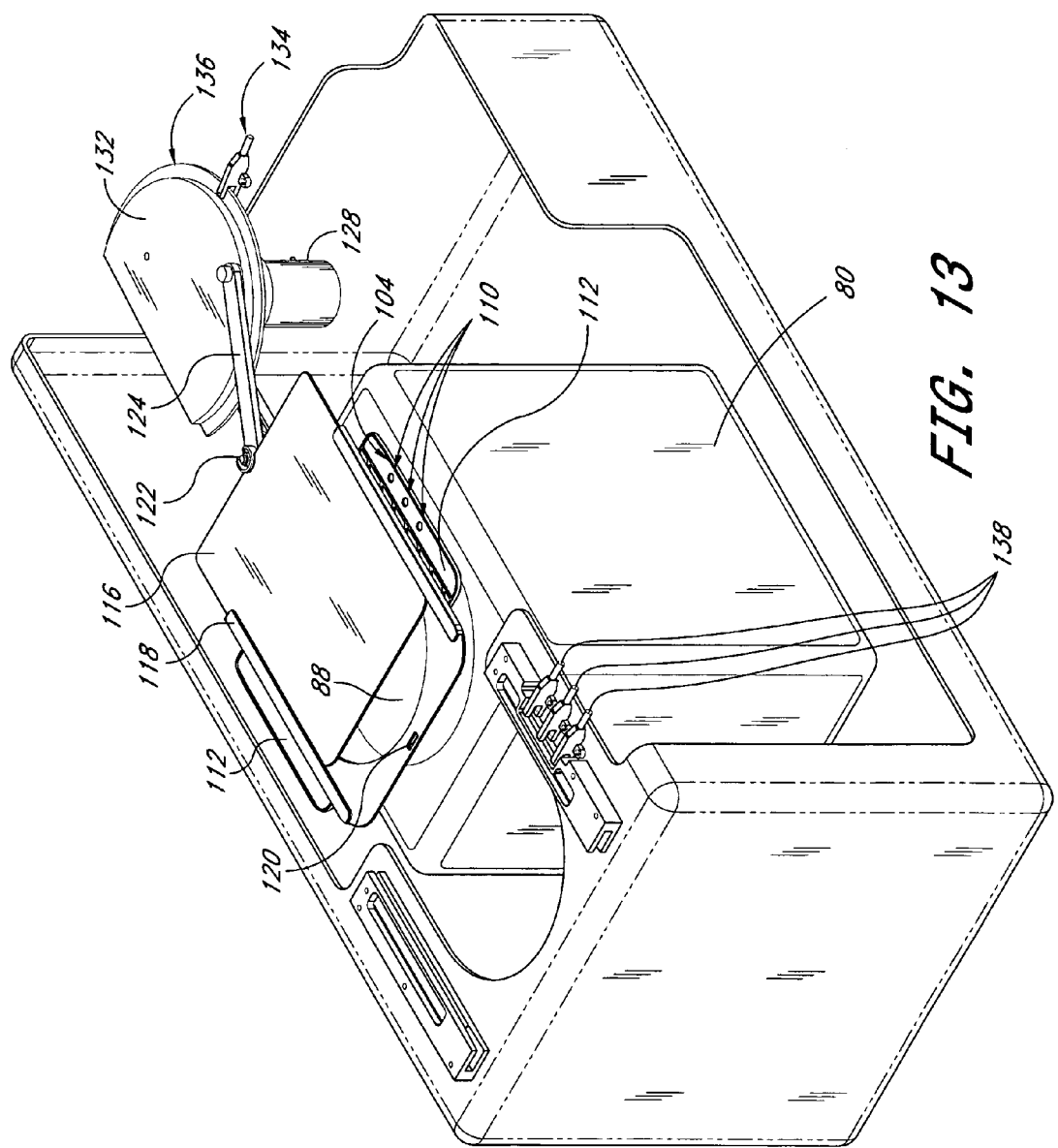
FIG. 13 is a perspective view of one embodiment of a disposable container and portions of an interface with a sorting and disposal station.
Figure 14:
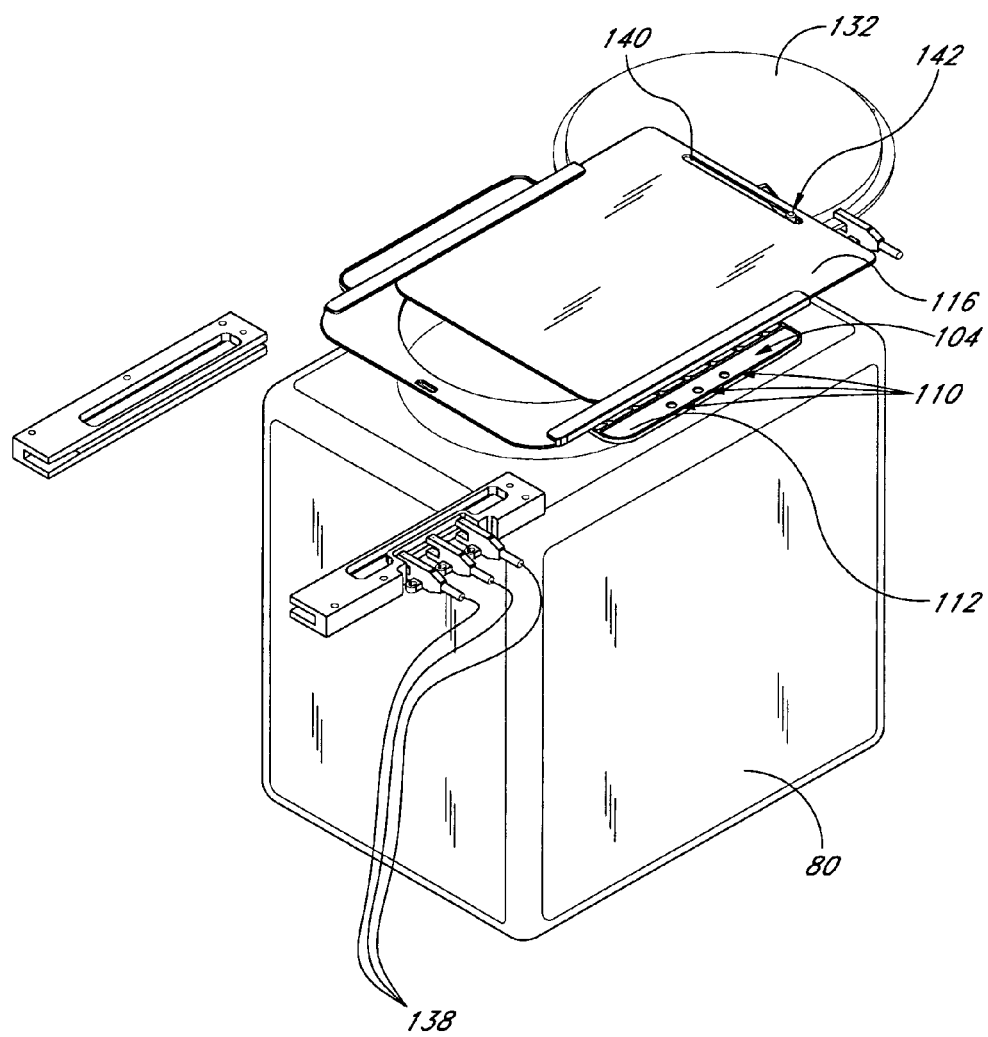
FIG. 14 is a perspective view of an alternative embodiment of a disposable container and portions of an interface with a sorting and disposal station.

Identification keys may be physical features such as fingers molded into or attached to each container. Alternatively, identification keys can be holes, notches, or grooves molded or cut into a portion of each container. In some embodiments, identification keys include optically-readable features such as holes, dark or light colored dots, text, symbols, graphics, etc. A physical key may be configured to be read by mechanical or optical switches associated with each compartment or container position within the station. For example, FIG. 13 illustrates an embodiment of a container 80 with an identification key 104 made up of a series of holes 110 in a flange 112 extending from an upper portion of the container 80. The holes 110 of FIG. 13 can be detected by a plurality of optical switches 138 mounted to a portion of the station adjacent a container position. Thus the various container types can be identified by providing holes (or other features) in varying combinations and positions.

Alternatively, a key may be an optical mark, such as a bar code, that can be interpreted by a sensor such as a bar code reader. Alternatively still, the key may be a radio frequency identification (RFID) tag that can be read by a transponder associated with each compartment. In still further embodiments, container identification keys can comprise microchips, magnetic strips, or other electronic media that can be read by a waste sorting and disposal station into which the container is placed. In one alternative embodiment, a polychromatic sensitive optical sensor can be provided to directly determine a color of a container.

As discussed above, some embodiments of a disposable container are provided with automatically operable doors. In such embodiments, a container can be closed by default to prevent insertion of items into an incorrect container. Then, once an item is scanned or otherwise identified, the station can open the appropriate container or otherwise signify the single correct container to receive that particular waste item.

FIGS. 14–17 illustrate embodiments of containers comprising integrally-formed automatically operable doors and corresponding structures in a sorting station. The illustrated structures are generally configured to provide an automated interface between a container 80 and portions of a sorting and disposal station in order to allow the station to automatically recognize and operate a container. According to these illustrated embodiments, each compartment includes an actuator mechanism configured to automatically and selectively open and close the corresponding container 80. The selective opening and closing of each container may be accomplished via interaction of structures on both the disposable container and the station, and can ultimately be controlled by a computer system within the sorting and disposal station.

In some embodiments, a container may include a movable lid molded or otherwise joined to the container opening. The lid can generally be configured to pivot, slide, hinge or rotate relative to a container in order to reveal or cover the container opening. In some embodiments, the lid is configured to mate with a mechanical actuator in the station upon installation of the container in a given container compartment. The actuator can be configured to cause the lid to open and close by translating, rotating or pivoting the lid. The actuator and lid can be further configured to separate from one another when the container is removed from the station.

FIG. 13 illustrates one embodiment of an interface between a container 80 and portions of a sorting station. In the illustrated embodiment, the container 80 comprises a gate 116 covering an opening 88 and configured to slide in tracks 118 between an open position and a closed position. The gate 116 can include a latch 120 configured to lock the container opening when the gate 116 is completely closed. When a new container 80 is inserted into a station, a drive pin 122 on the gate control arm 124 is engaged by the gate 116 of the container. The control arm 124 is configured to open and close the gate 116. The gate control arm 124 can be coupled to a drive motor 128 via a transmission element such as a disc 132 or a similarly functioning arm. If desired, a position switch 134 can also be provided on the disc 132, control arm 124, gate 116 or other component in order to detect a position of the gate 116. In the illustrated embodiment, the position switch 134 is an optical switch configured to detect one or more holes 136 in the disc 132. Additionally, the sorting station can include a plurality of optical switches 138 for detecting the presence of a container and/or the type of container 80 inserted into the sorting station. The embodiment of FIG. 14 replaces the gate control arm 124 of FIG. 13 with a slot 140 in the gate 116 in order to convert the rotational motion of the pin 142 extending from the disc 132 into linear motion of the gate 116.

Figure 15:
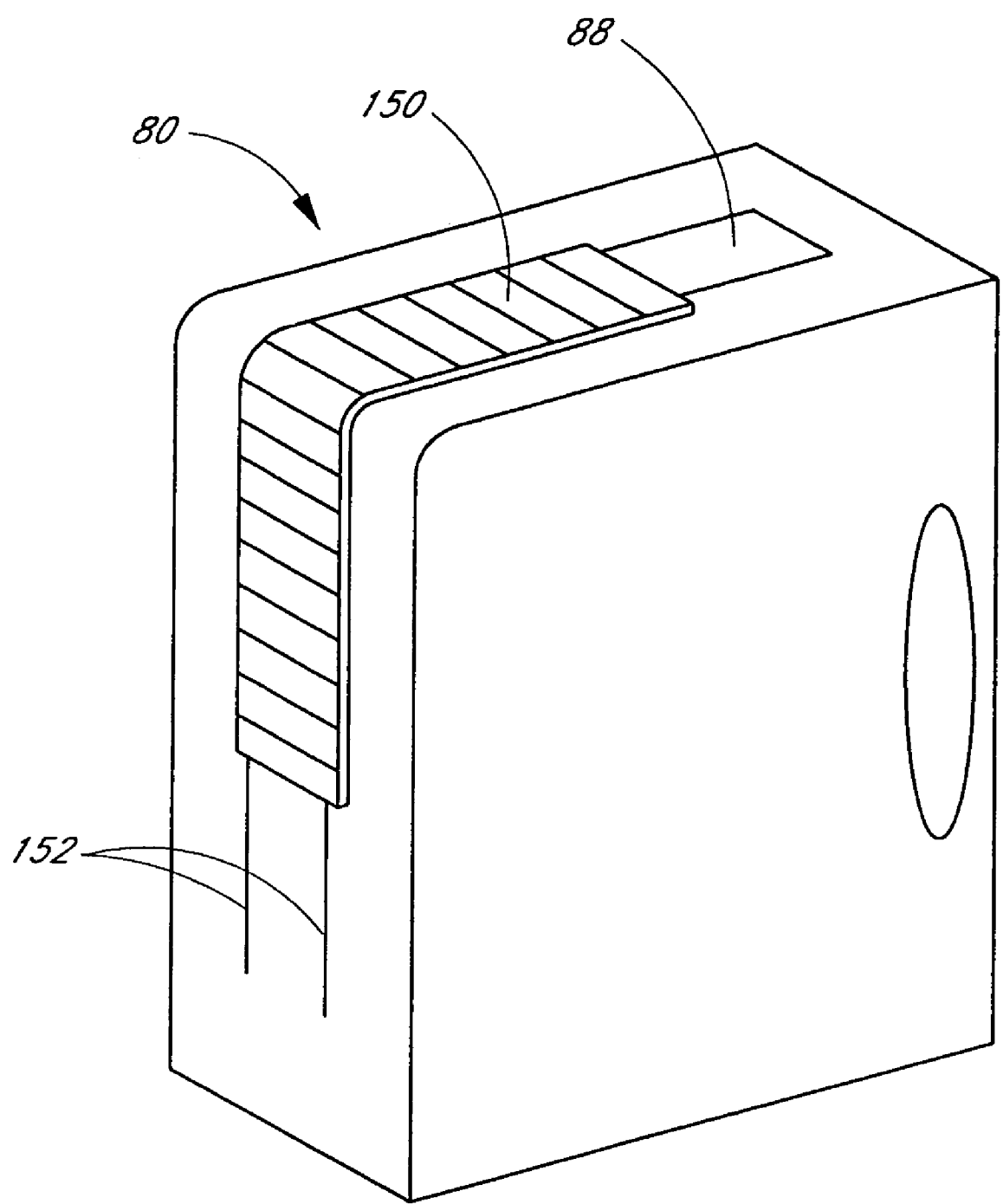
FIG. 15 is a perspective view of an alternative embodiment of a disposable container.
Figure 16:
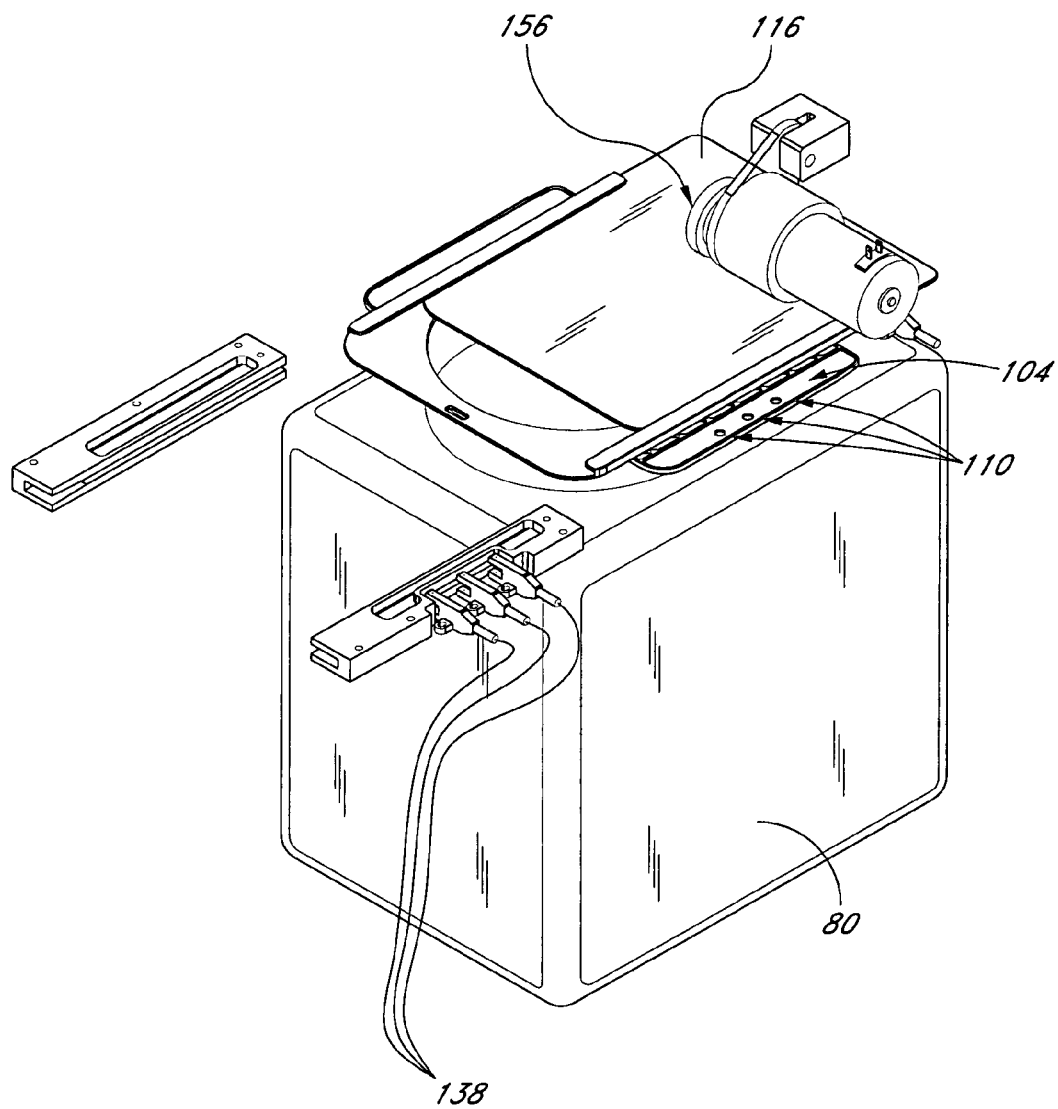
FIG. 16 is a perspective view of an embodiment of a disposable container and an alternative embodiment of portions of an interface with a sorting and disposal station.
Figure 17:
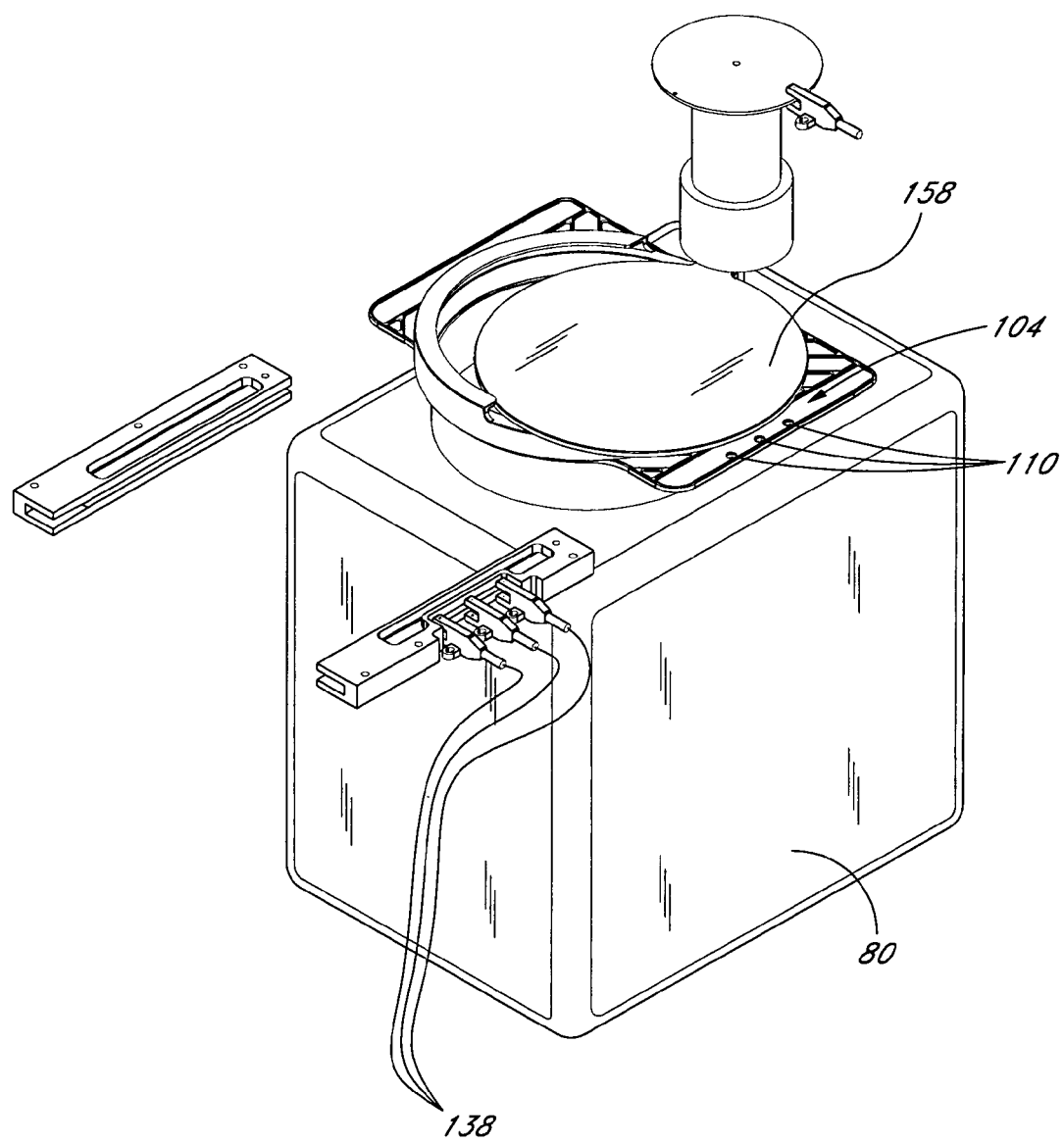
FIG. 17 is a perspective view of an embodiment of a disposable container and an alternative embodiment of portions of an interface with a sorting and disposal station.

In alternative embodiments, other configurations of automatically openable doors/gates can be provided For example, FIG. 15 illustrates an alternative embodiment of a container comprising a sectioned door 150 configured to slide along tracks 152 extending from the exterior surface of the container 80. The slidable lids of the above embodiments can be provided with a latch (such as that shown in FIGS. 13 and 14) which can be automatically engaged in order to lock the container once a sorting station determines the container is full. The embodiment illustrated in FIG. 16 can include a slidable door 116 driven by a rack and pinion drive mechanism 156. Alternatively, the drive mechanism 156 of FIG. 16 can comprise a driven friction wheel configured to engage a portion of the slidable lid 116. A similar pinion or friction wheel drive system can be used to automatically operate the sectioned door 150 of the embodiment shown in FIG. 15. FIG. 17 illustrates an embodiment of a container 80 with a lid 158 configured to open by pivoting relative to the container 80. In further alternative embodiments, a door can be opened or closed by any of a variety of other mechanisms. For example, worm screws, pneumatic pistons, hydraulic pistons, solenoids, or any other motion-transferring mechanism can be used to selectively open and close a container door.

In some embodiments it may also be desirable to provide an outer lid configured to seal a container opening once the container is full. The outer lid is preferably configured to attach to the container sufficiently securely to prevent spillage or tampering. An outer seal also shields users from contaminants that may have come in contact with the container top area during use. For example, in some embodiments a flexible lid can be configured to seal over a top of the automatically actuated door by frictionally engaging a lip, groove, or other structure in a manner similar to many flexible lids used in food storage containers. In alternative embodiments, outer seals can be provided in the form of a bag or shrink-wrap material that surrounds a substantial portion of a container's exterior.

In some embodiments, it may be desirable to provide a container configured to render waste items non-recoverable by providing a substance within an "empty" container that can react chemically with waste items. In another embodiment, a solidifying agent can be provided within a container in order to solidify non-hazardous pharmaceuticals allowing for their disposal in a landfill. In some embodiments, such solidifying agents can include materials capable of absorbing a quantity of a liquid non-hazardous pharmaceutical material. For example, such absorbent materials can include ceramic materials, sponge materials or other porous materials. Alternatively, such solidification may involve a chemical reaction between the waste material and a substance provided within the container.

Fill-Level Detection System

In some embodiments, it is desirable to measure a fill level of waste within a container throughout the sorting and filling process. In some embodiments, such fill level sensing can be performed by measuring a weight of a container, such as by using a load cell, balance, or other weight measurement device. In further embodiments, float systems can be adapted for use in determining a level of a waste material in a waste sorting system. In some cases, it is also desirable to perform such fill level measurements without the sensor physically contacting the container or the container contents.

In some embodiments, a piezo transducer can be used to determine a volume of air remaining in a container by conducting a frequency sweep of the transducer to determine the resonance of the air in the container. Once the volume of air in the container is known, the air volume can be subtracted from the known total container volume to obtain the volume occupied by the container contents. In another alternative embodiment, a distance-measuring sensor (such as SONAR, RADAR or optical distance-measuring sensors) can be located above and directed through the opening of the container in order to determine a "height" of the container contents. In another embodiment, a sensor can be provided for determining whether a container includes any waste at all. Such a "waste presence" sensor can be used in combination with a timer to determine a replacement schedule for a particular container based on a maximum acceptable dwell time for a particular waste item in a container. Still other embodiments may use optical sensors to measure a fill level of a container.

Figure 18:
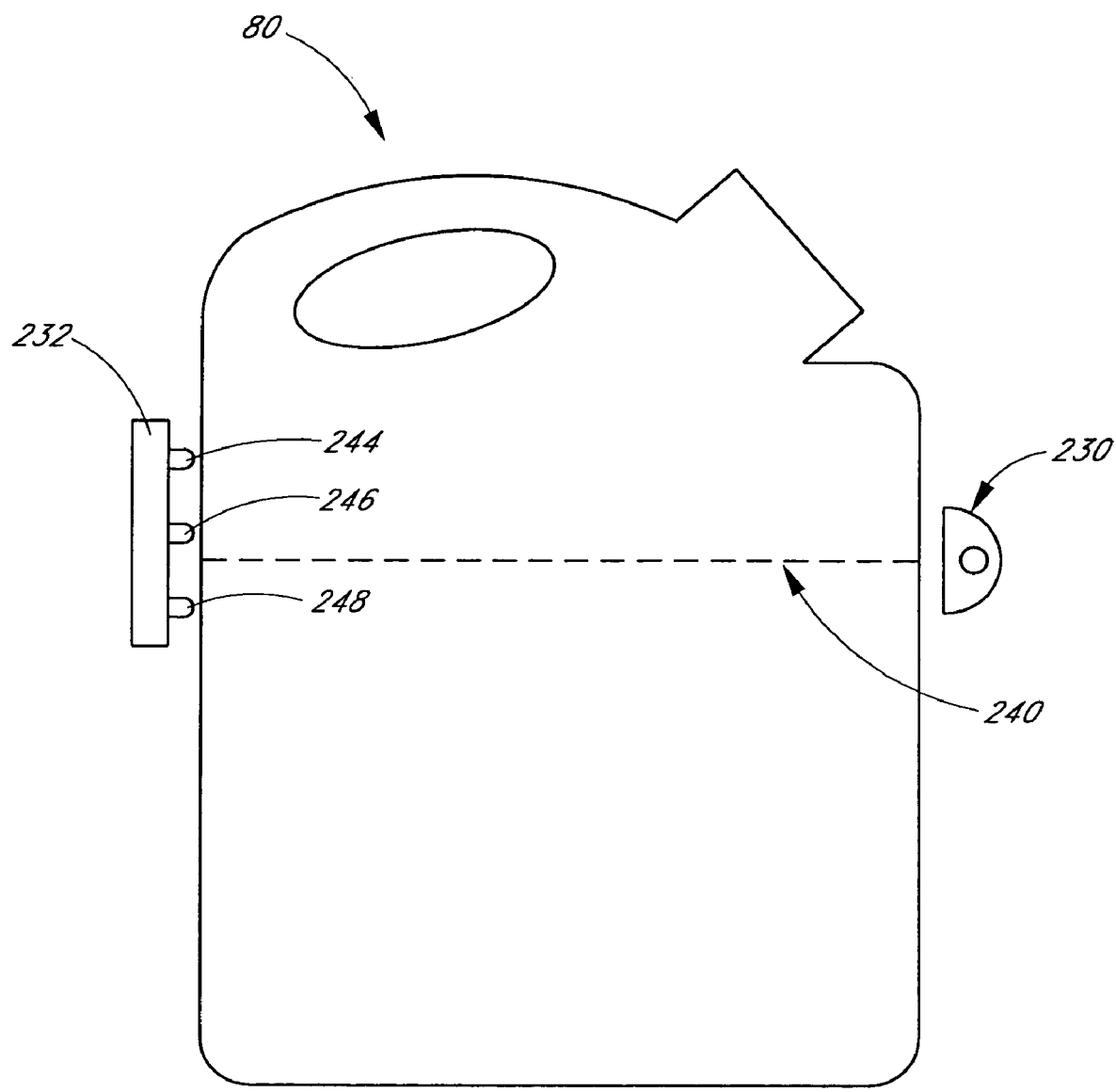
FIG. 18 is a schematic side elevation view of an embodiment of a fill level sensor.
Figure 19:
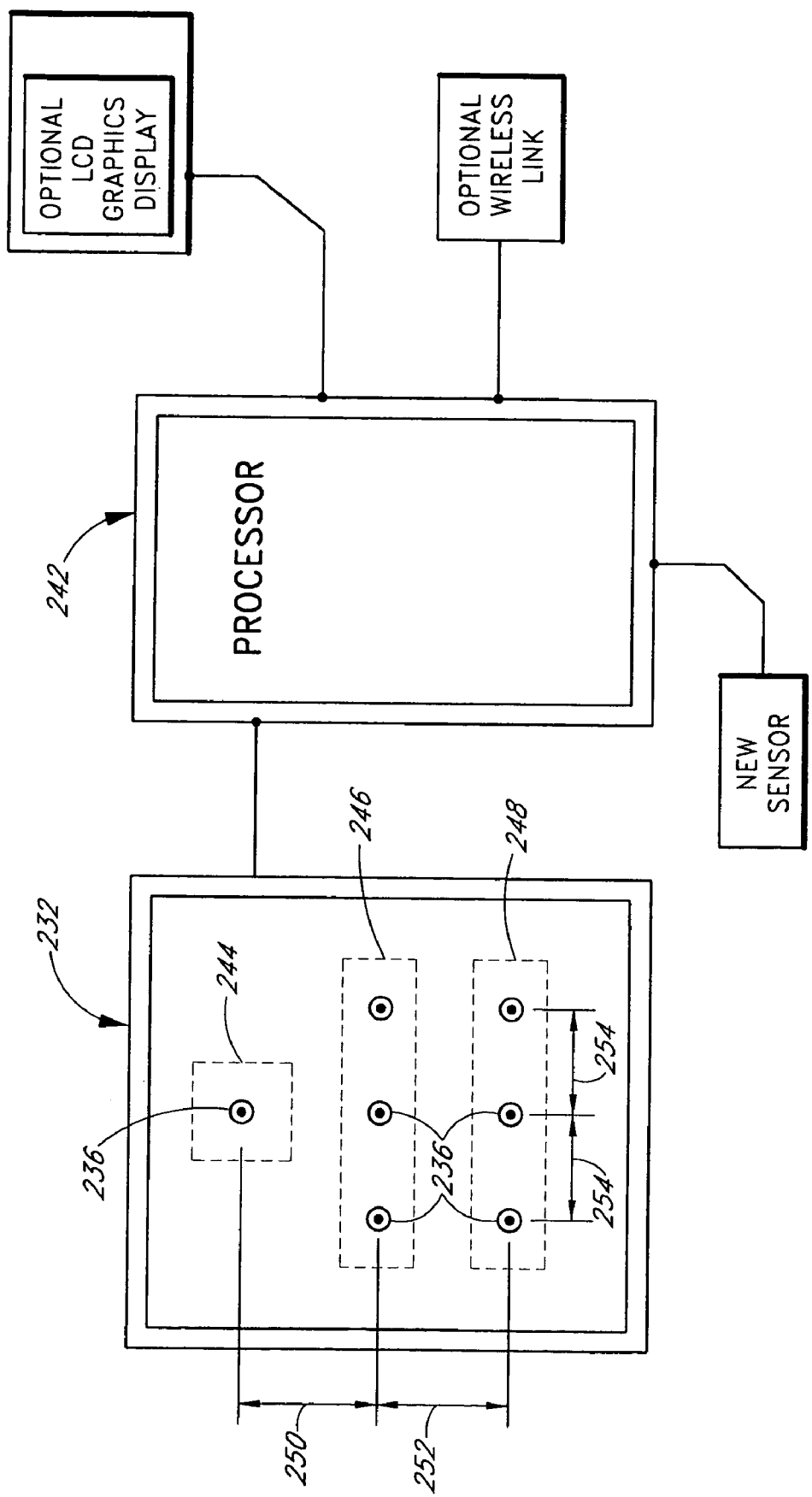
FIG. 19 is a block diagram of one embodiment of a fill-level detection system.

FIGS. 18–19 illustrate one embodiment of a level sensor which can be used to automatically determine a fill level of a container using an optical method. As shown in the schematic illustration of FIG. 18, one embodiment of a fill level sensing system comprises a light source 230 and a light detector 232 positioned on opposite sides of a disposable container 80. In alternative embodiments, the light detector 232 need not be located immediately opposite the light source, for example, in some embodiments the detector can be located on a wall adjacent to the source 230. The sensor system of FIGS. 18 and 19 generally operates on the principle that an "empty" container will permit more light to pass from the source, through the container, and to the sensor than will a "full" container. This is simply due to the fact that the contents of the container 80 will absorb and/or reflect a substantial portion of the light which enters the container from a light source.

As used herein, the terms "empty" and "full" shall be given their ordinary meaning and shall be used to define relative amounts of debris, or other matter, in a container. For example, in certain embodiments, the sensor may indicate that the container is ready to be emptied or discarded, not because it is completely saturated, but because it has reached the desired point of fill or saturation. In some situations, it may be desirous to empty or remove a container when anywhere from about 1% to about 100%, often from about 25% to about 100% of that container contains waste material. In other situations, it may be desirable to remove a container when about 50% to about 95% of its volume is occupied by waste material.

In some other embodiments, a parameter other than weight or filled volume may be used to determine when a container is "full." For example, in one embodiment, a sensor to detect radioactivity is used to determine the amount of radioisotope in a container or receptacle. The radioactivity sensor may used in connection with a fill sensor, or it may be used alone. Thus, in some embodiments, a container may be emptied, discarded, or replaced based on a certain amount of radioactivity, rather than (or in addition to) the surface area, volume, weight, density and/or another parameter of the material in that container.

In yet another embodiment, a sorting and disposal system can be provided without any automatic level detection apparatus. For example, in such an embodiment, the containers can be configured to allow a clinician, maintenance person, or other user to visually verify a fill level of the container. In such embodiments, the containers can be made of a substantially transparent or translucent material. Alternatively, the containers may be substantially opaque but can include a transparent viewing window to allow visual verification of a fill level. Such viewing windows could extend substantially an entire height of the container, or could extend only a height of a desired portion of the container.

In some embodiments, the source 230 and detector 232 are located along a "fill line" which generally defines a "fill plane." The fill plane 240 is generally the level within the container 80 which a processor 242 defines as "full." In some embodiments, the actual free surface of contents within a container may not necessarily be planar. In such embodiments, the "fill plane" used by the processor and fill level sensing system is simply an average height of the material.

In the embodiment illustrated in FIG. 18, a light source 230 is located at a "front" of the container and a detector 232 is located at a "rear" of the container. In alternative embodiments, the positions of the light source 230 and detector 232 can be reversed, or positioned at any other position around the container 80. In still further embodiments, multiple sources and/or detectors can also be used as desired.

As discussed above, the containers 80 are typically made of a translucent material which allows at least some amount of light to pass through its walls. The embodiments of a fill level sensor illustrated in FIGS. 18 and 19 are particularly advantageous when used to measure a fill level of a container with translucent sidewalls. However, the skilled artisan will recognize that certain advantages of the embodiments described herein may be advantageously applied to systems using containers having transparent sidewalls or containers with transparent windows in otherwise relatively opaque sidewalls. As used herein, the term "translucent" is used in its ordinary sense and refers without limitation to a material which allows the diffuse transmission of light when illuminated, while remaining substantially non-transparent when not illuminated.

The light source can comprise any suitable source of light such as incandescent bulbs, white or colored LED's, or other sources. In some embodiments, the light source 230 is located such that it is vertically centered on a desired "fill line" 240 of the container. The light source can be laterally centered relative to the container, or can comprise a width that is about as wide as the container 80. In still further embodiments, a plurality of light sources can be used to illuminate a container from multiple points.

As illustrated in FIG. 19, the light detector 232 can comprise an array of photo detectors 236 such as cadmium sulfide photo detectors or photodiodes. In the illustrated embodiment, the array of photo detectors 236 comprises three rows 244, 246 and 248 of detectors 236. The upper row 244 contains a single detector 236 while the middle 246 and lower 248 rows contain a plurality of detectors 236 (three in the illustrated embodiment). In alternative embodiments, the upper row 244 can be provided with additional detectors which equal or exceed the number of detectors in the other rows. Similarly, the middle 246 and lower 248 rows can include fewer or more than three detectors as desired. The number of detectors in each row will typically be determined by the algorithm used to determine the fill level of the container and/or the degree of accuracy desired. In some embodiments, it may also be desirable to provide more than three rows of detectors. For example, in some embodiments, a fill level detection system can be provided with four, five or more rows of detectors.

In some embodiments, the middle row of detectors is positioned to lie just above the fill line 240 of the container 80, and the lower row 248 of detectors 236 is positioned just below the fill line 240. The upper row 244 of detectors 236 can be located substantially above the fill line, and can be used to calibrate the detectors middle 246 and lower 248 rows as will be described in further detail below.

In some embodiments, the upper and middle rows can be spaced by a distance 250 of between about ½" and about 2 inches, in other embodiments the upper and middle rows can be spaced by a distance 250 of between about 1 inch and about 1½ inches, and in one particular embodiment, the upper and middle rows are spaced by a distance 250 of about 1¼ inches. Similarly, the middle and lower rows can be spaced by a distance 252 of between about ½" and about 2 inches, in other embodiments, the middle and lower rows can be spaced by a distance 252 of between about 1 inch and about 1½ inches, and in one particular embodiment, the middle and lower rows are spaced by a distance 252 of about 1¼ inches. In some embodiments, the detectors 236 of the middle 246 and lower 248 rows are spaced horizontally by a distance 254 of between about ½ inch and about 3 inches, in other embodiments, the detectors 236 of the middle 246 and lower 248 rows are spaced horizontally by a distance 254 of between about 1 inch and about 2 inches, and in one particular embodiment by a horizontal distance 254 of about 1½ inches. In some embodiments, the sensors are evenly spaced, while in other embodiments, the sensors of the middle row are horizontally spaced differently than the sensors of the lower row. In further alternative embodiments, the spacing of the detectors 236 can be determined by factors such as the size of the container or the material to be placed within the container.

In operation, the individual photo detectors 236 pick up light transmitted through the container and output corresponding signals to a processor 242. On one hand, the light intensity arriving at the detectors 236 depends on the fill level of the container 80. In addition, a number of secondary factors also effect the light intensity reaching the detectors 236. These include the strength of the light source 230, the color and opacity of the container 80, the amount of ambient light, and other factors such as dust in the air. The light intensity at the top detector row 244 is almost completely governed by these secondary factors, since it is located well above the fill line 240. By contrast, the light intensity arriving at the middle 246 and lower 248 detector rows will be effected more by the fill level of the container contents as the container 80 becomes more full (e.g., as the fill level approaches the fill line).

When the container 80 is empty and the overall light intensity is greatest, a baseline reading is recorded and calibration coefficients are generated for each of the detectors 236 and detector rows 244, 246, 248. As the container fills, the received light reaching the detectors decreases slightly as material in the container blocks a portion of the diffused light transmitted through the container 80. During this phase, the top detector reading is used to compensate the readings of the middle and lower detector rows accordingly. When the container contents reaches the fill line, the bottom row of detectors will be blocked by the container contents, while the middle 246 and upper 248 detector rows remain unobstructed. This results in a substantial drop in the light intensity reaching the bottom row 248 of detectors, and correspondingly, a substantial difference in signal strength between the middle 246 and lower 248 detector rows. When this signal difference reaches a pre-determined threshold level, the processor determines that the container is "full."

In some embodiments, the items being deposited into a container may be stacked unevenly or oddly oriented within a container so that the contents of a container vary from a neat horizontal fill level. For example, some large items, such as syringes or other contaminated medical devices, may stack oddly within a container, thereby creating voids of unfilled space in a central portion of a container, above which waste items may be stacked. Such variations in filling can lead to lead to measurement errors. Thus, in some embodiments, a level sensing system can be provided with error processing capabilities to account for variations in orientation and/or uneven loading of a container.

For example, in some embodiments, the signals from the plurality of detectors in each row are averaged to provide a consensus value for the respective detector row. This advantageously allows the processor to determine an average fill level in the event of an uneven fill surface. For example, in an idealized case, a container filled with a plurality of spherical particles through a hole in the top center of a regularly-shaped container will typically have a free surface in a shape of a cone with a peak at the center, and dropping off evenly in each direction. In such a case, the center detector of the lower row 248 will typically receive a lower light intensity than the detectors on either side. Thus, by using the data from all of the detectors in a horizontal row, a processor can calculate an approximate average fill level in order to prevent over-filling of the container.

These or other error-processing techniques can also be used to compensate for manufacturing defects in a container that might result in erroneous results. For example, if a plastic container wall comprises an air bubble or a dark spot in a region adjacent one or more of the detectors, these abnormalities could cause erroneous readings by those detectors. To compensate for this, a system may give less weight (or no weight at all) to signals from detectors that are out of a statistically expected range of variation from the remaining detectors. By taking an average signal across all detectors in various combinations and/or by assigning varying weights to individual detectors, a control algorithm can teach itself to recognize and adapt to such error-causing situations in order to obtain consistent readings.

In some embodiments, the functionality of a fill level sensing system employing a light source and a plurality of optical detectors can advantageously be enhanced by containers with "frosted" or translucent walls. Another advantage of certain embodiments of a level sensing system as described herein is that such systems can be polychromatic sensitive (i.e. configured to sense light of various colors with consistent accuracy). Thus, in addition to measuring a fill level of a container, the above-described sensors can be configured to determine a color of a container (each container color being associated with a particular container type as discussed above). In some embodiments, these and other advantages are achieved through the use of cadmium sulfide photosensitive cells. In alternative embodiments, optical level sensors can be constructed using other optical detectors, including other photoconductive cells, photo diodes, or other sensors capable of detecting light in the visible or infrared spectrum.

In some embodiments, each one of a plurality of fill-level sensors is controlled by a single processor in a waste sorting system. In one embodiment, a plurality of photo detector arrays can be connected to a single multi-channel bus, and a plurality of light sources can be controlled by a processor. In this embodiment, the processor can illuminate a single container at a time. Thus, the detectors behind each of the "dark" containers would be at high impedance, and would therefore be out of the circuit.

In some embodiments, a fill level sensing system employing optical sources and detectors can include an additional photo detector that is generally configured to measure changes in "ambient" light within the system in order to appropriately adjust the readings from the detector arrays measuring fill level. An ambient light detector can comprise a single optical detector, or a plurality of detectors in a circuit. In one such embodiment, an additional ambient light detector is provided within a waste sorting system in a location selected to measure any light entering the system from the exterior of the sorting system. For example, the ambient light detector can be located adjacent a container-replacement door or any other portion of the system that is open to external light.

FIG. 22A illustrates one embodiment of a circuit schematic which can be used in building an optical fill level sensor such as that illustrated in FIGS. 18 and 19. The skilled artisan will recognize that this is merely one exemplary schematic, and that alternative embodiments of the system of FIGS. 18 and 19 can be built using any appropriate components.

Figure 20:
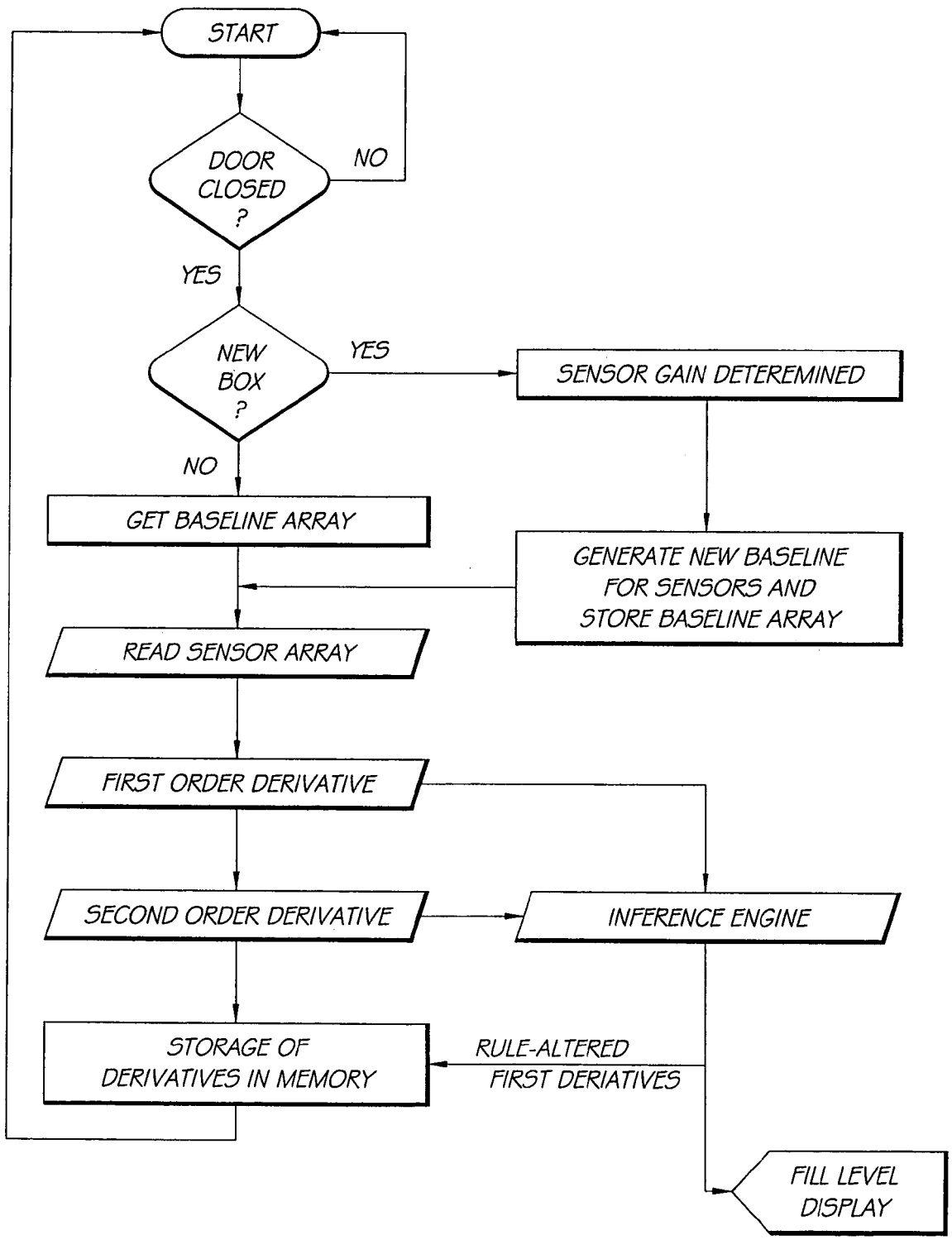
FIG. 20 is a an overview flow chart of one embodiment of a software algorithm for measuring a fill level of a container.
Figure 21:
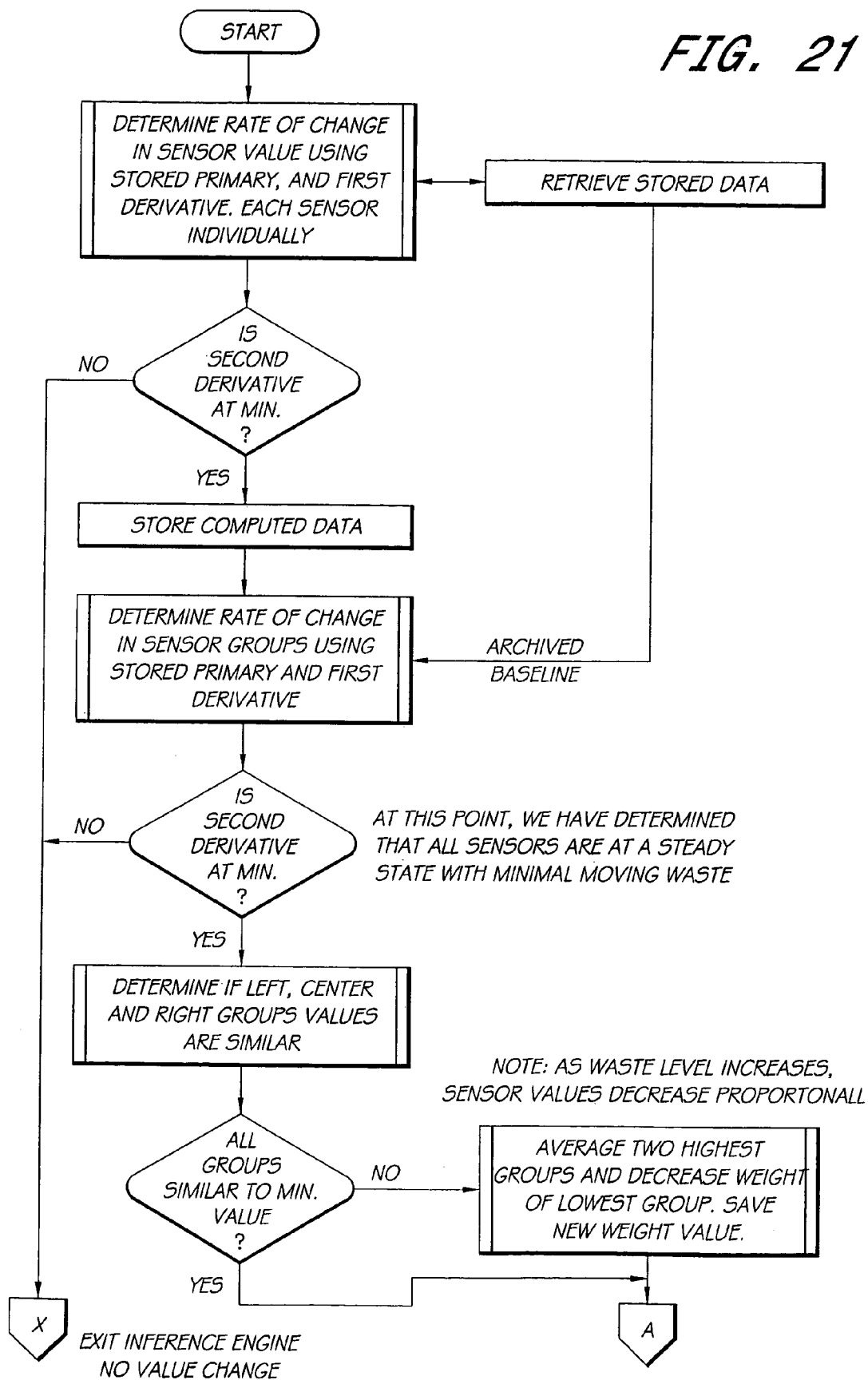
FIG. 21 is a detailed flow chart of one embodiment of a method of measuring a fill level of a container
Figure 22:
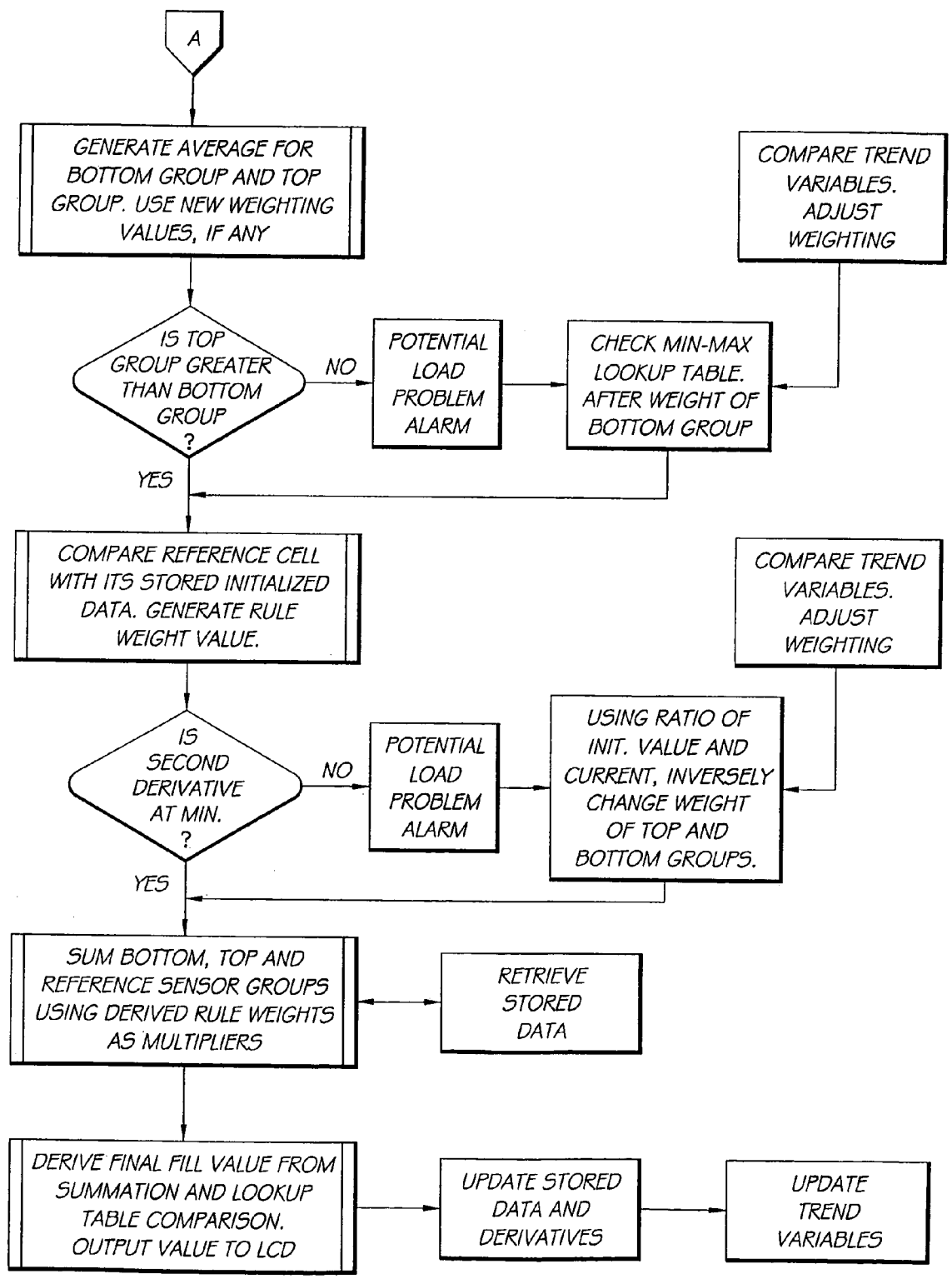
FIG. 22 is a continuation of the flow chart of FIG. 21.

FIGS. 20–22 are flow charts illustrating embodiments of software algorithms used by a level detector for use in a sorting system. FIG. 20 is a flow chart illustrating an overview of a level testing algorithm. When the system determines that a new container has been inserted, the level sensor establishes new baseline values for the detectors in order to define the "empty" state. The level sensing system then reads values of the detectors 236 and inputs the detector values to an inference engine (FIGS. 21 and 22).

The inference engine can use a "fuzzy logic" method similar to the Sugeno method. In one embodiment, the inference engine uses a table of empirically-determined data to establish rule weights. The inference engine can also use multiple grouping of detectors in addition to individual detector levels to calculate a final fill level of the container. In some embodiments, the empirically-determined lookup table can be developed by performing various calibration experiments using an optical level sensing system to measure containers at known fill levels. In addition to any controlled experiments, the lookup table can be supplemented by analysis of information it receives during use in measuring fill levels of new containers. For example, as optical anomalies are detected and accounted for, the software can adapt to correct for them.

FIGS. 21 and 22 are flow charts illustrating one embodiment of an inference engine. In order to avoid misleading readings during filling, the system can be configured to determine when the detectors are at a steady state (e.g., when the movement of waste within the container drops below a threshold level). This is particularly helpful in embodiments in which a waste material is a liquid, and thus may continue moving for a period of time.

Once steady state is reached, the inference engine compares the values of the detector readings and ultimately derives a final fill value which can be stored and/or output to a user-readable device such as a liquid crystal display. In alternative embodiments, an output of the system can include other visible, audible or tactile alerts, such as LEDs, buzzers, bells, vibrators, etc. In some embodiments, an output signal is used to notify the user that a particular container is ready to be emptied, discarded, replaced etc. In an alternative embodiment, an output signal is provided substantially continuously or at various intervals, so that the user can determine or monitor the amount of material in a given container at any given time. For example, in some embodiments, the fill-level of a container can be measured at regular intervals, such as every ten minutes, every hour, every two hours, every six hours, every 12 hours, or every 24 hours. In still further embodiments, the system can comprise a sensor (such as an optical sensor) to determine when an item is deposited into a container. Then a fill-level of the container can be measured after each item is deposited in the container.

Figure 23:
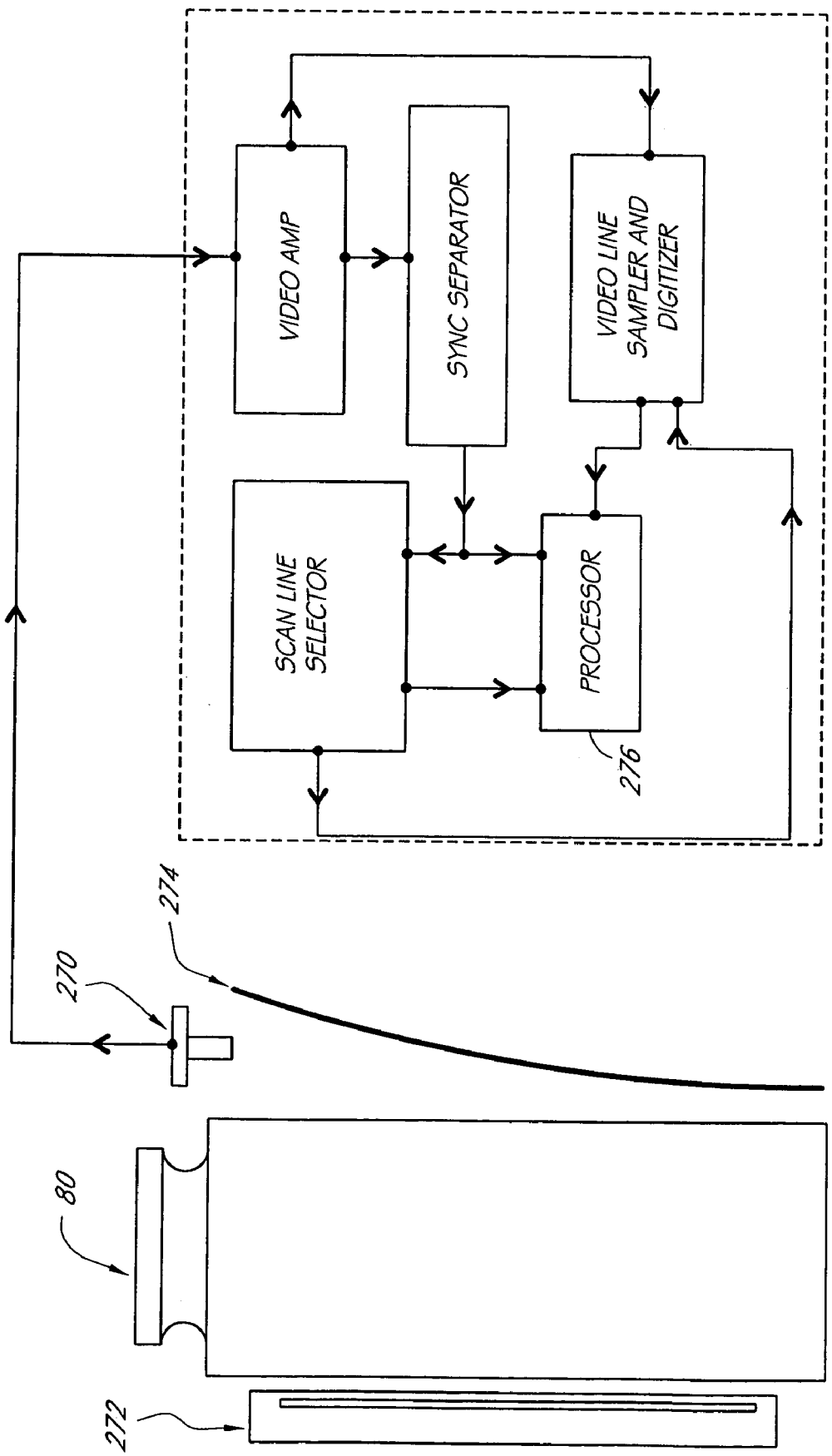
FIG. 23 is a block diagram of an alternative embodiment of a level sensor system employing a video camera.

FIG. 23 illustrates an alternative embodiment of a video fill level sensing system. The embodiment of FIG. 23 employs a camera 270 to continuously detect an intensity of light exiting the container from the source. In the illustrated embodiment, a light source 270 is positioned to illuminate the container 80, and a curved mirror 274 and pinhole video camera are located adjacent another side of the container 80. The system can also include a software-based processor 276 and other electronic hardware. In the illustrated embodiment, the light source 270 is located adjacent one vertical side of the container 80 and the camera and mirror are positioned on the opposite side of the container. In alternative embodiments, the light source 270 and camera/mirror assembly can be located on adjacent sides of the container 80. Alternatively still, the light source 270 can be located above the container such that light is directed downward into the container, thereby allowing the waste to absorb as well as reflectively diffuse the light source onto the walls of the container 80.

In some embodiments, the camera 270 is directed at the mirror 274 to detect light emitted from the container 80 and gathered by the mirror 274. The curved mirror 274 provides a linearization of scanline width by distorting the optics of the camera. In one embodiment, the camera 270 is a pinhole camera, which is selected due to the depth of field this type of lens provides. In one embodiment, the curved mirror 274 has a shape substantially similar to a shoehorn, e.g., it is curved about two perpendicular axes (e.g., longitudinal and transverse axes). Alternative mirror configurations can also be used as desired. The particular curvature of the mirror 274 is determined empirically depending on the width of scanline needed and the height of the measured area (e.g., the height of the container wall). Variation in the curvature of the mirror along its length allows the scanline to be optimized in order to emphasize areas of higher interest and to de-emphasize lower interest areas. The mirror can be convexly curved at the height of higher interest areas, and concavely curved to de-emphasize lower interest areas.

In some alternative embodiments, the light source can include bands of varying color or intensity along the height of the container in order to provide emphasis to portions of the container, or to provide "watermark" levels that can be measured against. In some embodiments, the software can be configured to interpret information received from the camera to learn about points of interest in order to further optimize a measurement algorithm. For example, rather than programming an algorithm to anticipate areas of higher or lower interest, the algorithm can be configured to recognize variations in light intensity during calibration in order to detect such areas of higher or lower interest.

Figure 23A:
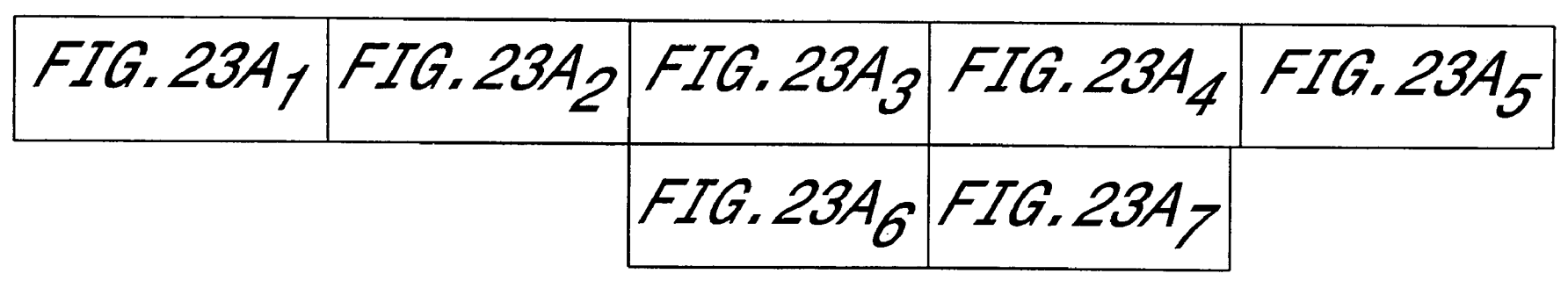

The processor and its support hardware provide the sampling of multiple luminance intensities along the wall of the container 80 adjacent the mirror 274. The analog video signal is amplified and ground-referenced by the video amplifier. This amplified signal is scanned for a selected scanline to digitize for quantifying its luminance value. The amplified video is also applied to the Sync Separator module, which produces timing pulses for the scanline selector module. The processor receives the scanline data from the scanline selector, digitizer and sync separator. The video level sensor can determine a current fill level of the waste in the container 80 using a similar software method to that described above with reference to FIGS. 18 and 19. FIG. 23A illustrates one embodiment of a circuit schematic which can be used in building a video fill level sensor such as that illustrated in FIG. 23. The skilled artisan will recognize, however, that this is merely one exemplary embodiment. In alternative embodiments, the system of FIG. 23 can be built using any appropriate components.

Many of the above embodiments of fill level sensors were described with reference to a single disposable container. In some alternative embodiments, it may be desirable to provide a single fill level detection system configured to selectively measure a fill level of any one of a plurality of containers. For example, in one embodiment, a light source may be provided on a first side of a plurality of containers, and a light detector can be movable into a position opposite the light source of the containers. In one embodiment, this may take the form of a circular arrangement of containers in which a light detector is located at a center of a circular arrangement of containers. One or more light sources can be positioned on an outer portion of the circular arrangement such that the light source and/or the light detector is capable of measuring a fill level of each one of the plurality of containers around the circle.

In some embodiments, the sorting system can also include a weight scale (such as a load cell, pressure transducer, mechanical scale or other device) configured to weigh either a single spent drug, container or individual segregated spent drugs. In one embodiment, the information from the scale can be sent to a printer providing a means for printing a manifest for the container. Additionally, such information could be combined with other information available to a clinician in order to determine a quantity of a drug or substance that has been used or consumed. Many hospitals are automating the dispensing of drugs. The automation is usually embodied in a piece of equipment that a doctor or nurse accesses with a patient and clinician code and the correct amount of drug is dispensed. The automation provides pharmacists, nurses, doctors and administrators with information from a database on what drugs are dispensed and to which patient. These systems can typically indicate how much of a drug was administered, but entering this information typically requires a clinician to return to the dispenser (which may be inconvenient, and thus not done regularly). This information can be quite useful because it will demonstrate any inefficiencies or mistakes in administrating the drugs as well as point out any theft of drugs. In some embodiments, a sorting and disposal system can be configured to track dispensing information because at the point of throwing the spent drug away, they are automatically providing information to a central database.

Sorting Algorithm

Embodiments of a pharmaceutical waste sorting and disposal system will generally employ a waste sorting algorithm to assign each item of waste to a particular waste category and correspondingly to a particular waste container. A waste sorting algorithm can take a variety of forms, and can include a range of functionalities.

In some embodiments, as discussed above, determination of the waste categories themselves can depend on a number of factors, including RCRA hazardous waste definitions, state and federal EPA regulations, OSHA regulations, and any institution-specific regulations. For example, RCRA definitions generally include a P list, a U list and four characteristics of hazardous waste: ignitability, corrosivity, toxicity and reactivity. Materials exhibiting each of these characteristics typically call for different handling, treatment and/or disposal. Thus, in some cases waste categories can be defined based on groups of materials that require the same or similar handling, treatment, or disposal. However, in some cases, two materials that may be handled and/or treated in a similar manner might react adversely if they are combined with one another. Thus, in further embodiments, determination of the waste categories can also depend on the combinability of materials exhibiting one or more of the above characteristics.

Once a series of unique waste categories is established, lists of known pharmaceuticals, chemicals, materials and waste items can be selectively assigned to at least one of the waste categories. In some embodiments, as discussed above, when a waste item is presented to a sorting station, the item is identified according to a waste item identifier. Such identifiers can include a trade name, a generic name, a National Drug Code (NDC), one or more components or ingredients of the item, or any other sufficiently unique or relevant waste-identifying datum. Thus, a category database can be developed which correlates a number of known waste identifiers with respective waste categories according to existing federal, state, local, institution-specific or other rules and regulations.

In some embodiments, it may also be desirable to provide a database which lists ingredients of a plurality of known pharmaceuticals or other chemicals that have not yet been correlated to a waste category by the category database. Such an ingredient database can be used by the sorting algorithm in an intermediate step between identifying an item and assigning the item to a category on the basis of one or more ingredients. In some embodiments, an ingredient database may reside within the waste sorting and disposal system. In alternative embodiments, an ingredient database can reside at a remote location, such as on a server operated by a manufacturer of a particular item, or another remote location. The waste sorting and disposal system can be configured to access such remote databases via any available network, including the internet.

In some embodiments, on a first level, assignment of waste items to waste categories can be performed simply by sorting the items according to known characteristics. In some embodiments, a waste sorting algorithm simply involves locating a waste item identifier in a look-up table or database which lists known identifiers correlated to respective waste categories, such as the category database described above. Thus, to the extent that an item can be assigned to a waste category based solely on one or more waste item identifiers, the sorting algorithm can comprise a simple look-up routine. If needed, the sorting algorithm may also seek additional information such as from the ingredient database described above, or any other available source of additional information.

Cases may arise where a single waste item possesses two or more waste identifiers (such as ingredients) belonging to two or more different waste categories. Thus, in the event that a particular waste item can reasonably be assigned to two or more waste categories, yet is only physically capable of being placed in a single container, the waste sorting algorithm can be configured to assign the item to a single category by reviewing a number of secondary variables. Such secondary variables may include a dosage or quantity of specific ingredients; a dilution or concentration level of one or more ingredients; a relative hazardousness level of one or more specific ingredients; a relative reactiveness of one or more ingredients; a shape, size, type or other feature of a waste item container (e.g., a pill bottle, syringe, etc); a physical property of the item (e.g., liquid, solid or gas), or any other datum that may be available to a user, but that might not be automatically determinable by the sorting station. If such a piece of additional information is needed in order to complete an assignment of an item to a container, the sorting station can prompt a user to input further information. Such additional information can be input by selecting from multiple answer choices or by typing.

Figure 24:
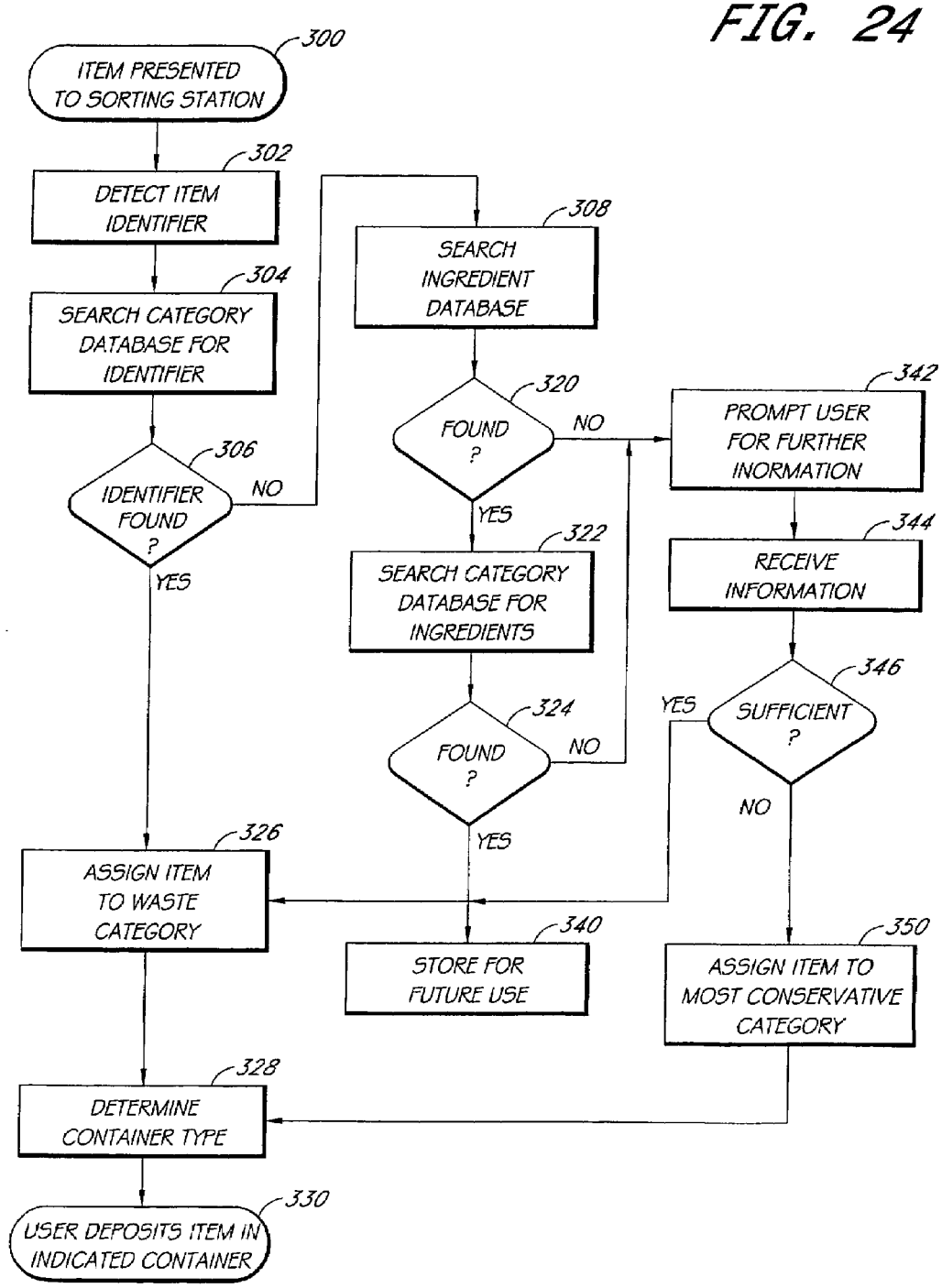
FIG. 24 is a flow chart illustrating one embodiment of a sorting algorithm for use by embodiments of a medical waste sorting and disposal system.

FIG. 24 is a flow chart illustrating one embodiment of a sorting algorithm. In the illustrated embodiment, a user initiates the process by presenting 300 a waste item to be identified by the sorting station. The sorting station then detects 302 a waste item identifier in any manner discussed above, such as scanning a barcode, reading an RFID tag, or scanning a textual or graphic label. The system then searches 304 the category database using any information or identifier determined from the item in an attempt to discover whether the determined identifier has previously been correlated to a waste category. If the identifier is found 306 to have been correlated to a waste category, the system continues by assigning the item to the appropriate waste category, and facilitating disposal of the item in the appropriate container.

On the other hand, if the identifier is not found in the category database (e.g.,. if the system discovers that the determined waste item identifier is insufficient to determine an appropriate waste category), the system may search an ingredient database 308 for additional information or further details about the item. If additional information is found 320 in an ingredient database, the additional information, along with the originally-detected waste item identifier can be used to again search the category database 322. If this information is found to be sufficient 324 to assign the item to a waste category, then the system assigns the item 326 to that category, determines an appropriate container 328 and facilitates disposal 330 of the item in a container associated with the assigned category. The system can also store 340 the identifier/category assignment combination in the category database for use in accelerating the sorting of future waste items with the same identifier.

However, if the search of the ingredient database yields insufficient information to assign the item to a waste category, the system may seek additional information by prompting a user 342 to input additional information. Such a prompt may request specific information, such as a choice between known alternatives, or may be more general in nature. The information received 344 from the user can then be combined with previously-obtained information about the item, and the category database can again be searched in an attempt to assign the item to a category. If this information, in combination with the previously-obtained information, is sufficient to assign the item to a waste category 346, then the system assigns the item 326 and facilitates disposal 330 of the item in the appropriate container. As above, the system can also store 340 the identifier/category assignment combination in the category database for use in accelerating the sorting of future waste items with the same identifier.

If the information received 344 from the user is insufficient 346 for the system to make a category assignment, the system can either prompt the user for still more information 342, or the system can simply assign 350 the item to the most conservative waste category for disposal of the item as hazardous waste.

Figure 25:
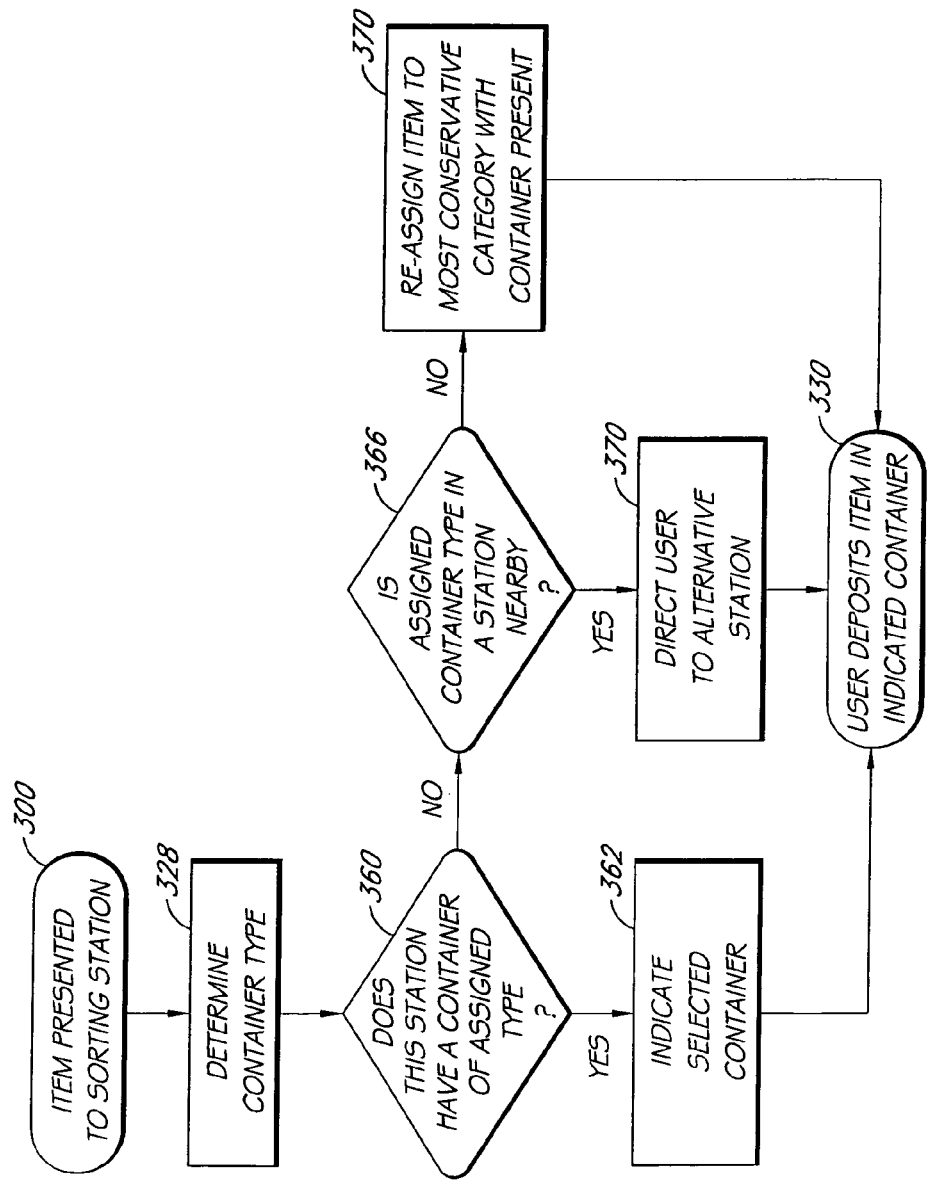
FIG. 25 is a flow chart illustrating a container-checking subroutine for use by embodiments of a medical waste sorting and disposal system.

FIG. 25 illustrates one embodiment of a portion of a sorting algorithm which can be used in determining the best container for a particular item. Once the sorting algorithm has assigned an item to a waste category, the system determines 328 the container type associated with the assigned waste category. In the illustrated embodiment, the station searches the stock of the containers currently loaded into that station to determine whether the assigned container type is present in that particular sorting station 360. If the container type is present, the station proceeds to indicate 362 the appropriate container to the user, and the user may then deposit 330 the item into the selected container. However, in some embodiments, if the selected container type is not present, the station can assess 366 whether another sorting station nearby contains a container of the assigned type. If a station with the selected container is nearby, the system can direct the user 370 to the nearby station to deposit the item. If a station with the selected container type is not nearby, the system can re-assign 368 the waste item to the most conservative (e.g., the highest level hazardous waste) category for which a container is loaded into the station.

In an alternative embodiment, a station may indicate that the selected container is full and thus cannot accept any further waste items. In such a case, the station can instruct the user to replace container with an empty one of the same type. Alternatively, the station can instruct the user to use a container in a nearby station. In some embodiments, the station may offer the user a choice between replacing a container and using a nearby station.

The term "nearby" is a relative term, and can include any actual distance deemed appropriate by a particular user or system administrator. For example, in some embodiments, a station located on another floor of the hospital may be considered nearby, while in other embodiments, a sorting station across the hallway may not be considered nearby for the purposes of re-directing disposal of the waste item.

In some embodiments it may be inappropriate or undesirable to re-assign an item to a higher level container in the event that an appropriate waste category cannot be determined (e.g., as in step 350 of FIG. 24), or that an appropriate container cannot be located within an acceptable proximity (e.g., in step 368 of FIG. 25). In such embodiments, it may be desirable to provide a temporary holding space for items that cannot be placed in any currently present container. Such items can then be analyzed at a later time by a hazardous waste analyst in order to determine the most appropriate disposal of the item. Once such an analysis is performed, the analyst preferably enters such information into the category database in order to facilitate future sorting of items having similar characteristics.

In some embodiments, the waste sorting software can be configured to maintain a log file of all identified waste items and the categories/containers to which each item was assigned. Such information can be used by hospital administrators, regulatory auditors, pharmacists, or other entities to determine what items were disposed of and how. This information can be used to further optimize the sorting algorithm, to audit compliance with regulations, to audit usage or disposal of specific items, to alter a container arrangement in a station to increase sorting efficiency, or any of a variety of other purposes.

By enlisting the use of one or more embodiments of the present system, hospitals can demonstrate to their communities and their staff that they are participating in the improvement of the environment. It has been demonstrated by the US Geological Survey that the groundwater in the United States is contaminated with drugs. Although in trace amounts, the cumulative effect of these contaminants have been shown to be endocrine system disrupters contributing to the rise in cancers, birth defects and other ailments. By properly sorting the spent drugs into appropriate containers, the waste can be properly processed in order to leave only an inert residue that cannot contaminate the ground water.

Thus, embodiments of a medical waste sorting and disposal system advantageously provide a convenient means for clinicians to automatically sort pharmaceutical waste streams in order to comply with RCRA without the need to manually classify and sort each item individually. Additionally, the system advantageously provides hospitals with a means for participating in the improvement of the environment while avoiding fines for non-compliant waste disposal methods.

Additionally, as described above, some embodiments of the system can be configured to create a manifest to provide administrators suitable tracking information on the amount of a drug that has been actually used. Many hospitals are now moving toward implementing drug dispensing automation. The automation provides the hospital pharmacist and administrator information on what drugs are dispensed but not a convenient way of generating information on how much of a drug is used.

Medical Waste Treatment System

In one embodiment, a medical waste treatment system is provided. The medical waste treatment system is a product that renders infectious waste non-infectious, compacts it to a fraction of the original volume and uniquely maintains the treated material in a compact form. The cost of present embodiments of a medical waste treatment system is much less than competing technologies, because the footprint of the equipment is, in one embodiment, about one fourth the size. Competing technologies have cycle times that are long (usually about one hour) which necessitate large vessels for acceptable throughput versus the medical waste treatment system which has a cycle time of less than five minutes.

In one embodiment, the operating cost goal (about $0.09/lb) will be equal or better than most common technology, autoclave sterilization. Other competing technologies may have lower operating costs but they have many drawbacks. Incinerators have lower operating costs ($0.02/lb–0.04/lb) but it is possible that the EPA may tighten regulations and force many of the remaining incinerators to shut down. Many states do not allow incinerators to operate within their boundaries. For example, much of California's infectious waste is trucked to a Kansas City incinerator. The transportation costs add to the actual operating costs. Plasma technologies have equipment costs that are very high ($1–$3 million) and are, therefore, only suitable for central processing plants.

In one embodiment, a medical waste treatment system as a truck mounted service to hospitals is provided. The medical waste treatment system has significant advantages over truck mounted chemical processors. The medical waste treatment system unlike the chemical processors has a residue that is substantially innocuous such as common sand. It has been demonstrated that if there are any concentrations of organic matter, such as blood, the chemicals tend to be consumed by the organics leaving some of the remaining waste in a load untreated or partially treated. In one embodiment, the medical waste treatment system uses a unique heat technology that quickly and uniformly decontaminates the waste regardless of the amount of organics present. In several embodiments, the heat technology comprises use of sand or wax (including, but not limited to, paraffin) or a combination thereof. In one embodiment, the sand and/or wax is heated to a temperature of about 150° C. to about 250° C., preferably between about 165° C. to about 225° C. In one embodiment, the sand and/or wax is heated for less than about five minutes. One particular advantage of this method is the ability to produce highly stiff and/or compacted medical waste. In some embodiments, the volume and/or surface area of the treated medical waste is reduced to about 1/10 of its original size.

Up to about 50% of infectious medical waste can be plastic content, of which about 25% can include disposable PVC waste. Utilizing sand or wax to treat such plastic waste may not be any more cost effective than an Autoclave or other processing approach for these materials. It also may cause a number of problems such as the PVC outgassing chlorine because the temperature may be greater than 320 degrees ° F. (the effective melting temperature of PVC).

Thus, in one embodiment, a potential processing system for such plastic waste includes a rough grinder to grind the heterogeneous infectious medical waste into 2" by 5" strips. A second grinder grinds the waste into small pellets that are less than 0.25" in diameter. The waste pellets are mixed with a whitening agent and moisture that in the presence of UVC and/or UVA will cause an oxidative reaction which in turn will denature protein or organics, thereby inactivating some if not all of the microorganisms or spores present in the pelletized waste. This will set up the microorganisms and spores for a shorter sterilization procedure.

In some embodiments, the moisture can be removed by a desiccant dryer that may be heated and then conveyed to a hopper of a plastic extruder. The extruder can be set to temperature less than 320 degrees F. but hot enough to melt the PVC. Plasticizers and other additives may be introduced to get the heterogeneous pelletized mix of waste to flow homogeneously and not clump or dissociate. This process is also the final sterilization procedure. Many of the states have adopted a document called the STAAT II sterilization guideline that spells out the amount of reduction of spores and microorganisms required for sterilization.

In some embodiments, the effluent from this plastic-treating process could then be used as a filler for a product that is extruded rather than being placed in a land fill. Reducing disposal of solid waste is desirable because of the cost (0.02 to 0.05 cents per pound). One such product is a security fence that is composed of a hollow extrusion that forms posts and walls. The center is filled with extruded hospital waste that will provide the hollow extrusion with more weight and structural integrity. In another embodiment, a sandwich of compressed mylar sheets can be applied to the exterior of the fence to render the wall bullet resistant or proof.

Other embodiments are possible, for example freeway dividers, caskets, ashphalt filler for roads or any proprietary design that incorporates previously extruded hollow profiles that are filled with the extruded sterilized infectious medical waste can be used.

Medical Waste-Water Monitoring System

In one embodiment, a medical waste water management system is provided. In one embodiment this system is a water quality sampling service that is supplied to hospitals, clinics and labs. The product would be installed at the P trap of a sink. The medical waste-water monitoring system would sense water draining and a sample of water would be directed to a cuvette on a carousel. The samples could be taken randomly or in some predetermined sequence at a number of different sinks throughout a facility. The carousel of cuvettes would be removed, and then sent to an inside or outside lab for analysis. The analysis would pinpoint the location of any water pollution. Training classes to reinforce the proper disposal of pharmaceuticals are provided according to one embodiment of the invention. The service would continue on a less frequent basis once clinician habits had improved.

Despite a plethora of federal, state and local regulations, many clinicians continue to inappropriately dispose of pharmaceuticals in the sink. This is especially true of pharmaceutical spiked IV fluids. Verification of this practice has been established in a recent market research effort with 150 hospitals in which 60% of the respondents admitted to inappropriate disposal of drugs down the drain.

One advantage of several embodiments of this system is that it can pinpoint the source of the infraction. By combing this service along with the other Company products and services, the Company will have a sustainable competitive advantage.

Air Quality Monitoring System

The air quality monitoring system is a service that utilizes a device to sample the air quality, primarily in the pharmacy, oncology and operating room areas. It is intended to detect hazardous drugs including chemotherapeutics and anesthetics that become volatilized. The service is intended to provide clinicians with drug specific air quality information. The service will also suggest ways of eliminating the contaminants with both devices and a change in protocol. One advantage of some embodiments of this approach is that drug specific information that can be obtained.

Hospital Hazard Prevention

According to the Bureau of Labor Statistics, hospitals and nursing facilities are among the most hazardous work environments. Each year, an average of seven occupational injuries or illnesses out of 100 employees occurs. About half result in lost work time. Working with or exposure to toxic chemicals is the single largest contributing risk factor associated with occupational injury and illness in healthcare Although nanoemulsion disinfectants and microfiber materials for cleaning and disinfection have worked successfully to reduce toxicity, much opportunity remains to improve the hospital environment, making it safer for the healthcare worker. Reducing hospital hazards will also result in savings to the hospital.

In one embodiment, a system for a service to analyze and implement reductions in hospital hazards is provided. Implementing the solutions with hospital personnel will be a process similar to making cost reductions in organizations with significant numbers of administrative procedures.

Although certain embodiments and examples have been described herein, it will be understood by those skilled in the art that many aspects of the methods and devices shown and described in the present disclosure may be differently combined and/or modified to form still further embodiments. Additionally, it will be recognized that the methods described herein may be practiced using any device suitable for performing the recited steps. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined only by a fair reading of the claims that follow.

What is claimed is:

1. A waste system comprising:
   a station comprising a waste identification device and a plurality of container compartments and a plurality of container readers located adjacent to the container compartments, wherein the waste identification device determines different types of waste;
   a plurality of containers positioned in the container compartments, each container comprising a machine-readable identification key wherein each machine-readable identification key is associated with at least one waste category such that the machine-readable identification key is configured to indicate to at least one of the category of waste to be deposited into the container; and
   wherein the container readers are configured to read the machine-readable identification keys of containers positioned in the container compartments, and wherein the station is configured to determine the container into which waste should be deposited based on the waste category associated with the machine-readable identification key.

2. The system of claim 1, further comprising a controller configured to facilitate sorting of a plurality of waste items into respective containers.

3. The system of claim 1, wherein the waste category defines a class of waste to be placed in the containers.

4. The system of claim 3, wherein the waste category of a container is independent of the container compartment in which the container is positioned.

5. The system of claim 1, wherein each container compartment is configured to accept containers having any of a pre-determined group of identification keys.

6. The system of claim 1, wherein the identification keys comprise optically-readable markings.

7. The system of claim 6, wherein the identification keys comprise a pattern of holes in a portion of the container.

8. The system of claim 1, wherein each container comprises an automatically operable door.

9. The system of claim 8, wherein each container compartment is configured to operate a door of a container.

10. A waste sorting and disposal system comprising:
    a sorting and disposal station comprising a waste identification device and a plurality of container compartments and a plurality of container readers located adjacent to the container compartments, wherein the waste identification device determines different types of waste;
    a plurality of containers positioned in the container compartments, each container comprising a machine-readable identification key which identifies a waste category defining characteristics of the waste to be placed in each container such that the machine-readable identification key is configured to indicate to at least one of the container readers the category of waste to be deposited into the container;
    wherein the container readers are configured to read the machine-readable identification keys of containers positioned in container compartments, and wherein the station is configured to determine the container into which waste should be deposited based on the waste category associated with the machine-readable identification key; and
    wherein the waste category of each container is independent of the container compartment in which each container is positioned.

11. The system of claim 10, further comprising a controller configured to facilitate sorting of a plurality of waste items into respective containers.

12. The system of claim 10, wherein the controller is configured to adapt a sorting routine to a changing arrangement of containers and container compartments.

13. The system of claim 10, wherein the containers comprise translucent walls.

* * * * *

(12) EX PARTE REEXAMINATION CERTIFICATE (8873rd)
United States Patent
Mallett et al.

(10) Number: US 7,123,150 C1
(45) Certificate Issued: *Feb. 28, 2012

(54) WASTE CONTAINER IDENTIFICATION SYSTEM

(75) Inventors: Scott R. Mallett, Coto De Caza, CA (US); Randall C. Danta, Tustin, CA (US); Peter Regla, Placentia, CA (US); Alan D. Corey, Newport Beach, CA (US); Alan A. Davidner, Yorba Linda, CA (US)

(73) Assignee: Vesta Medical, LLC, Tustin, CA (US)

Reexamination Request:
No. 90/011,846, Sep. 8, 2011

Reexamination Certificate for:
Patent No.: 7,123,150
Issued: Oct. 17, 2006
Appl. No.: 10/946,208
Filed: Sep. 21, 2004

(*) Notice: This patent is subject to a terminal disclaimer.

Related U.S. Application Data

(63) Continuation of application No. 10/945,223, filed on Sep. 20, 2004, now Pat. No. 7,119,689.
(60) Provisional application No. 60/504,170, filed on Sep. 19, 2003, and provisional application No. 60/589,118, filed on Jul. 19, 2004.

(51) Int. Cl.
*G08B 13/14* (2006.01)

(52) U.S. Cl. ............ 340/572.1; 209/583; 209/703; 209/930; 235/375; 235/383; 235/385; 235/435; 235/462.01; 340/3.1; 340/572.8; 355/40; 355/41; 355/72; 355/74; 355/75; 705/2; 705/3; 705/308; 705/4

(58) Field of Classification Search ................ None
See application file for complete search history.

(56) References Cited

To view the complete listing of prior art documents cited during the proceeding for Reexamination Control Number 90/011,846, please refer to the USPTO's public Patent Application Information Retrieval (PAIR) system under the Display References tab.

*Primary Examiner* — Peter C. English

(57) ABSTRACT

A system for disposing of medical waste is generally configured to sort waste items into a plurality of disposable containers according to applicable rules and regulations governing the handling and/or disposal of such items. In some embodiments, a system comprises sorting stations, each of which houses a number of disposable containers. Each station can identify an item of waste, determine the most appropriate container for the item, and facilitate disposal of the item in the appropriate container.

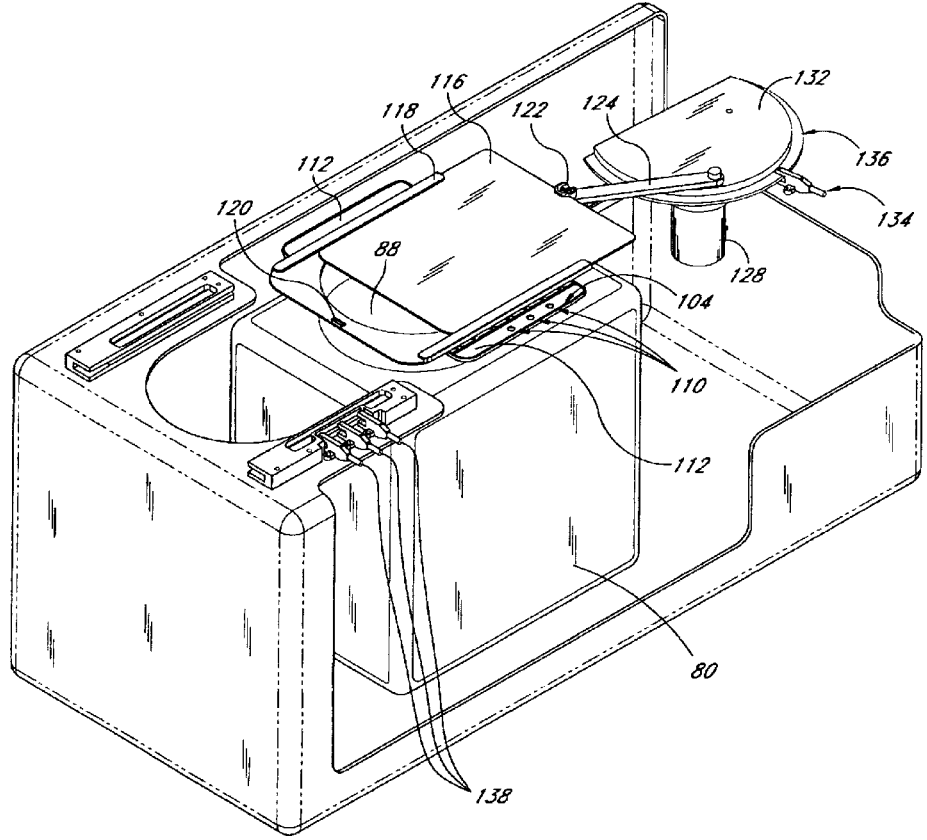

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 10 is confirmed.
Claims 2-9 and 11-13 were not reexamined.

\* \* \* \* \*